US007091230B2

(12) United States Patent
Adams et al.

(10) Patent No.: US 7,091,230 B2
(45) Date of Patent: Aug. 15, 2006

(54) 2-ARYLOXY-2-ARYLALKANOIC ACIDS FOR DIABETES AND LIPID DISORDERS

(75) Inventors: Alan D. Adams, Cranford, NJ (US); A. Brian Jones, Clavering (GB); Joel P. Berger, Hoboken, NJ (US); James F. Dropinski, Colts Neck, NJ (US); Alexander Elbrecht, Watchung, NJ (US); Kun Liu, Edison, NJ (US); Karen Lamb MacNaul, Warren, NJ (US); Guo-Qiang Shi, Monmouth Junction, NJ (US); Derek J. Von Langen, Fanwood, NJ (US); Gaochao Zhou, Scotch Plains, NJ (US)

(73) Assignee: Merck & Co., Inc., Rahway, NJ (US)

( * ) Notice: Subject to any disclaimer, the term of this patent is extended or adjusted under 35 U.S.C. 154(b) by 33 days.

(21) Appl. No.: 10/470,954

(22) PCT Filed: Feb. 5, 2002

(86) PCT No.: PCT/US02/04680

§ 371 (c)(1),
(2), (4) Date: Jul. 30, 2003

(87) PCT Pub. No.: WO02/064094

PCT Pub. Date: Aug. 22, 2002

(65) Prior Publication Data

US 2004/0092596 A1    May 13, 2004

Related U.S. Application Data

(60) Provisional application No. 60/267,809, filed on Feb. 9, 2001.

(51) Int. Cl.
*A61K 31/42* (2006.01)
*C07D 498/00* (2006.01)

(52) U.S. Cl. .................... 514/378; 514/571; 548/241; 562/463

(58) Field of Classification Search ............... 548/241
See application file for complete search history.

(56) References Cited

U.S. PATENT DOCUMENTS

| | | | |
|---|---|---|---|
| 3,378,582 A | 4/1968 | Bolhofer | |
| 3,517,050 A | 6/1970 | Bolhofer | |
| 3,787,423 A | 1/1974 | Bolhofer | |
| 3,816,446 A | 6/1974 | Bolhofer | |
| 3,953,465 A | 4/1976 | Bolhofer | |
| 4,125,729 A | 11/1978 | Trust et al. | |
| 4,125,732 A | 11/1978 | McEvoy et al. | |
| 4,168,385 A | 9/1979 | Trust et al. | |
| 4,748,272 A | 5/1988 | Youssefyeh | |
| 4,820,715 A | 4/1989 | Monkovic et al. | |
| 5,059,610 A | 10/1991 | Huang et al. | |
| 5,177,095 A | 1/1993 | Greenlee et al. | |
| 5,183,810 A | 2/1993 | Greenlee et al. | |
| 5,240,938 A | 8/1993 | Greenlee et al. | |
| 5,264,439 A | 11/1993 | Greenlee et al. | |
| 5,334,598 A | 8/1994 | Bagley et al. | |
| 5,374,638 A | 12/1994 | Dhanoa et al. | |
| 5,391,566 A | 2/1995 | Chakravarty et al. | |
| 5,401,745 A | 3/1995 | Bagley et al. | |
| 5,420,133 A | 5/1995 | Dhanoa et al. | |
| 5,449,682 A | 9/1995 | Greenlee et al. | |
| 5,519,138 A | 5/1996 | Ries et al. | |
| 5,538,991 A | 7/1996 | Ashton et al. | |
| 5,559,135 A | 9/1996 | Ashton et al. | |
| 5,565,485 A | 10/1996 | Bagley et al. | |
| 5,596,124 A | 1/1997 | Cary et al. | |
| 5,668,176 A | 9/1997 | Bagley et al. | |
| 5,688,974 A | 11/1997 | Devine et al. | |
| 5,708,186 A | 1/1998 | Devine et al. | |
| 5,767,310 A | 6/1998 | Bagley et al. | |
| 5,821,256 A | 10/1998 | Dorsch et al. | |
| 5,994,356 A | 11/1999 | Pieper et al. | |
| 6,110,963 A | 8/2000 | Malamas | |

FOREIGN PATENT DOCUMENTS

| | | |
|---|---|---|
| EP | 0 617 001 | 9/1994 |
| WO | WO 95/03044 | 2/1995 |
| WO | WO 96/09818 | 4/1996 |
| WO | WO 97/21693 | 6/1997 |
| WO | WO 97/21700 | 6/1997 |
| WO | WO 98/55454 | 12/1998 |
| WO | WO 99/58519 | 11/1999 |
| WO | WO 99/58521 | 11/1999 |
| WO | WO 00/74666 | 12/2000 |
| WO | WO 02/44113 | 6/2002 |

OTHER PUBLICATIONS

JP, HCAPLUS 1979:566381.
JP, CAPLUS 1987:439422.
JP, HCAPLUS 1989:75063.
JP, HCAPLUS 1999:572043.
Thomas F. Walsh, et al, "Potent Dual Antagonists of Endothelin and Angiotensin II Receptors Derived from alpha-Phenoxyphenylacetic Acids (Part III)", 1995, pp. 1155-1158, vol. 5, No. 11, Bioorganic & Medicinal Chemistry Letters.
T.C. Asthana, et al, "Alpha-Phenoxy- & Thiophenoxyphenylacetic Acid Derivatives as Hypoglycaemic Agents", 1970, pp. 1086-1095, vol. 8, Indian Journal of Chemistry.

(Continued)

*Primary Examiner*—Kamal A. Saeed
(74) *Attorney, Agent, or Firm*—James L. McGinnis; Melvin Winokur

(57) ABSTRACT

A class of 2-aryloxy-2-arylalkanoic acids comprises compounds that are potent agonists of PPAR alpha and/or gamma, and are therefore useful in the treatment, control or prevention of non-insulin dependent diabetes mellitus (NIDDM), hyperglycemia, dyslipidemia, hyperlipidemia, hypercholesterolemia, hypertriglyceridemia, atherosclerosis, obesity, vascular restenosis, inflammation, and other PPAR alpha and/or gamma mediated diseases, disorders and conditions.

28 Claims, No Drawings

OTHER PUBLICATIONS

Shamina M. Rangwala, et al, "Stereoselective Effects of Chiral Clofibric Acid Analogs on Rat Peroxisome Proliferator—Activated Receptor alpha (rPPARalpha) Activation and Peroxisomal Fatty Acid Beta-Oxidation" Chirality 9:37-47 (1997).

Daljit S. Shanoa, et al, "(Dipropylphenoxy)phenylacetic Acids: A New Generation of Nonpeptide Angiotensin II Receptor Antagonist", J. Med. Chem. 1993, 36, 3738-3742.

Holly T. Beauchamp, et al, "In Vivo Receptor Occupancy of the Angiotensin II Receptor by Nonpeptide Antagonists: Relationship to In Vitro Affinities and In Vivo Pharmacologic Potency", JPET, vol. 272, No. 2, 612-618. 1995.

D. Pitre, et al, "Mezzi Di Contrasto Radiologici", Il Farmaco—Ed. C.—vol. 27—No. 5, 1972, pp. 408-418.

G. Tilly, "Synthese de nouveaux moyens de contraste radiologiques pour la cholecystographie", Chimie Therapeutique, 1967, pp. 57-65.

H. Cassebaum, et al "Neue intravenos applizierbare Gallenkontrastmittel", pp. 470-474, 1967.

Giuseppe Campiani, et al, "Pyrrolobenzothiazepinones and Pyrrolobenzoxazepinones: Novel and Specific Non-Nucleoside HIV—1 Reverse Transcriptase Inhibitors with Antiviral Activity", J. Med. Chem. 1996, 39, 2672-2680.

2-ARYLOXY-2-ARYLALKANOIC ACIDS FOR DIABETES AND LIPID DISORDERS

CROSS REFERENCE TO RELATED APPLICATIONS

This application is a U.S. National Phase application under 35 U.S.C. § 371 of PCT Application No. PCT/US02/04680, filed Feb. 5, 2002, and claims priority under 35 U.S.C. § 119 (e) from U.S. Application No. 60/267,809, filed Feb. 9, 2001.

FIELD OF THE INVENTION

The instant invention is concerned with 2-aryloxy-2-arylalkanoic acids and pharmaceutically acceptable salts and prodrugs thereof which are useful as therapeutic compounds, particularly in the treatment and prevention of Type 2 diabetes mellitus, often referred to as non-insulin dependent diabetes (NIDDM), of conditions that are often associated with this disease, and of lipid disorders.

BACKGROUND OF THE INVENTION

Diabetes refers to a disease process derived from multiple causative factors and characterized by elevated levels of plasma glucose or hyperglycemia in the fasting state or after administration of glucose during an oral glucose tolerance test. Persistent or uncontrolled hyperglycemia is associated with increased and premature morbidity and mortality. Often abnormal glucose homeostasis is associated both directly and indirectly with alterations of the lipid, lipoprotein and apolipoprotein metabolism and other metabolic and hemodynamic disease. Therefore patients with Type 2 diabetes mellitus are at especially increased risk of macrovascular and microvascular complications, including coronary heart disease, stroke, peripheral vascular disease, hypertension, nephropathy, neuropathy, and retinopathy. Therefore, therapeutical control of glucose homeostasis, lipid metabolism and hypertension are critically important in the clinical management and treatment of diabetes mellitus.

There are two generally recognized forms of diabetes. In type 1 diabetes, or insulin-dependent diabetes mellitus (IDDM), patients produce little or no insulin, the hormone which regulates glucose utilization. In type 2 diabetes, or noninsulin dependent diabetes mellitus (NIDDM), patients often have plasma insulin levels that are the same or even elevated compared to nondiabetic subjects; however, these patients have developed a resistance to the insulin stimulating effect on glucose and lipid metabolism in the main insulin-sensitive tissues, which are muscle, liver and adipose tissues, and the plasma insulin levels, while elevated, are insufficient to overcome the pronounced insulin resistance.

Insulin resistance is not primarily due to a diminished number of insulin receptors but to a post-insulin receptor binding defect that is not yet understood. This resistance to insulin responsiveness results in insufficient insulin activation of glucose uptake, oxidation and storage in muscle and inadequate insulin repression of lipolysis in adipose tissue and of glucose production and secretion in the liver.

The available treatments for type 2 diabetes, which have not changed substantially in many years, have recognized limitations. While physical exercise and reductions in dietary intake of calories will dramatically improve the diabetic condition, compliance with this treatment is very poor because of well-entrenched sedentary lifestyles and excess food consumption, especially of foods containing high amounts of saturated fat. Increasing the plasma level of insulin by administration of sulfonylureas (e.g. tolbutamide and glipizide), which stimulate the pancreatic β-cells to secrete more insulin, and/or by injection of insulin after the response to sulfonylureas fails, will result in high enough insulin concentrations to stimulate the very insulin-resistant tissues. However, dangerously low levels of plasma glucose can result from these last two treatments, and increasing insulin resistance due to the even higher plasma insulin levels can occur. The biguanides increase insulin sensitivity resulting in some correction of hyperglycemia. However, the two biguanides, phenformin and metformin, can induce lactic acidosis and nausea/diarrhea, respectively.

The glitazones (i.e. 5-benzylthiazolidine-2,4-diones) are a more recently described class of compounds with potential for a novel mode of action in ameliorating many symptoms of type 2 diabetes. These agents substantially increase insulin sensitivity in muscle, liver and adipose tissue in several animal models of type 2 diabetes resulting in partial or complete correction of the elevated plasma levels of glucose without occurrence of hypoglycemia. For a review, see Willson, T. M. et al., *J. Med. Chem.*, 43(4) 527–550, (2000).

Disorders of lipid metabolism or dyslipidemias include various conditions characterized by abnormal concentrations of one or more lipids (i.e. cholesterol and triglycerides), and/or apolipoproteins (i.e., apolipoproteins A, B, C and E), and/or lipoproteins (i.e., the macromolecular complexes formed by the lipid and the apolipoprotein that allow lipids to circulate in blood, such as Low Density Lipoproteins (LDL), Very Low Density Lipoproteins (VLDL) and Intermediate Density Lipoproteins (IDL). Cholesterol is mostly carried in Low Density Lipoproteins (LDL), and this component is commonly known as the "bad" cholesterol because it has been shown that elevations in LDL-cholesterol correlate closely to the risk of coronary heart disease. A smaller component of cholesterol is carried in the High Density Lipoproteins (HDL) and is commonly known as the "good" cholesterol. In fact, it is known that the primary function of HDL is to accept cholesterol deposited in the arterial wall and to transport it back to the liver for disposal through the intestine. Although it is desirable to lower elevated levels of LDL cholesterol, it is also desirable to increase levels of HDL cholesterol. Generally, it has been found that increased levels of HDL are associated with lower risk for coronary heart disease (CHD). See, for example, Gordon, et al., Am. J. Med., 62, 707–714 (1977); Stampfer, et al., N. England J. Med., 325, 373–381 (1991); and Kannel, et al., Ann. Internal Med., 90, 85–91(1979). An example of an HDL raising agent is nicotinic acid, a drug with limited utility because doses that achieve HDL raising are associated with undesirable effects, such as flushing.

Dyslipidemias were originally classified by Fredrickson according to the combination of alterations mentioned above. The Fredrickson classification includes 6 phenotypes (i.e., I, IIa, IIb, III, IV and V) with the most common being the isolated hypercholesterolemia (or type IIa) which is usually accompained by elevated concentrations of total and LDL cholesterol. The initial treatment for hypercholesterolemia is often to modify the diet to one low in fat and cholesterol, coupled with appropriate physical exercise, followed by drug therapy when LDL-lowering goals are not met by diet and exercise alone A second common form of dyslipidemia is the mixed or combined hyperlipidemia or type IIb and III of the Fredrickson classification. This dyslipidemia is often prevalent in patients with type 2 diabetes, obesity and the metabolic syndrome. In this dyslipidemia there are modest elevations of LDL-cholesterol, accompanied by more pronounced elevations of small dense LDL-cholesterol particles, VLDL and/or IDL (i.e., triglyceride rich lipoproteins), and total triglycerides. In addition, concentrations of HDL are often low.

Peroxisome proliferators are a structurally diverse group of compounds that when administered to rodents elicit dramatic increases in the size and number of hepatic and renal peroxisomes, as well as concomitant increases in the capacity of peroxisomes to metabolize fatty acids via increased expression of the enzymes of the beta-oxidation cycle. Compounds of this group include but are not limited to the fibrate class of lipid modulating drugs, herbicides and phthalate plasticizers. Peroxisome proliferation is also triggered by dietary or physiological factors such as a high-fat diet and cold acclimatization.

Three sub-types of peroxisome proliferator activated receptor (PPAR) have been discovered and described; they are peroxisome proliferator activated receptor alpha (PPARα), peroxisome proliferator activated receptor gamma (PPARγ) and peroxisome proliferator activated receptor delta (PPARδ). Identification of PPARα, a member of the nuclear hormone receptor superfamily activated by peroxisome proliferators, has facilitated analysis of the mechanism by which peroxisome proliferators exert their pleiotropic effects. PPARα is activated by a number of medium and long-chain fatty acids, and it is involved in stimulating β-oxidation of fatty acids. PPARα is also associated with the activity of fibrates and fatty acids in rodents and humans. Fibric acid derivatives such as clofibrate, fenofibrate, bezafibrate, ciprofibrate, beclofibrate and etofibrate, as well as gemfibrozil, each of which are PPARα ligands and/or activators, produce a substantial reduction in plasma triglycerides as well as some increase in HDL. The effects on LDL cholesterol are inconsistent and might depend upon the compound and/or the dyslipidemic phenotype. For these reasons, this class of compounds has been primarily used to treat hypertriglyceridemia (i.e, Fredrickson Type IV and V) and/or mixed hyperlipidemia.

The PPARγ receptor subtypes are involved in activating the program of adipocyte differentiation and are not involved in stimulating peroxisome proliferation in the liver. There are two known protein isoforms of PPARγ: PPARγ1 and PPARγ2 which differ only in that PPARγ2 contains an additional 28 amino acids present at the amino terminus. The DNA sequences for the human isotypes are described in Elbrecht, et al., BBRC 224;431–437 (1996). In mice, PPARγ2 is expressed specifically in fat cells. Tontonoz et al., Cell 79: 1147–1156 (1994) provide evidence to show that one physiological role of PPARγ2 is to induce adipocyte differentiation. As with other members of the nuclear hormone receptor superfamily, PPARγ2 regulates the expression of genes through interaction with other proteins and binding to hormone response elements, for example in the 5' flanking regions of responsive genes. An example of a PPARγ2 responsive gene is the tissue-specific adipocyte P2 gene. Although peroxisome proliferators, including the fibrates and fatty acids, activate the transcriptional activity of PPAR's, only prostaglandin $J_2$ derivatives have been identified as potential natural ligands of the PPARγ subtype, which also binds thiazolidinedione antidiabetic agents with high affinity.

The human nuclear receptor gene PPARδ (hPPARδ) has been cloned from a human osteosarcoma cell cDNA library and is fully described in A. Schmidt et al., *Molecular Endocrinology*, 6:1634–1641 (1992). It should be noted that PPARδ is also referred to in the literature as PPARβ and as NUC1, and each of these names refers to the same receptor; in Schmidt et al. the receptor is referred to as NUC1.

In WO96/01430, a human PPAR subtype, hNUC1B, is disclosed. The amino acid sequence of hNUC1B differs from human PPARδ (referred to therein as hNUC1) by one amino acid, i.e., alanine at position 292. Based on in vivo experiments described therein, the authors suggest that hNUC1B protein represses hPPARα and thyroid hormone receptor protein activity.

It has been disclosed in WO97/28149 that agonists of PPARδ are useful in raising HDL plasma levels. WO97/27857, 97/28115, 97/28137 and 97/27847 disclose compounds that are useful as antidiabetic, antiobesity, antiatherosclerosis and antihyperlipidemic agents, and which may exert their effect through activation of PPARs.

It is generally believed that glitazones exert their effects by binding to the peroxisome proliferator activated receptor (PPAR) family of receptors, controlling certain transcription elements having to do with the biological entities listed above. See Hulin et al., Current Pharm. Design (1996) 2, 85–102.

A number of glitazones that are PPAR agonists have been approved for use in the treatment of diabetes. These include troglitazone, rosiglitazone and pioglitazone, all of which are primarily or exclusively PPARγ agonists. Many of the newer PPAR agonists that are currently under development or are in clinical trials have dual PPARα and γ activity. These are expected to improve both insulin sensitivity and the lipid profile in patients having NIDDM.

Although glitazones are beneficial in the treatment of NIDDM, there have been some serious adverse events associated with the use of the compounds. The most serious of these has been liver toxicity, which has resulted in a number of deaths. The most serious problems have occurred using troglitazone, which was recently withdrawn from the US market due to these concerns about toxicity. Because of the problems that have occurred with the glitazones, researchers in a number of laboratories have been investigating classes of PPAR agonists that are not glitazones and do not contain 1,3-thiazolidinedione moieties.

Compounds that are not glitazones but are agonists of PPAR sub-types are expected to be useful in the treatment of diabetes and associated conditions. PPARα agonists should improve the lipid profile and alleviate dyslipidemias by reducing elevated LDL levels and elevated triglyceride levels and/or increasing HDL levels. PPARγ agonists should improve insulin sensitivity, reducing the need for insulin injections in patients with NIDDM. The role of PPARδ is less well defined.

The class of compounds described herein is novel. Structurally similar kinds of compounds have been synthesized and invesigated for other uses, particularly as angiotensin II antagonists. A few related classes of compounds have also been reported to be modulators of arichidonic acid pathways (U.S. Pat. No. 4,748,272), to activate fatty acid oxidation in rats (S. M. Rangwala et al., Chirality (1997), 9, 37–47), or to have at least some hypoglycemic activity (T. C. Asthana et al., Indian J. Chem. (1970), 8, 1086–1095, and U.S. Pat.

Nos. 4,748,272 and 6,110,963). These classes of compounds appear to have relatively low activity or to modulate glucose metabolism by a different mechanism than the compounds described herein (e.g. PTP-1B antagonism).

SUMMARY OF THE INVENTION

The class of compounds described herein is a new class of PPAR agonists. The compounds in this class do not contain a 1,3-thiazolidinedione moiety in their molecular structure and therefore are not glitazones. This class of compounds includes compounds that are primarily PPARα agonists, compounds that are mixed PPARα/γ agonists, and to a lesser extent, compounds that are primarily PPARγ agonists. The clinical effects are expected to vary depending on the balance in agonism of the PPAR-subtypes. These compounds are useful in the treatment, control and/or prevention of diabetes, hyperglycemia, mixed or diabetic dyslipidemia, and other lipid disorders (including isolated hypercholesterolemia as manifested by elevations in LDL-C and/or non-HDL-C and/or hyperapoBliproteinemia, hypertriglyceridemia and/or increase in triglyceride-rich-lipoproteins, and/or low HDL cholesterol concentrations), atherosclerosis, obesity, vascular restenosis, inflammatory conditions, neoplastic conditions, and other PPARα and/or γ mediated diseases, disorders and conditions.

The present invention provides compounds having the structure of Formula I, including pharmaceutically acceptable salts and prodrugs of these compounds:

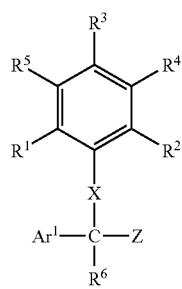

I

In the compounds of Formula I:

$R^1$ is selected from the group consisting of (a) halogen, (b) $C_{1-6}$ alkyl, where alkyl is linear or branched and is optionally substituted with 1–3F, and (c) —$OC_1$–$C_6$ alkyl, where —$OC_1$–$C_6$ alkyl is linear or branched and is optionally substituted with 1–3 halogens, independently selected from Cl and F, with the proviso that $R^1$ and $R^2$ are not both $CH_3$, further provided that if $R_1$ is Cl and R3 is $C_4$alkyl, then $R^7$ is not 4-chlorophenoxy, and further provided that if $R^1$ or $R^2$ is propyl and $R^3$ is acetyl, then the other of $R^1$ and $R^2$ is not methyl;

$R^2$ is selected from the group consisting of $C_1$–$C_6$ alkyl and $C_3$–$C_{12}$ Alicyclic, wherein alkyl is linear or branched and is optionally substituted with 1–3F, and Alicyclic is optionally substituted with 1–5 halogens;

$R^3$ is selected from the group consisting of $C_2$–$C_6$ alkyl, —$C(O)C_1$–$C_6$ alkyl, —$C(O)$Aryl, —$C(O)C_3$–$C_{12}$Alicyclic, —$C(O)$Heterocycle, —$C(O)$Heteroaryl, —$OC_{1-6}$ alkyl, —OAryl, —OHeterocycle, and —OHeteroaryl, wherein alkyl in all occurrences may be linear or branched and is optionally substituted with one or more substituents selected from (a) 1–5 Cl and/or F atoms and/or (b) one Aryl or Heteroaryl; and wherein Aryl, Heterocycle, and Heteroaryl are optionally substituted with 1–3 substituents independently selected from the group consisting of Cl, F, Br, linear or branched $C_1$–$C_5$ alkyl optionally substituted with 1–5 halogens, Aryl optionally substituted with 1–5 halogens, and linear or branched —$OC_1$–$C_5$ alkyl optionally substituted with 1–5 halogens;

—$R^4$ is selected from the group consisting of H, —OH, —$OC_1$–$C_6$-alkyl, —OHeterocycle, —OHeteroaryl, and halogen, wherein —Oalkyl may be linear or branched and is optionally substituted with 1–3 halogens independently selected from F and Cl, and wherein Heterocycle and Heteroaryl are optionally substituted with 1–3 substituents independently selected from Cl, F, Br, $C_1$–$C_5$ alkyl and —$OC_1$–$C_5$ alkyl, where $C_1$–$C_5$ alkyl and —$OC_1$–$C_5$ alkyl may be linear or branched and optionally may be substituted with 1–5 halogens independently selected from Cl and F; or optionally, $R^3$ and $R^4$ may be joined together to yield a 5- or 6-membered ring containing (a) 1–3 heteroatoms selected from O, N and S, (b) 2–5 carbon atoms, and (c) optionally one carbonyl group, wherein the 5- or 6-membered ring is fused to the benzene ring, and the benzene ring and fused 5- or 6-membered ring together form a Heteroaryl or Heterocycle which optionally contains one carbonyl group in the 5- or 6-membered fused ring and which is optionally substituted on the 5- or 6-membered fused ring with 1–2 substituents independently selected from $R^8$;

$R^5$ is H or Halogen;

$R^6$ is selected from the group consisting of H, halogen, $CH_3$ and $CF_3$;

Each $R^7$ is independently selected from the group consisting of halogen, $C_1$–$C_6$ alkyl, $C_1$–$C_6$ alkoxy, —$SC_{1-6}$ alkyl, —OAryl, $C_2$–$C_6$ alkenyl, $C_2$–$C_6$ alkynyl, —CN, —$C(O)OC_1$–$C_3$ alkyl, and —$C(O)C_1$–$C_3$alkyl, wherein each alkyl, alkenyl, alkoxy and alkynyl and each alkyl portion of a substituent is linear or branched and is optionally substituted with 1–5 halogen atoms and/or 1 substituent selected form Aryl and Heteroaryl, and each Aryl and Heteroaryl is optionally substituted with 1–3 groups independently selected from halogen, $CH_3$, $CF_3$, —$OCH_3$ and —$OCF_3$;

Each $R^8$ is independently selected from the group consisting of (a) —$OC_1$–$C_5$ alkyl, which may be linear or branched and is optionally substituted with 1–3 F; (b) $C_1$–$C_9$ alkyl, which may be linear or branched and is optionally substituted with one Aryl, 1–5 halogens independently selected from Cl and F, and/or one —COOH; (c) Aryl; and (d) Heteroaryl; wherein Aryl and Heteroaryl are optionally substituted with 1–3 substituents independently selected from the group consisting of Cl, F, $C_1$–$C_5$ alkyl, and —$OC_1$–$C_5$alkyl, wherein each alkyl and each —$OC_1$–$C_5$alkyl may be linear or branched, and is optionally substituted with 1–3 substituents independently selected from halogen —$OCH_3$, and —$OCF_3$;

Aryl is an aromatic carbocyclic mono- or bicyclic ring system containing 6–10 atoms in the ring or rings;

Heteroaryl is a mono- or bicyclic aromatic ring system containing 4–11 atoms in the ring or rings, wherein at least one atom in the ring or rings is a heteroatom selected from N, O and S;

Heterocycle is a fully or partially saturated monocyclic or bicyclic ring system having 4–11 atoms in the ring or rings and at least one heteroatom selected from O, N, and S in the ring or rings;

Alicyclic is a substituent group that has one $C_3$–$C_6$cycloalkyl and one or more alkyl groups which may be linear or branched attached to the cycloalkyl group, wherein the point of attachment may be through the cycloalkyl or through an alkyl group;

$Ar^1$ is selected from the group consisting of phenyl, thienyl, thiazolyl, oxazolyl and pyridyl, and is optionally substituted with Aryl or 1–3 groups independently selected from $R^7$;

X is O or S; and

Z is selected from the group consisting of —COOH, tetrazole, and —C(O)NHS(O)$_2$R$^8$.

These compounds are effective in lowering glucose, lipids, and insulin in diabetic animals. The compounds are expected to be efficacious in the treatment, control and/or prevention of non-insulin dependent diabetes mellitus (NIDDM) in humans and in the treatment, control, and/or prevention of hyperlipidemia, dyslipidemia, obesity, hypercholesterolemia, hypertrigyceridemia, atherosclerosis, vascular restenosis, inflammatory conditions, neoplastic conditions, and other PPARα and/or γ mediated diseases, disorders and conditions in humans. Diseases, disorders and conditions from the latter group listed above often accompany NIDDM.

DETAILED DESCRIPTION OF THE INVENTION

The invention has numerous embodiments. Several groups and subgroups of compounds are described below:

One preferred embodiment comprises compounds having formula I in which X is O. Compounds in which X is S make up a second embodiment.

Another group comprises compounds having formula I in which Z is —CO$_2$H.

A group of preferred compounds having formula I comprises compounds in which $R^3$ is selected from $C_2$–$C_6$ alkyl, —C(O)$C_2$–$C_6$ alkyl, —C(O)Aryl, —C(O)$C_3$–$C_{12}$Alicyclic, and —OC$_{1-6}$ alkyl, where alkyl in all occurrences is linear or branched and is optionally substituted with one or more substituents selected from (a) 1–5 Cl and/or F atoms, and/or (b) one Aryl, where Aryl in all occurences is optionally substituted with 1–3 substituents independently selected from Cl, F, Br, and linear or branched $C_1$–$C_5$ alkyl optionally substituted with 1–5 halogens. A sub-group of compounds from this group comprises compounds in which $R^3$ is selected from $C_2$–$C_6$ alkyl, —C(O)$C_2$–$C_6$ alkyl, —C(O)$C_3$–$C_{12}$Alicyclic, and —OC$_{1-6}$ alkyl, where alkyl in all occurrences is linear or branched and is optionally substituted with one or more substituents selected from (a) 1–5 Cl and/or F atoms, and/or (b) one Aryl, where Aryl in all occurences is optionally substituted with 1–3 substituents independently selected from Cl, F, Br, and linear or branched $C_1$–$C_5$ alkyl optionally substituted with 1–5 halogens.

A subset of compounds having formula I includes compounds in which $R^3$ and $R^4$ are as previously defined and are not joined together to yield a 5- or 6-membered ring fused to the phenoxy or thiophenoxy ring.

An alternative subset comprises compounds of this invention having formula 1a:

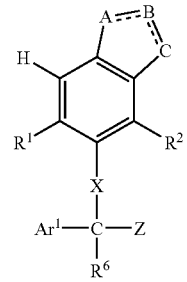

Ia including pharmaceutically acceptable salts and prodrugs thereof, where

A-B and B—C are each connected by a bond. Optionally the bond between A-B or B—C can be a double bond, thereby yielding a five-membered ring fused to the benzene ring to which A and C are bonded, where A, B, and C are each independently selected from N, NR$^9$, C, CR$^9$, CR$^9{}_2$, C=O, O, S, S(O), and S(O)$_2$, where at least one of A, B, and C comprises a heteroatom selected from N, S and O that is in the ring (additional heteroatoms may also be attached to the ring; such as O in the form of a carbonyl or S oxide or S dioxide.

Each $R^9$ is independently selected from $R^8$ and H; and $R^1$, $R^2$, $R^6$, $R^7$, $R^8$, Ar$^1$, X and Z are as defined in claim 1.

Many preferred compounds have formula I or Ia as defined above, where X is O and Z is —CO$_2$H.

$R^6$ is very often H in preferred compounds having Formula I or Ia.

In many preferred compounds having formula I or Ia as defined for any of the embodiments or subsets above, Ar$^1$ is phenyl or pyridyl, which is optionally substituted with 1–3 groups independently selected from R$^7$. The preferred choice for Ar$^1$ is phenyl.

Preferred selections for substituent groups in any of the groups of compounds described above are the following:

$R^1$ is selected from Cl, F, and $C_2$–$C_4$ alkyl, which may be linear or branched and is optionally substituted with 1–3F. In a preferred group of compounds, the $R^1$ groups are $C_{2-4}$alkyl. Linear $C_{2-4}$alkyl are preferred. Linear n-$C_3$–$C_4$ are very preferred.

$R^2$ is $C_2$–$C_4$ alkyl, which may be linear or branched and is optionally substituted with 1–3F. In many preferred compounds, $R^2$ is linear or branched $C_2$–$C_4$ alkyl. Linear or branched $C_3$–$C_4$ alkyl is very preferred for $R^2$, and n-$C_3$–$C_4$ alkyl is highly preferred.

$R^3$ is —C(O)$C_2$–$C_6$alkyl or $C_3$–$C_6$alkyl, where each alkyl group may be linear or branched and is optionally substituted with 1–5-halogen. In many preferred compounds, $R_3$ may be linear or branched —C(O)$C_2$–$C_6$alkyl, and in many compounds is linear or branched —C(O)$C_2$–$C_4$alkyl.

$R^4$ is selected from H, —OH, —OC$_1$–$C_6$-alkyl, Cl and F, where —OC$_1$–$C_6$alkyl is linear or branched and is optionally substituted with 1–3 F. In other preferred embodiments, R4 is H, Cl, F or —OH.

In a preferred group of compounds, $R^3$ and $R^4$ are joined together to form a 5- or 6-membered ring containing 1–3 heteroatoms selected from S, N, and O in the ring that is fused to the benzene ring to which $R^3$ and $R^4$ are attached.

In many preferred compounds within this group, the benzene ring and 5- or 6-membered ring together form a fused ring system which is selected from benzisoxazole, benzisothiazole, benzthiazole, benzoxazole, quinoline, isoquinoline, chromene, benzofuran, benzothiophene, benzimidazole, indole, benzoxazolone, benzisoxazolone; and benzimidazolone. The 5- or 6-membered ring containing a heteroatom is eptionally substituted with 1–2 substituents independently selected from $R^8$. In a preferred embodiment, $R^3$ and $R^4$ are joined together to form a 5-membered ring fused to the benzene ring, yielding a heteroaromatic ring system. Ths heteroaromatic ring system is preferably selected from benzisoxazole, benzisothiazole, benzthiazole, benzoxazole, benzofuran, benzothiophene, benzimidazole, indole, benzoxazolone, benzisoxazolone, and benzimidazolone.

$R^5$ is preferably H.

In any of the above embodiments, $R^6$ is often H, halogen, $CH_3$, or $CF_3$. $R^6$ is preferably H.

In any of the above embodiments, $R^7$ is $C_1$–$C_6$alkyl, —OAryl, $C_3$–$C_{12}$Alicyclic, —O$C_1$–$C_6$alkyl, —S$C_1$–$C_6$alkyl or —C(O)$C_1$–$C_3$alkyl, where alkyl in each occurrence is linear or branched and is optionally substituted with 1–3 halogens and/or one substituent selected from Aryl and Heteroaryl, and each Aryl and Heteroaryl is optionally substituted with 1–3 substituents independently selected from halogen, $CH_3$, $CF_3$, —$OCH_3$ and —$OCF_3$. In preferred compounds, each $R^7$ is independently selected from F, Cl, $C_1$–$C_4$ alkyl, —O$C_1$–$C_4$ alkyl, —S$C_1$–$C_4$ alkyl, and —Ophenyl, wherein in each instance, alkyl is linear or branched and is optionally substituted with 1–5 F, and —Ophenyl is optionally substituted with 1–3 substituents independently selected from halogen, $CH_3$, $CF_3$, —$OCH_3$ and —$OCF_3$.

Each $R^8$ is independently selected from halogen, $C_1$–$C_3$alkyl, and phenyl, wherein $C_1$–$C_3$alkyl is linear or branched and is optionally substituted with 1–3 halogens, and phenyl is optionally substituted with 1–3 substituents independently selected from halogen, $CH_3$, $CF_3$, —$OCH_3$ and —$OCF_3$.

A preferred embodiment comprises compounds having formula I in which $R^3$ and $R^4$ are not joined together to yield a 5-membered ring, and the substituent groups are as follows:

$R^1$ is Cl, F or linear or branched $C_2$–$C_4$alkyl;
$R^2$ is linear or branched $C_2$–$C_4$alkyl;
$R^3$ is linear or branched —C(O)$C_2$–$C_4$ alkyl;
$R^4$ is H, Cl, F, or —OH;
$R^5$ and $R^6$ are H; and
Each $R^7$ is independently selected from F, Cl, $C_1$–$C_4$ alkyl, —O$C_1$–$C_4$ alkyl, —S$C_1$–$C_4$ alkyl, and —Ophenyl, wherein in each instance, alkyl is linear or branched and is optionally substituted with 1–5 F, and —Ophenyl is optionally substituted with 1–3 substituents independently selected from halogen, $CH_3$, $CF_3$, —$OCH_3$ and —$OCF_3$.

In a preferred subgroup of compounds having formula I as defined immediately above, $R^1$ and $R^2$ are n-$C_3$–$C_4$ alkyl; $R^4$ is selected from H, —OH, and F; and $R^3$ is linear —C(O)$C_2$–$C_4$ alkyl. In many preferred compounds in this subgroup, $Ar^1$ is phenyl, which is optionally substituted with 1–3 $R^7$. A preferred group of compounds includes compounds in which $R^1$ and $R^2$ are n-propyl, $R^3$ is —C(=O)$C_2H_5$, and $R^4$ is H.

A subset of compounds having formula Ia as defined above includes compounds having the group -A-B—C—, in which the bonds between A and B and between B and C are optionally single or double bonds, where -A-B—C— is selected from the group consisting of:

—C($R^9$)=N—O—,
—C($R^9$)=N—S—,
—C($R^9$)$_2$—N($R^9$)—O—,
—C($R^9$)$_2$—N($R^9$)—S—,
—N($R^9$)—C(=O)—O—,
—N($R^9$)—C(=O)—S—,
—N($R^9$)—O—C(=O)—,
—N($R^9$)—S—C(=O)—,
—N=C($R^9$)—O—,
—N=C($R^9$)—S—,
—N($R^9$)—C($R^9$)$_2$—O—,
—N($R^9$)—C($R^9$)$_2$—S—,
—C(=O)—N($R^9$)—O—;
—C(=O)—N($R^9$)—S—;
—C(=O)—O—N($R^9$)—; and
—C(=O)—S—N($R^9$)—;

and the group —C—B-A- is selected from the group consisting of:
—C($R^9$)=N—O—,
—C($R^9$)=N—S—,
—C($R^9$)$_2$—N($R^9$)—O—,
—C($R^9$)$_2$—N($R^9$)—S—,
—N($R^9$)—C(=O)—O—,
—N($R^9$)—C(=O)—S—,
—N($R^9$)—O—C(=O)—,
—N($R^9$)—S—C(=O)—,
—N=C($R^9$)—O—,
—N=C($R^9$)—S—,
—N($R^9$)—C($R^9$)$_2$—O—,
—N($R^9$)—C($R^9$)$_2$—S—,
—C(=O)—N($R^9$)—O—;
—C(=O)—N($R^9$)—S—;
—C(=O)—O—N($R^9$)—; and
—C(=O)—S—N($R^9$)—

Preferred compounds having Formula Ia as defined above include compounds in which A is CR9, C=O, or NR9; B is N, NR9, or C=O; and C is O. In more preferred compounds having formula Ia, the group -A-B—C— is selected from —C($R^9$)=N—O—, —C(=O)—N($R^9$)—O—, and —N($R^9$)—C(=O)—O—.

In preferred embodiments of the compounds having formula Ia described above, $R^1$ is selected from Cl, F, and $C_2$–$C_4$ alkyl, which may be linear or branched and is optionally substituted with 1–3F. In more preferred embodiments, $R^1$ is Cl, F or linear or branched $C_2$–$C_4$alkyl, where $C_2$–$C_4$alkyl is not substituted. In very preferred embodiments, $R^1$ is selected from Cl, F and n-$C_3$–$C_4$alkyl.

—$Ar^1$ is phenyl, which is optionally substituted with 1–3 groups independently selected from $R^7$.

In preferred embodiments, $R^2$ is $C_2$–$C_4$ alkyl, which may be linear or branched and is optionally substituted with 1–3F. Preferably, $R^2$ is linear or branched $C_2$–$C_4$alkyl and is not substituted. In a very preferred group of compounds, $R^2$ is n-$C_3$–$C_4$alkyl.

In preferred embodiments, $R^6$ is selected from H, halogen, $CH_3$, and $CF_3$. Preferably, $R^6$ is H.

In preferred embodiments, each $R^7$ is independently selected from the group consisting of $C_1$–$C_6$alkyl, —OAryl, $C_3$–$C_{12}$Alicyclic, —O$C_1$–$C_6$alkyl, —S$C_1$–$C_6$alkyl and —C(O)$C_1$–$C_3$alkyl, wherein alkyl in each occurrence is linear or branched and is optionally substituted with 1–3 halogens, and Aryl is optionally substituted with 1–3 substituents independently selected from halogen, $CH_3$, $CF_3$, —$OCH_3$ and —$OCF_3$. Preferably, each $R^7$ is independently selected from F, Cl, $C_1$–$C_4$ alkyl, —O$C_1$–$C_4$ alkyl, —S$C_1$–$C_4$ alkyl, and —Ophenyl, wherein in each instance, alkyl is linear or branched and is optionally substituted with 1–5 F, and —Ophenyl is optionally substituted with 1–3 substituents independently selected from halogen, $CH_3$, $CF_3$, —$OCH_3$ and —$OCF_3$.

In preferred embodiments, $R^8$ is independently selected from halogen, $C_1$–$C_3$alkyl, and phenyl, wherein $C_1$–$C_3$alkyl is linear or branched and is optionally substituted with 1–3 halogens, and phenyl is optionally substituted with 1–3 substituents independently selected from halogen, $CH_3$, $CF_3$, —$OCH_3$ and —$OCF_3$. In preferred embodiments, $R^8$ is selected from $C_{1-5}$ alkyl, which is linear or branched and is optionally substituted with 1–3 F, and phenyl, which is optionally substituted with 1–3 substituents independently selected from halogen, $CH_3$, $CF_3$, —$OCH_3$ and —$OCF_3$.

In preferred embodiments, each $R^9$ is independently selected from $R^8$ and H.

In preferred embodiments, $Ar^1$ is generally phenyl, which is optionally substituted with 1–3 groups independently selected from $R^7$.

In a preferred set of compounds having formula Ia, the group -A-B—C— is selected from —C($R^9$)=N—O—, —C(=O)—N($R^9$)—O—, and —N($R^9$)—C(=O)—O—;

$R^1$ is selected from Cl, F and linear or branched $C_2$–$C_4$alkyl;

$R^2$ is linear or branched $C_2$–$C_4$alkyl;

$R^6$ is H;

Each $R^7$ is independently selected from F, Cl, $C_1$–$C_4$ alkyl, —$OC_1$–$C_4$ alkyl, —$SC_1$–$C_4$ alkyl, and —Ophenyl, wherein in each instance, alkyl is linear or branched and is optionally substituted with 1–5 F, and —Ophenyl is optionally substituted with 1–3 substituents independently selected from halogen, $CH_3$, $CF_3$, —$OCH_3$ and —$OCF_3$; and $R^8$ is selected from $C_{1-5}$ alkyl, which is linear or branched and is optionally substituted with 1–3F, and phenyl, which is optionally substituted with 1–3 substituents independently selected from halogen, $CH_3$, $CF_3$, —$OCH_3$ and —$OCF_3$.

A preferred subgroup of the compounds described above includes compounds having formula Ia in which $R^1$ is selected from Cl, F and n-$C_3$–$C_4$alkyl;

$R^2$ is n-$C_3$–$C_4$alkyl; and $Ar^1$ is phenyl, which is optionally substituted with 1–3 groups independently selected from $R^7$.

Specific examples of compounds of this invention are provided as Examples 1–30. Their structures are illustrated in the Table immediately before the

EXAMPLES

The compounds are listed by name below. The following compounds, including pharmaceutically acceptable salts and prodrugs of these compounds, are specific embodiments of this invention:

Example 1

α-[[5,7-dipropyl-3-(trifluoromethyl)-1,2-benzisoxazol-6-yl]oxy]benzeneacetic acid Example 2

α-[[5,7-dipropyl-3-(trifluoromethyl)-1,2-benzisoxazol-6-yl]oxy]4-chlorobenzeneacetic acid Example 3

α-[[5,7-dipropyl-3-(trifluoromethyl)-1,2-benzisoxazol-6-yl]oxy]4-[(trifluoromethyl)thio]benzeneacetic acid Example 4

α-[[5,7-dipropyl-3-(trifluoromethyl)-1,2-benzisoxazol-6-yl]oxy]4-(1-methylethyl)benzeneacetic acid Example 5

α-[[5,7-dipropyl-3-(trifluoromethyl)-1,2-benzisoxazol-6-yl]oxy]4-(2-methylpropyl)benzeneacetic acid Example 6

α-[[5,7-dipropyl-3-(trifluoromethyl)-1,2-benzisoxazol-6-yl]oxy]benzeneacetic acid Example 7

α-[[5-chloro-7-propyl-3-(trifluoromethyl)-1,2-benzisoxazol-6-yl]oxy]4-chlorobenzeneacetic acid Example 8

α-[[5-chloro-3-ethyl-7-propyl-1,2-benzisoxazol-6-yl]oxy]benzeneacetic acid

Example 9

α-[[5,7-dipropyl-3-phenyl-1,2-benzisoxazol-6-yl]oxy]benzeneacetic acid

Example 10

α-[[5-chloro-3-phenyl-7-propyl-1,2-benzisoxazol-6-yl]oxy]benzeneacetic acid

Example 11

α-[(2,3-dihydro-2-methyl-3-oxo-5,7-dipropyl-1,2-benzisoxazol-6-yl)oxy]4-(1-methylethyl)benzeneacetic acid Example 12

α-[(2,3-dihydro-3-(1-methylethyl)-2-oxo-5,7-dipropyl-1,3-benzoxazol-6-yl)oxy]4-(1-methylethyl)benzeneacetic acid Example 13

α-[3-hydroxy-4-(1-oxopropyl)-2,6-dipropylphenoxy]benzeneacetic acid

Example 14

α-[4-(1-oxopropyl)-2,6-dipropylphenoxy]benzeneacetic acid

Example 15

α-[4-(1-oxopropyl)-2,6-dipropylphenoxy]-4-(1-methylethyl)benzeneacetic acid

Example 16

α-[4-(1-oxopropyl)-2,6-dipropylphenoxy]-4-(1-methylethoxy)benzeneacetic acid

Example 17

α-[3-fluoro-4-(1-oxopropyl)-2,6-dipropylphenoxy]-4-(1-methylethyl)benzeneacetic acid

Example 18

α6-[phenyl(1H-tetrazol-5-yl)methoxyl-5,7-dipropyl-3-(trifluoromethyl)-1,2-benzisoxazole

Example 19

α6-[(4-chlorophenyl)(1H-tetrazol-5-yl)methoxy]-5,7-dipropyl-3-(trifluoromethyl)-1,2-benzisoxazole

Example 20

6-[[4-(1-methylethyl)phenyl](1H-tetrazol-5-yl)methoxyl-5,7-dipropyl-3-(trifluoromethyl)-1,2-benzisoxazole

Example 21

6-[(1H-tetrazol-5-yl)[4-(trifluoromethyl)phenyl]methoxy]-5,7-dipropyl-3-(trifluoromethyl)-1,2-benzisoxazole

Example 22

6-[[4-(2-methylpropyl)phenyl](1H-tetrazol-5-yl)methoxy]-5,7-dipropyl-3-(trifluoromethyl)-1,2-benzisoxazole

Example 23

6-[(4-ethylphenyl)(1H-tetrazol-5-yl)methoxy]-5,7-dipropyl-3-(trifluoromethyl)-1,2-benzisoxazole

Example 24

6-[(phenyl)(1H-tetrazol-5-yl)methoxy]-5,7-dipropyl-3-phenyl-1,2-benzisoxazole

Example 25

1-[4-[[4-(1-methylethyl)phenyl](1H-tetrazol-5-yl)methoxy]-3,5-dipropylphenyl]-1-propanone

Example 26

α-[[5,7-dipropyl-3-(trifluoromethyl)-1,2-benzisoxazol-6-yl]oxy]]-N-[(2,2,2-trifluoroethyl)sulfonyl]benzeneacetamide

Example 27

α-[[5,7-dipropyl-3-(trifluoromethyl)-1,2-benzisoxazol-6-yl]oxy]]-N-[propylsulfonyl]benzeneacetamide

Example 28

α-[[5,7-dipropyl-3-(trifluoromethyl)-1,2-benzisoxazol-6-yl]oxy]-3-thiopheneacetic acid

Example 29

α-[[5,7-dipropyl-3-(trifluoromethyl)-1,2-benzisoxazol-6-yl]oxy]-3-pyridineacetic acid

Example 30

α-[[5,7-dipropyl-3-(trifluoromethyl)-1,2-benzisoxazol-6-yl]oxy]4-[pyridin-2-ylmethoxy]benzeneacetic acid

Example 31

α-[4-(1-oxopropyl)-2,6-dipropylphenoxy]-3-pyridineacetic acid

Example 32

α-[5,7-dipropyl-3-(trifluoromethyl)-1,2-benzisoxazol-6-yl]oxy)-2-(2-phenyl-1,3-thiazol-4-yl)acetic acid; and

Example 33

α-[2,6-dipropyl-4-[2-(5-methyl-2-phenyl-1,3-oxazol-4-yl)ethoxy]phenoxy]-4-chlorobenzeneacetic acid The invention further includes pharmaceutical compositions comprising any of the compounds described herein and a pharmaceutically acceptable carrier.

The compounds as defined above are useful in treating, controlling, and preventing the following diseases, and may also be used in treating other diseases that are not listed below:

(1) a method for treating, controlling or preventing diabetes mellitus, and particularly non-insulin dependent diabetes mellitus, in a mammalian patient in need of such treatment which comprises administering to the patient a therapeutically effective amount of a compound of Formula I;

(2) a method for treating, controlling, or preventing hyperglycemia in a mammalian patient in need of such treatment which comprises administering to the patient a therapeutically effective amount of a compound of Formula I;

(3) a method for treating, controlling, or preventing lipid disorders, hyperlipidemia, or low HDL in a mammalian patient in need of such treatment which comprises administering to the patient a therapeutically effective amount of a compound of Formula I;

(4) a method for treating, controlling, or preventing obesity in a mammalian patient in need of such treatment which comprises administering to the patient a therapeutically effective amount of a compound of Formula I;

(5) a method for treating, controlling, or preventing hypercholesterolemia in a mammalian patient-in need of such treatment which comprises administering to the patient a therapeutically effective amount of a compound of Formula I;

(6) a method for treating, controlling, or preventing hypertriglyceridemia in a mammalian patient in need of such treatment which comprises administering to the patient a therapeutically effective amount of a compound of Formula I;

(7) a method for treating, controlling, or preventing dyslipidemia, including low HDL cholesterol, in a mammalian patient in need of such treatment which comprises administering to the patient a therapeutically effective amount of a compound of Formula I;

(8) a method for treating, controlling, or preventing atherosclerosis in a mammalian patient in need of such treatment which comprises administering to the patient a therapeutically effective amount of a compound of Formula I; it is understood that the sequellae of atherosclerosis (angina, claudication, heart attack, stroke, etc.) are thereby treated; and (9) a method for treating, controlling, or preventing cachexia in a mammalian patient in need of such treatment which comprises administering to the patient a therapeutically effective amount of a compound of Formula I.

Definitions

"Ac" is acetyl, which is $CH_3C(O)$—.

"Alkyl", as well as other groups having the prefix "alk", such as alkoxy or alkanoyl, means carbon chains which may be linear or branched or combinations thereof, unless the carbon chain is defined otherwise. Examples of alkyl groups include methyl, ethyl, propyl, isopropyl, butyl, sec- and tert-butyl, pentyl, neopentyl, hexyl, heptyl, octyl, nonyl, and the like.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means a saturated or partly saturated monocyclic or bicyclic carbocyclic ring system each having from 3 to 12 carbon atoms, unless otherwise defined. The term also can include a monocyclic ring fused to an aryl group or other ring system. Examples of cycloalkyl include cyclopropyl, cyclobutyl, cyclopentyl, cyclohexyl, cyclohexenyl, cycloheptyl, and the like.

"Aryl" (and "arylene") means mono- or bicyclic aromatic rings containing only carbon ring atoms. Aryl groups that are described herein are 6–10-membered monocyclic or bicyclic ring systems, and are preferably phenyl or naphthyl. Phenyl is most preferred. The term "aryl" also may describe an aryl group that is fused to a monocyclic cycloalkyl or monocyclic heterocyclic group. "Heterocycle" and "heterocyclic" means a fully or partially saturated monocyclic or bicyclic ring system containing at least one heteroatom selected from N, S and O in the ring, where the ring system has 4 to 11 atoms, except where defined otherwise. S may also have 1–2 O atoms bound to it that are not in the ring itself. Examples of aryl include phenyl and naphthyl, as well as the phenyl ring of indanyl, indenyl, and tetrahydronaphthyl. Examples of aryl fused to heterocyclic groups include 2,3-dihydrobenzofuranyl, dihydrobenzopyranyl, and the like. Examples of heterocycles include tetrahydrofuran, piperazine, tetrahydropyran, and morpholine.

"Heteroaryl" (and heteroarylene) means a mono- or bicyclic aromatic ring system containing 4–11 atoms in the ring or rings, including at least one ring heteroatom selected from N, O and S in the ring or rings (including SO and $SO_2$, where the O atoms are not in the ring). Heteroaryl also includes bicyclic aromatic rings having a heteroaromatic ring fused to a carbocyclic aromatic ring, such as benzene. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzisoxazolyl, benzoxazolyl, benzothiazolyl, benzimidazolyl, benzofuranyl, benzothiophenyl (including S-oxide and dioxide), furo(2,3-b)pyridyl, quinolyl, indolyl, isoquinolyl and the like.

Preferred monocyclic heteroaryls are comprised of 5–6 membered rings having 1–3 heteroatoms in the ring, where the heteroatoms are selected from N, O and S. There may also be additional heteroatoms that are not part of the ring structure but are attached to the ring, such as carbonyl oxygens and O atoms attached to S atoms in the ring. Examples include furan, pyrrole, thiophene (including S-oxide and dioxide), oxazole, isoxazole, thiazole, and pyridine. In a preferred subset of monocyclic heteroaryls, no more than one ring heteroatom is N.

Preferred bicyclic hetereoaryls comprise two fused rings having 9–10 atoms in the two rings, including 1–4 heteroatoms selected from N, O and S. There may also be additional heteroatoms that are not part of the ring structure but are attached to the ring, such as carbonyl oxygens and O atoms attached to S atoms in the ring. Examples include indole, benzofuran, benzothiophene (including S-oxide and dioxide), benzisoxazole, benzisothiazole, benzoxazole, benzisothiazole, benzopyran, furo(2,3-b)pyridine, quinoline, and isoquinoline. In a preferred subset of bicyclic heteroaryls, no more than one ring heteroatom is N.

"Halogen" includes fluorine, chlorine, bromine and iodine. Preferred halogens are chlorine and fluorine.

The term "composition," as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

In the description above and elsewhere, including the claims, when something is described as being "optional," such as one or more substituents or compounds from one or more lists of substituents or compounds, one of the options is that the substituent or compound may be absent.

Optical Isomers—Diastereomers—Geometric Isomers—Tautomers

Compounds of Formula I, Ia and Ib (written collectively in this section as I) contain at least one asymmetric center and may contain more than one asymmetric center. The compounds can thus occur as racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Some of the compounds described herein may exist with different points of attachment of hydrogen accompanied by one or more double bond shifts, referred to as tautomers. For example, a ketone and its enol form are keto-enol tautomers. The individual tautomers as well as mixtures thereof are encompassed with compounds of Formula I.

If desired, racemic mixtures of compounds of Formula I may be separated by the coupling of a racemic mixture of the compounds of Formula I to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds of Formula I can also be separated directly by chromatographic methods utilizing chiral stationary phases, which methods are well known in the art.

Alternatively, any enantiomer of a compound of the general Formula I may be obtained by stereoselective synthesis using optically pure starting materials or reagents of known configuration. Such methods are well known in the art.

Compounds of Formula I that have more than one asymmetric center and that occur as mixtures of diasteromers can similarly be separated into single diasteromers by standard methods, and these can be further separated to individual enantiomers as described above.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluene-sulfonic acid, and the like. Particularly preferred are citric, hydrobromic, hydrochloric, maleic, phosphoric, sulfuric, and tartaric acids.

It will be understood that, as used herein, references to the compounds of Formula I are meant to also include the pharmaceutically acceptable salts.

Metabolites—Prodrugs

Metabolites of the compounds of this invention that are therapeutically active and that are defined in the claims also are within the scope of the invention. Metabolites of other compounds not claimed in this invention, where the metabolites are therapeutically active and are defined in the claims also are within the scope of the invention. Prodrugs, which are compounds that are converted or metabolized to the claimed compounds as they are being administered to a patient or after they have been administered to a patient are also included within the scope of this invention. A non-limiting example of a prodrug of the carboxylic acids of this invention would be an ester of the carboxylic acid group, for example a $C_1$ to $C_6$ ester, which may be linear or branched, or more typically, an ester which has functionality that makes it more easily hydrolyzed or metabolized after administration to a patient.

Examples of prodrugs of this class of compounds may be described as compounds having the Formula Ib:

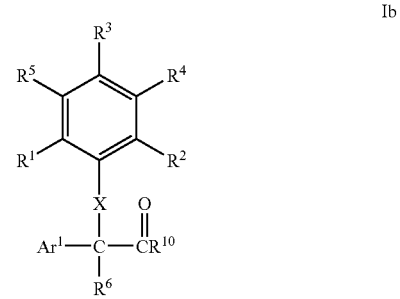

$R^1$, $R^2$, $R^3$, $R^4$, $R^5$, $R^6$, $R^7$, $R^8$, $R^9$, $Ar^1$, and X are as defined previously. In the prodrugs, $R^{10}$ is a group that is easily removed under physiological conditions during or after administration to a mammalian patient to yield a compound in which $R^{10}$ is —OH, or the carboxylate anion thereof (in solution), or a pharmaceutically acceptable salt thereof. This corresponds to compounds of Formula I in which Z is COOH, or the carboxylate anion thereof (in solution), or a pharmaceutically acceptable salt thereof.

Examples of prodrugs of Formula Ib include compounds in which $R^{10}$ is selected from the group consisting of —$OR^{11}$, —$OCH_2OR^{11}$, —$OCH(CH_3)OR^{11}$, —$OCH_2OC(O)R^{11}$, —$OCH(CH_3)OC(O)R^{11}$, —$OCH_2OC(O)OR^{11}$, —$OCH(CH_3)OC(O)OR^{11}$, and —$NR^{12}R^{12}$, where each $R^{11}$ is independently selected from $C_{1-6}$ alkyl optionally substituted with one or two groups selected from —$CO_2H$, —$CONH_2$, —$NH_2$, —OH, —OAc, —NHAc, and phenyl; and wherein each $R^{12}$ is independently selected from H and $R^{11}$. Compounds having Formula Ib, where $R^{10}$ has the chemical structure described above, are described herein as prodrugs. However, regardless of whether they are active as prodrugs, yielding compounds or salts of Formula I, or whether they have a different means of exhibiting pharmaceutical activity, the compounds of Formula Ib are included in this invention, regardless of the mechanism leading to their activity.

The description of utility, pharmaceutical compositions, combination therapies, administration, dosage, and the like that are described herein are applicable to the prodrugs described above and to the compounds described previously.

Utilities

Compounds of the present invention are potent agonists of varioius peroxisome proliferator activator receptor subtypes, particularly PPARα and/or PPARγ. Compounds of the present invention may be selective agonists of one receptor subtype, e.g. PPARγ or PPARα agonists, or they may be agonists of more than one receptor subtypes, e.g. dual PPARα/γ agonists. Compounds of the present invention are useful in treating, controlling or preventing diseases, disorders or conditions, wherein the treatment is mediated by the activation of an individual PPAR subtype (α or γ), or a combination of PPAR subtypes (e.g. α/γ). Thus one aspect of the present invention provides a method for the treatment, control or prevention of such diseases, disorders, or conditions in a mammal which comprises administering to such mammal a therapeutically effective amount of a compound of Formula I. The diseases, disorders or conditions for which compounds of the present invention are useful in treating, controlling or preventing include, but are not limited to, (1) diabetes mellitus, and especially non-insulin dependent diabetes mellitus (NIDDM), (2) hyperglycemia, (3) impaired glucose tolerance, (4) insulin resistance, (5) obesity, (6) lipid disorders, (7) dyslipidemia, (8) hyperlipidemia, (9) hypertriglyceridemia, (10) hypercholesterolemia, (11) low HDL levels, (12) high LDL levels, (13) atherosclerosis and its sequelae, (14) vascular restenosis, (15) irritable bowel syndrome, (16) inflammatory bowel disease, including Crohn's disease and ulcerative colitis, (17) other inflammatory conditions, (18) pancreatitis, (19) abdominal obesity, (20) neurodegenerative disease, (21) retinopathy, (22) neoplastic conditions, (23) adipose cell tumors, (24) adipose cell carcinomas, such as liposarcoma, (25) prostate cancer and other cancers, including gastric, breast, bladder and colon cancers, (26) angiogenesis, (27) Alzheimer's disease, (28) psoriasis, (29) acne vulgaris, (30) other skin diseases and dermatological conditions modulated by PPAR, (31) high blood pressure, (32) Syndrome X, (33) ovarian hyperandrogenism (polycystic ovarian syndrome), and other disorders where insulin resistance is a component.

Another aspect of the invention provides a method for the treatment, control, or prevention of hypercholesterolemia, atherosclerosis, low HDL levels, high LDL levels, hyperlipidemia, hypertriglyceridemia, and/or dyslipidemia, which comprises administering to a mammal in need of such treatment a therapeutically effective amount of an agonist of PPARα and/or PPARγ or a PPARα/γ dual agonist. The PPAR agonist may be used alone or advantageously may be administered with a cholesterol biosynthesis inhibitor, including but not limited to, an HMG-CoA reductase inhibitor such as lovastatin, simvastatin, pravastatin, fluvastatin, atorvastatin, rivastatin, itavastatin, or ZD-4522. The PPAR agonist may also be used advantageously in combination with other lipid lowering drugs such as cholesterol absorption inhibitors (for example stanol esters, sterol glycosides such as tiqueside, and azetidinones such as ezetimibe), ACAT inhibitors (such as avasimibe), and with niacin, bile acid sequestrants, microsomal triglyceride transport inhibitors, and bile acid reuptake inhibitors. These combination treatments may also be effective for the treatment, control or prevention of one or more related conditions selected from the group consisting of hypercholesterolemia, atherosclerosis, hyperlipidemia, hypertriglyceridemia, dyslipidemia, high LDL, and low HDL.

Another aspect of the invention provides a method of treating inflammatory conditions, including inflammatory bowel disease, Crohn's disease, and ulcerative colitis by administering an effective amount of a PPAR agonist, which may be a PPARα agonist, a PPARγ agonist, or a PPARα/γ dual agonist. Additional inflammatory diseases that may be treated with the instant invention include gout, rheumatoid arthritis, osteoarthritis, multiple sclerosis, asthma, ARDS, psoriasis, vasculitis, ischemia/reperfusion injury, frostbite, and related diseases.

Another aspect of the invention provides a method of treating cachexia. PPARα is known to be necessary for an appropriate energy sparing response to starvation, and inappropriate metabolism and energy utilization is clearly responsible for the wasting of cachexia.

Another aspect of the invention provides a method of treating a variety of skin diseases and dermatological conditions that are modulated by PPARα and/or γ agonists. These diseases and conditions include psoriasis and acne vulgaris. Examples of other skin diseases and dermatological disorders that may be treated include eczema; lupus associated skin lesions; dermatitides such as seborrheic dermatitis and solar dermatitis; keratoses such as seborrheic keratosis, senile keratosis, actinic keratosis, photo-induced keratosis, and keratosis follicularis; keloids and prophylaxis against keloid formation, warts inluding verruca, condyloma, or condyloma accuminatum, and human papilloma viral (HPV) infections such as venereal warts, viral warts, molluscum contagiosum, leukoplakia, lichen planus; keratitis, skin cancer such as basal cell carcinoma and cutaneous T cell lymphoma, and localized benign epidermal tumors (keratoderma, epidermal naevi).

Administration and Dose Ranges

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula I are administered orally.

The effective dosage of active ingredient employed may vary depending on the particular compound employed, the mode of administration, the condition being treated and the severity of the condition being treated. Such dosage may be ascertained readily by a person skilled in the art.

When treating or preventing diabetes mellitus and/or hyperglycemia or hypertriglyceridemia or other diseases for which compounds of Formula I or Ia are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams, preferably from about 1 milligrams to about 50 milligrams. In the case of a 70 kg adult human, the total daily dose will generally be from about 7 milligrams to about 350 milligrams. This dosage regimen may be adjusted to provide the optimal therapeutic response.

Pharmaceutical Compositions

Another aspect of the present invention provides pharmaceutical compositions which comprise a compound of Formula I and a pharmaceutically acceptable carrier. The pharmaceutical compositions of the present invention comprise a compound of Formula I or Ia or a pharmaceutically acceptable salt or prodrug thereof as an active ingredient, as well as a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula I may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Combination Therapy

Compounds of Formula I may be used in combination with other drugs that may also be useful in the treatment, prevention, suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy also includes therapies in which the compound of Formula I and one or more other drugs are administered on different overlapping schedules. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be administered in combination with a compound of Formula I, and either administered separately or in the same pharmaceutical composition, include, but are not limited to:

(a) insulin sensitizers including (i) PPARγ agonists such as the glitazones (e.g. troglitazone, pioglitazone, englitazone, MCC-555, rosiglitazone, and the like), and compounds disclosed in WO97/27857, 97/28115, 97/28137 and 97/27847; (ii) biguanides such as metformin and phenformin; (iii) protein tyrosine phosphatase-1B (PTP-1B) inhibitors, and (iv) dipeptidyl peptidase IV (DPP-IV) inhibitors;

(b) insulin or insulin mimetics;

(c) sulfonylureas such as tolbutamide and glipizide, or related materials;

(d) α-glucosidase inhibitors (such as acarbose);

(e) cholesterol lowering agents such as (i) HMG-CoA reductase inhibitors (lovastatin, simvastatin, pravastatin, fluvastatin, atorvastatin, rivastatin, itavastatin, ZD-4522 and other statins), (ii) sequestrants (cholestyramine, colestipol, and dialkylaminoalkyl derivatives of a cross-linked dextran), (iii) nicotinyl alcohol, nicotinic acid or a salt thereof, (iv) PPARα agonists such as fibric acid derivatives (clofibrate, fenofibrate and bezafibrate) or gemfibrozil, (v) PPARα/γ dual agonists, such as KRP-297, (vi) inhibitors of cholesterol absorption, such as for example ezetimibe, (vii) acyl CoA: cholesterol acyltransferase inhibitors, such as for example avasimibe, and (viii) anti-oxidants, such as probucol;

(f) PPARδ agonists such as those disclosed in WO97/28149;

(g) antiobesity compounds (anorectics) such as fenfluramine, dexfenfluramine, phentermine, sibutramine, mazindol, orlistat, lipase inhibitors, neuropeptide Y5 inhibitors, and $\beta_3$ adrenergic receptor agonists;

(h) an ileal bile acid transporter inhibitor; and (i) agents intended for use in inflammatory conditions such as aspirin, non-steroidal anti-inflammatory drugs, glucocorticoids, azulfidine, and cyclo-oxygenase 2 selective inhibitors.

The above combinations include combinations of a compound of the present invention not only with one other active compound, but also with two or more other active compounds. Non-limiting examples include combinations of compounds having Formula I with two or more active compounds selected from biguanides, sulfonylureas, HMG-CoA reductase inhibitors, other PPAR agonists, PTP-1B inhibitors, DPP-IV inhibitors, and anti-obesity compounds.

Biological Assays

A) PPAR Binding Assays

For preparation of recombinant human PPARγ, PPARδ, and PPARα: Human PPARγ$_2$, human PPARδ and human PPARα were expressed as gst-fusion proteins in *E. coli*. The full length human cDNA for PPARγ$_2$ was subcloned into the pGEX-2T expression vector (Pharmacia). The full length human cDNAs for PPARδ and PPARα were subcloned into the pGEX-KT expression vector (Pharmacia). *E. coli* containing the respective plasmids were propagated, induced, and harvested by centrifugation. The resuspended pellet was broken in a French press and debris was removed by centrifugation at 12,000×g. Recombinant human PPAR receptors were purified by affinity chromatography on glutathione sepharose. After application to the column, and one wash, receptor was eluted with glutathione. Glycerol (10%) was added to stabilize the receptor and aliquots were stored at −80° C.

For binding to PPARγ, an aliquot of receptor was incubated in TEGM (10 mM Tris, pH 7.2, 1 mM EDTA, 10% glycerol, 7 μL/100 mL β-mercaptoethanol, 10 mM Na molybdate, 1 mM dithiothreitol, 5 μg/mL aprotinin, 2 μg/mL leupeptin, 2 μg/mL benzamidine and 0.5 mM PMSF) containing 0.1% non-fat dry milk and 10 nM [$^3$H$_2$] AD5075, (21 Ci/mmole), ±test compound as described in Berger et al., Novel peroxisome proliferator-activated receptor (PPARγ) and PPARδ ligands produce distinct biological effects, J. Biol. Chem. (1999), 274, 6718–6725.) Assays were incubated for ~16 hr at 4° C. in a final volume of 150 μL. Unbound ligand was removed by incubation with 100 μL dextran/gelatin-coated charcoal, on ice, for ~10 min. After centrifugation at 3000 rpm for 10 min at 4° C., 50 μL of the supernatant fraction was counted in a Topcount.

For binding to PPARδ, an aliquot of receptor was incubated in TEGM (10 mM Tris, pH 7.2, 1 mM EDTA, 10% glycerol, 7 μL/100 mL β-mercaptoethanol, 10 mM Na molybdate, 1 mM dithiothreitol, 5 μg/mL aprotinin, 2 μg/mL leupeptin, 2 μg/mL benzamide and 0.5 mM PMSF) containing 0.1% non-fat dry milk and 2.5 nM [$^3$H$_2$]3-chloro-4-(3-(7-propyl-3-trifluoromethyl-6-benz-[4,5]-isoxazoloxy)propylthio)phenylacetic acid (17 Ci/mmole), ±test compound as described in Berger et al., Novel peroxisome proliferator-activated receptor (PPARγ) and PPARδ ligands produce distinct biological effects. J. Biol. Chem. (1999), 274, 6718–6725). [$^3$H$_2$]3-chloro-4-(3-(7-propyl-3-trifluoromethyl-6-benz-[4,5]-isoxazoloxy)propylthio)phenylacetic acid as a non-labelled compound is taught in Ex. 20 of WO 97/28137. Assays were incubated for ~16 hr at 4° C. in a final volume of 150 μL. Unbound ligand was removed by incubation with 100 μL dextran/gelatin-coated charcoal, on ice, for ~10 min. After centrifugation at 3000 rpm for 10 min at 4° C., 50 μL of the supernatant fraction was counted in a Topcount.

For binding to PPARα, an aliquot of receptor was incubated in TEGM (10 mM Tris, pH 7.2, 1 mM EDTA, 10% glycerol, 7 μL/100 mL β-mercaptoethanol, 10 mM Na molybdate, 1 mM dithiothreitol, 5 μg/mL aprotinin, 2 μg/mL leupeptin, 2 μg/mL benzamide and 0.5 mM PMSF) containing 0.1% non-fat dry milk and 5.0 nM [3H$_2$](3-(4-(3-phenyl-7-propyl-6-benz-[4,5]-isoxazoloxy)butyloxy))phenylacetic acid (34 Ci/mmole), ±test compound. This is a tritium labelled variant of Ex.62 in WO 97/28137. Assays were incubated for ~16 hr at 4° C. in a final volume of 150 μL. Unbound ligand was removed by incubation with 100 μL dextran/gelatin-coated charcoal, on ice, for ~10 min. After centrifugation at 3000 rpm for 10 min at 4° C., 50 μL of the supernatant fraction was counted in a Topcount.

B). Gal-4 hPPAR Transactivation Assays

The chimeric receptor expression constructs, pcDNA3-hPPARγ/GAL4, pcDNA3-hPPARδ/GAL4, pcDNA3-hPPARα/GAL4 were prepared by inserting the yeast GAL4 transcription factor DBD adjacent to the ligand binding domains (LBDs) of hPPARγ, hPPARδ, hPPARα, respectively. The reporter construct, pUAS(5×)-tk-luc was generated by inserting 5 copies of the GAL4 response element upstream of the herpes virus minimal thymidine kinase promoter and the luciferase reporter gene. pCMV-lacZ contains the galactosidase Z gene under the regulation of the cytomegalovirus promoter. COS-1 cells were seeded at 12×10$^3$ cells/well in 96 well cell culture plates in high glucose Dulbecco's modified Eagle medium (DMEM) containing 10% charcoal stripped fetal calf serum (Gemini Bio-Products, Calabasas, Calif.), nonessential amino acids, 100 units/ml Penicillin G and 100 mg/ml Streptomycin sulfate at 37° C. in a humidified atmosphere of 10% CO$_2$. After 24 h, transfections were performed with Lipofectamine (GIBCO BRL, Gaithersburg, Md.) according to the instructions of the manufacturer. Briefly, transfection mixes for each well contained 0.48 μl of Lipofectamine, 0.00075 μg of pcDNA3-PPAR/GAL4 expression vector, 0.045 μg of pUAS(5×)-tk-luc reporter vector and 0.0002 μg of pCMV-lacZ as an internal control for transactivation efficiency. Cells were incubated in the transfection mixture for 5 h at 37° C. in an atmosphere of 10% CO$_2$. The cells were then incubated for ~48 h in fresh high glucose DMEM containing 5% charcoal stripped fetal calf serum, nonessential amino acids, 100 units/ml Penicillin G and 100 mg/ml Streptomycin sulfate±increasing concentrations of test compound. Since the compounds were solubilized in DMSO, control cells were incubated with equivalent concentrations of DMSO; final DMSO concentrations were ≦0.1%, a concentration which was shown not to effect transactivation activity. Cell lysates were produced using Reporter Lysis Buffer (Promega, Madison, Wis.) according to the manufacturer's instructions. Luciferase activity in cell extracts was determined using Luciferase Assay Buffer (Promega, Madison, Wis.) in an ML3000 luminometer (Dynatech Laboratories, Chantilly, Va.). β-galactosidase activity was determined using β-D-galactopyranoside (Calbiochem, San Diego, Calif.).

C. In vivo Studies

Male db/db mice (10–11 week old C57B1/KFJ, Jackson Labs, Bar Harbor, Me.) were housed 5/cage and allowed ad lib. access to ground Purina rodent chow and water. The animals, and their food, were weighed every 2 days and were dosed daily by gavage with vehicle (0.5% carboxymethylcellulose)±test compound at the indicated dose. Drug suspensions were prepared daily. Plasma glucose, and triglyceride concentrations were determined from blood obtained by tail bleeds at 3–5 day intervals during the study period. Glucose, and triglyceride, determinations were performed on a Boehringer Mannheim Hitachi 911 automatic analyzer (Boehringer Mannheim, Indianapolis, Ind.) using heparinized plasma diluted 1:6 (v/v) with normal saline. Lean animals were age-matched heterozygous mice maintained in the same manner.

Table of Compounds

The table below illustrates compounds that were synthesized in accordance with the present invention. Detailed syntheses are provided in the Examples.

Example 1

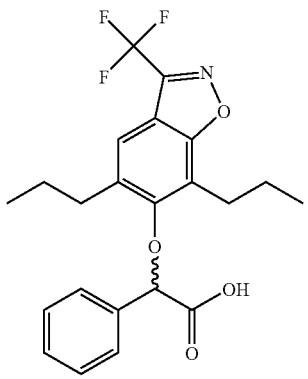

Example 2

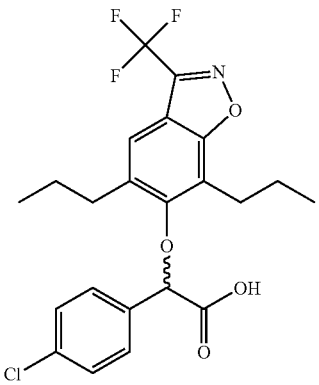

Example 3

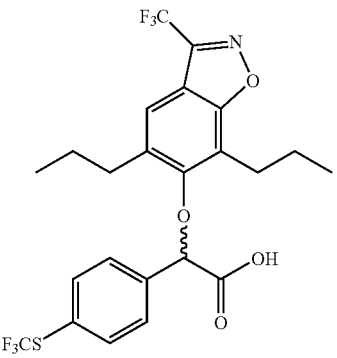

Example 4

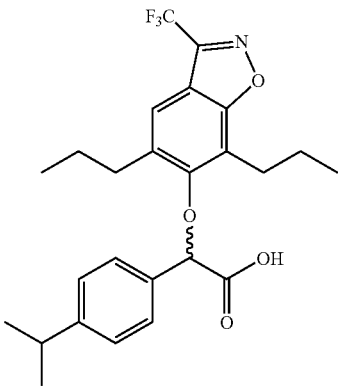

Example 5

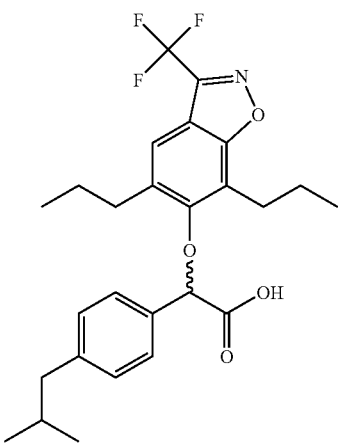

Example 6

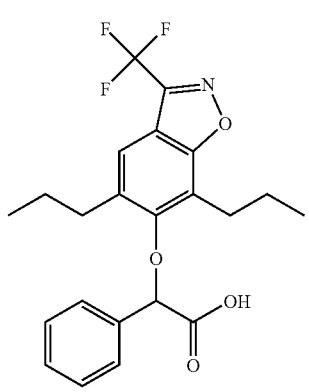

-continued
Example 7
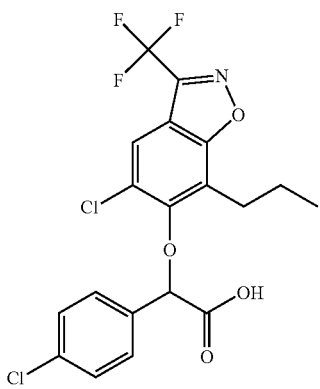
Example 8
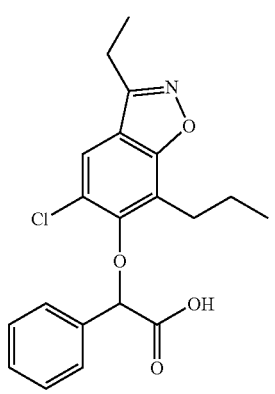
Example 9
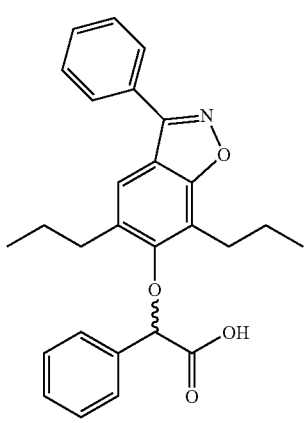
Example 10
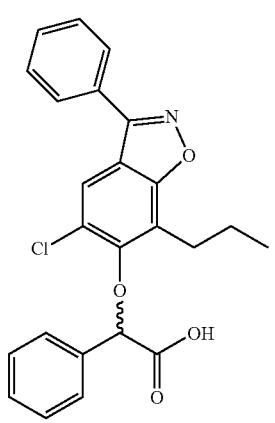
-continued
Example 11
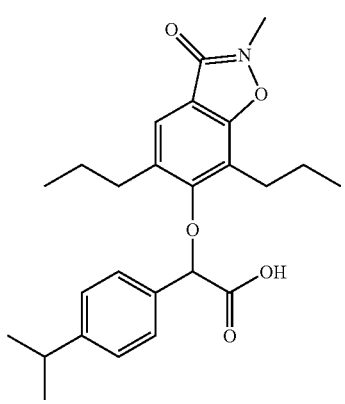
Example 12
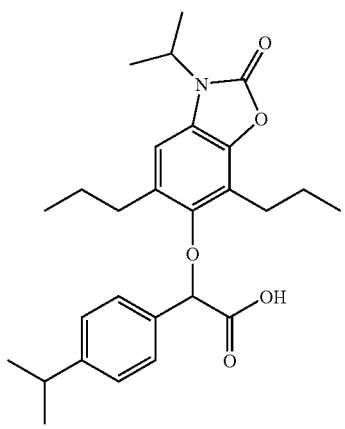
Example 13
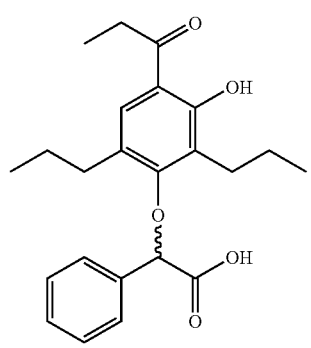
Example 14
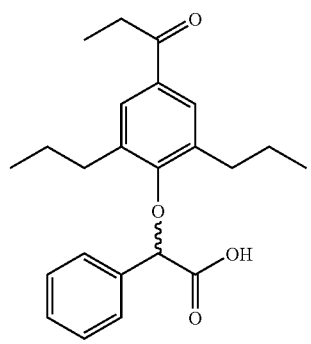

-continued
Example 15
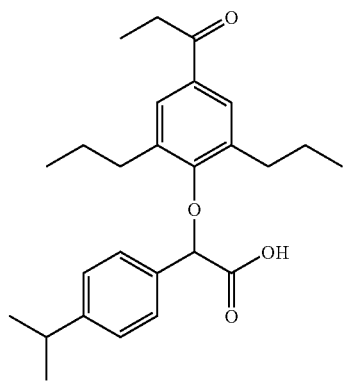
Example 16
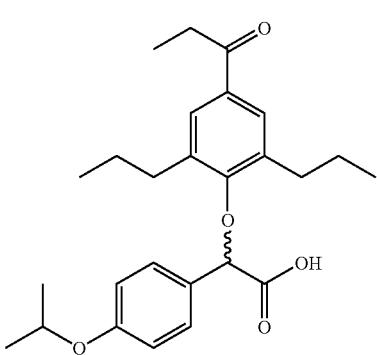
Example 17
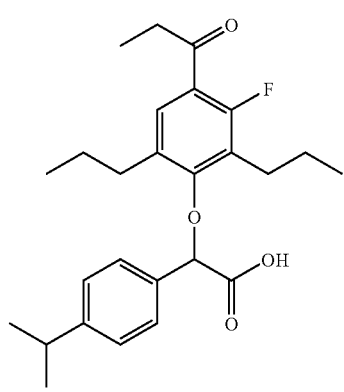
Example 18
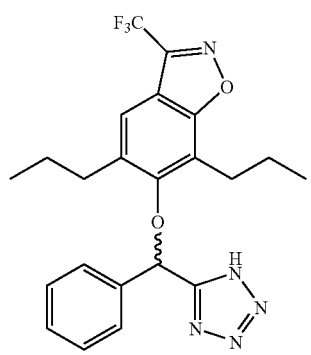
-continued
Example 19
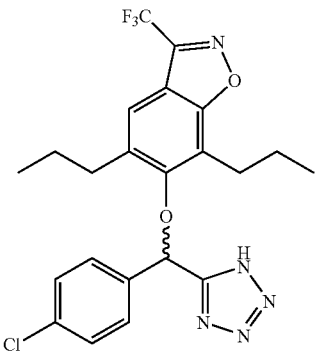
Example 20
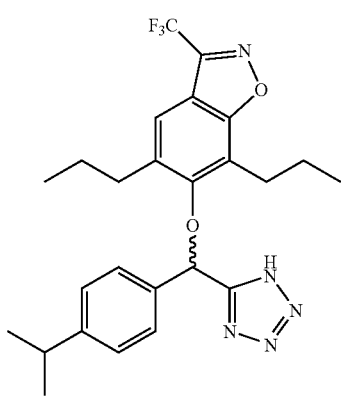
Example 21
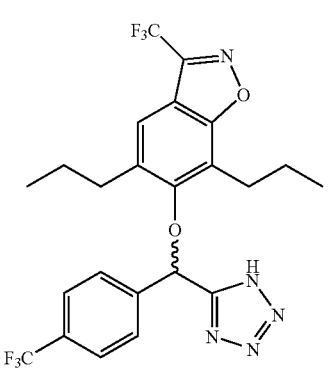
Example 22
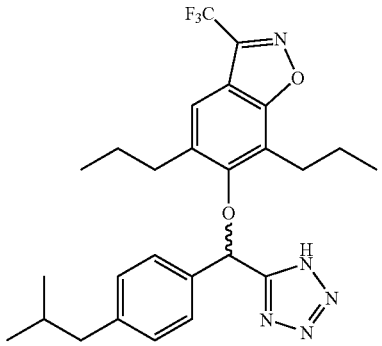

-continued
Example 23
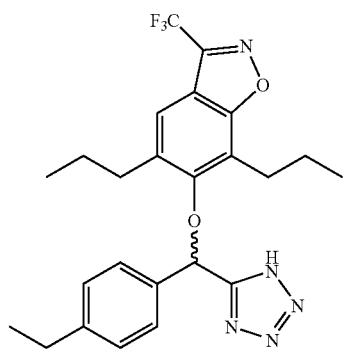
Example 24
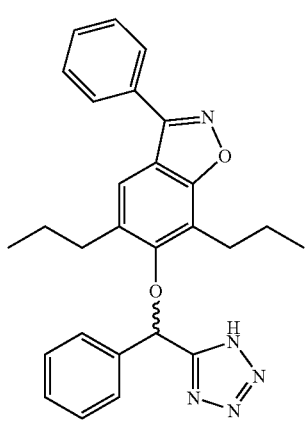
Example 25
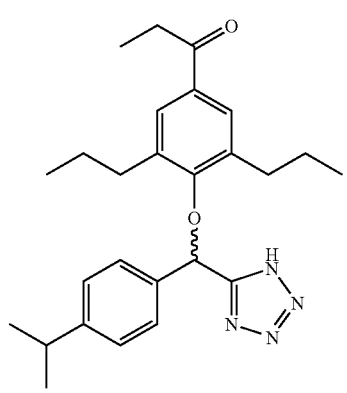
Example 26
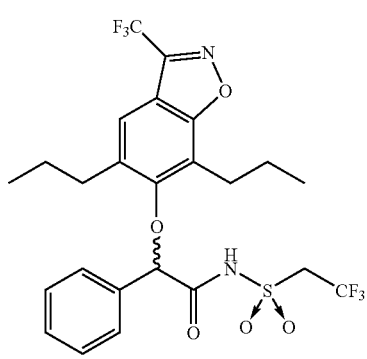
-continued
Example 27
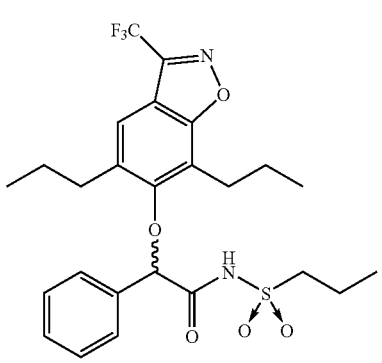
Example 28
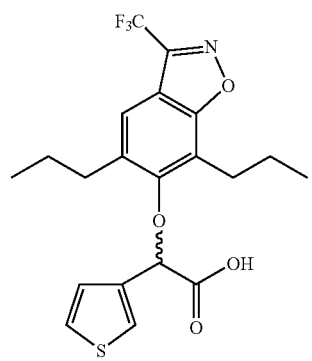
Example 29
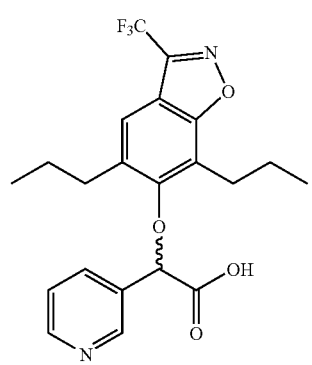

Example 30

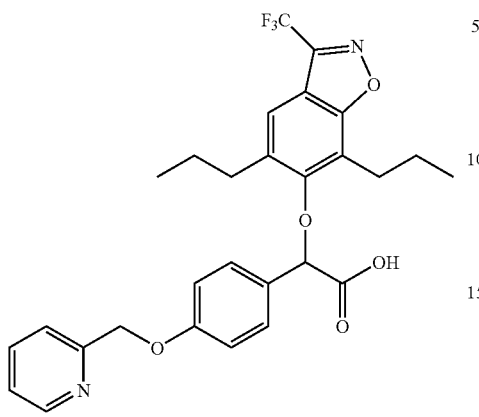

Example 31

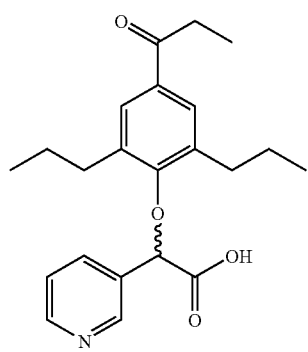

Example 32

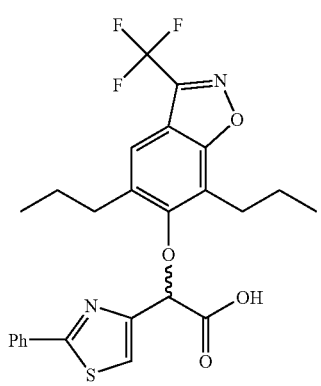

Example 33

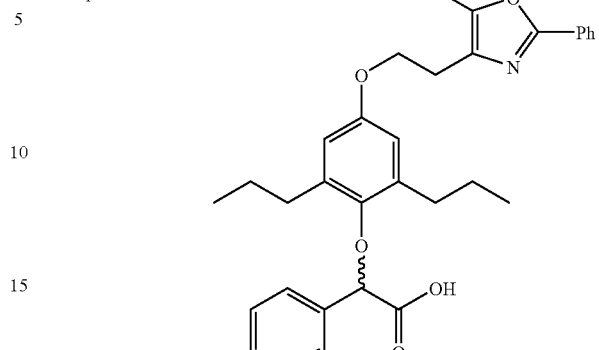

Synthetic Methods

Processes that are used in making compounds of the instant invention are described in general terms below. Syntheses of specific compounds are provided in the Examples section.

Electrophilic Partner

Typical processes for the preparation of the compounds of interest are shown in the figures below. One particularly versatile preparative route to racemic 2-(aryloxy)-2-arylacetic acids is the coupling of a phenol and an electrophilic arylacetic acid derivative. Electrophilic phenylacetic acid derivatives are readily available from either the parent arylacetic acids by deprotonation and quenching with a halogen source such as N-bromosuccinimde or by bromination of the corresponding 2-aryl(2-hydroxy)acetic acid. In some cases the intermediate 2-aryl(2-hydroxy)acetic acid is easily prepared from the Friedel Crafts acylation of an aryl residue with ethyl oxalyl chloride followed by ketone reduction. Subsequent halogenation yields the necessary 2-bromo phenylacetic acid as in the illustrated example derived from cumene.

Preparation of the required arylacetic acids, mandelic acids and other substrates is readily done by practitioners in the field of synthetic organic chemistry.

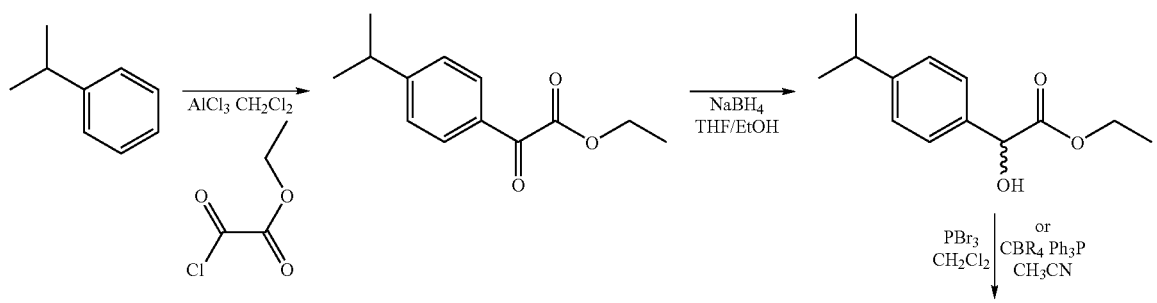

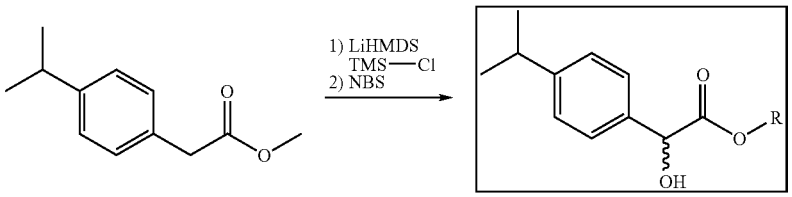

For cases where the preparation of the single enantiomer of a 2-(aryloxy)-2-arylacetic acid is desired, an electrophilic partner incorporating a lactamide chiral auxiliary is used. Two procedures for the facile preparation of the desired electrophile are either by coupling of the appropriate (R) or (S) pyrrolidine lactamide with a racemic 2-haloarylacetic acid or by a route similar to the Friedel Crafts acylation reported above. The detailed chemistry of this diastereoselective condensation is described in Paul F. Devine, et alii *Tet Let* 37(16), 2683–2686, 1996. Preparation of typical mandelate lactamide esters are also described there.

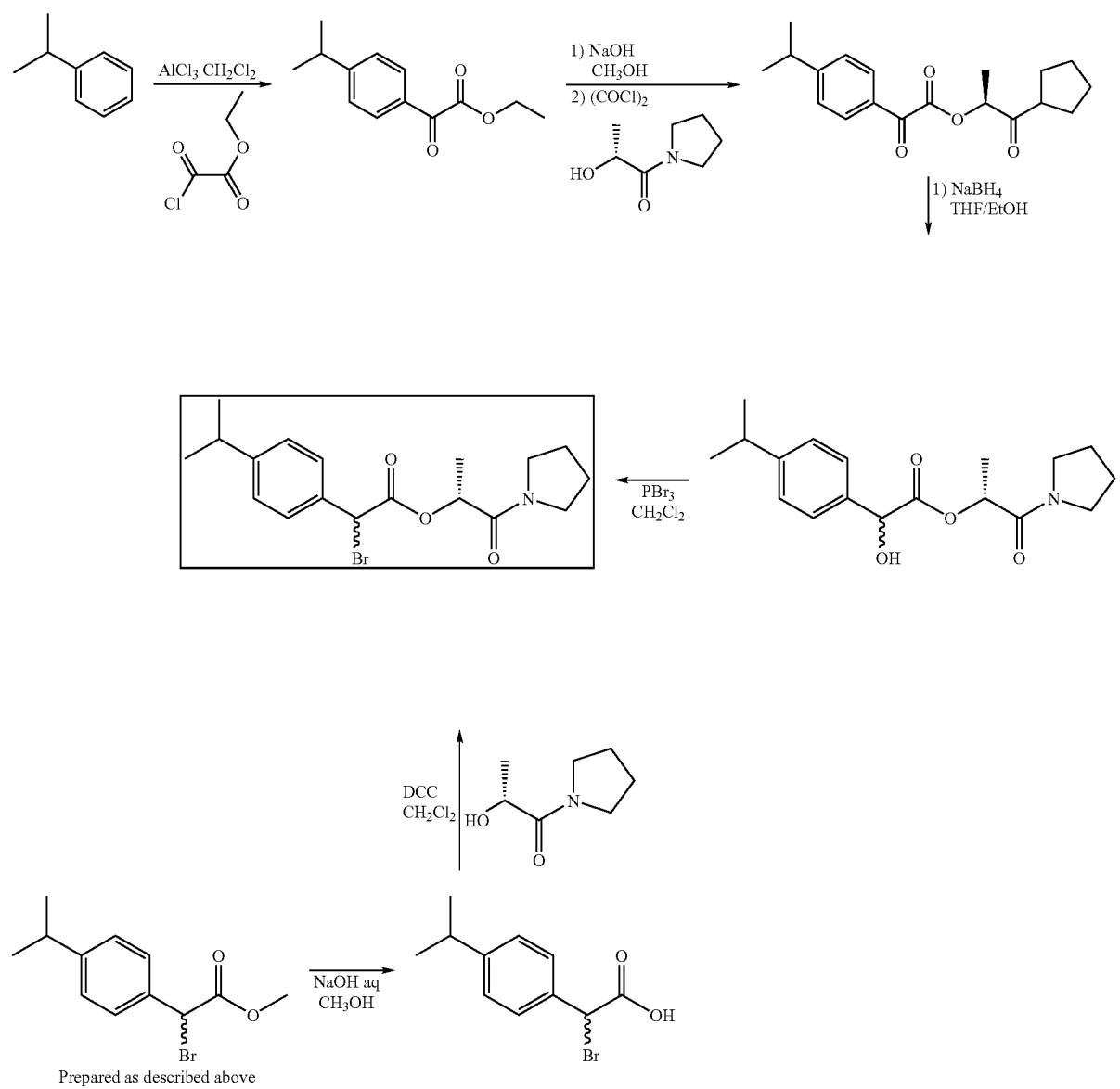

Several alternative synthetic routes to this class of compounds have been described in the literature. For examples see *Chirality* 11, 482–486, 1999 for a route to enantiomerically enriched products, and *Chirality* 9, 37–47, 1997 for Mitsunobu displacements leading to racemic compounds.

Synthesis of Phenol Fragments

The phenol partners for the desired compounds are generally avilable through standard transformations of commercially available phenols or resorcinols. Typical examples are shown below for ketoresorcinol, ketophenol and benzisoxazole classes.

then allowed to proceed to completion at −20° C. to 0° C. Isolation of the products uses standard methods.

Cleavage of the ester yields the desired acid product. Racemic examples are cleaved in basic alcohol or basic aqueous mixed solvents by standard means. Due to a proclivity towards base induced racemization, the lactamide auxiliaries are cleaved by standard methods using LiOOH.

The enantiomeric excess of the final product is typically determined using any of several commercially available chiral stationary phase HPLC columns.

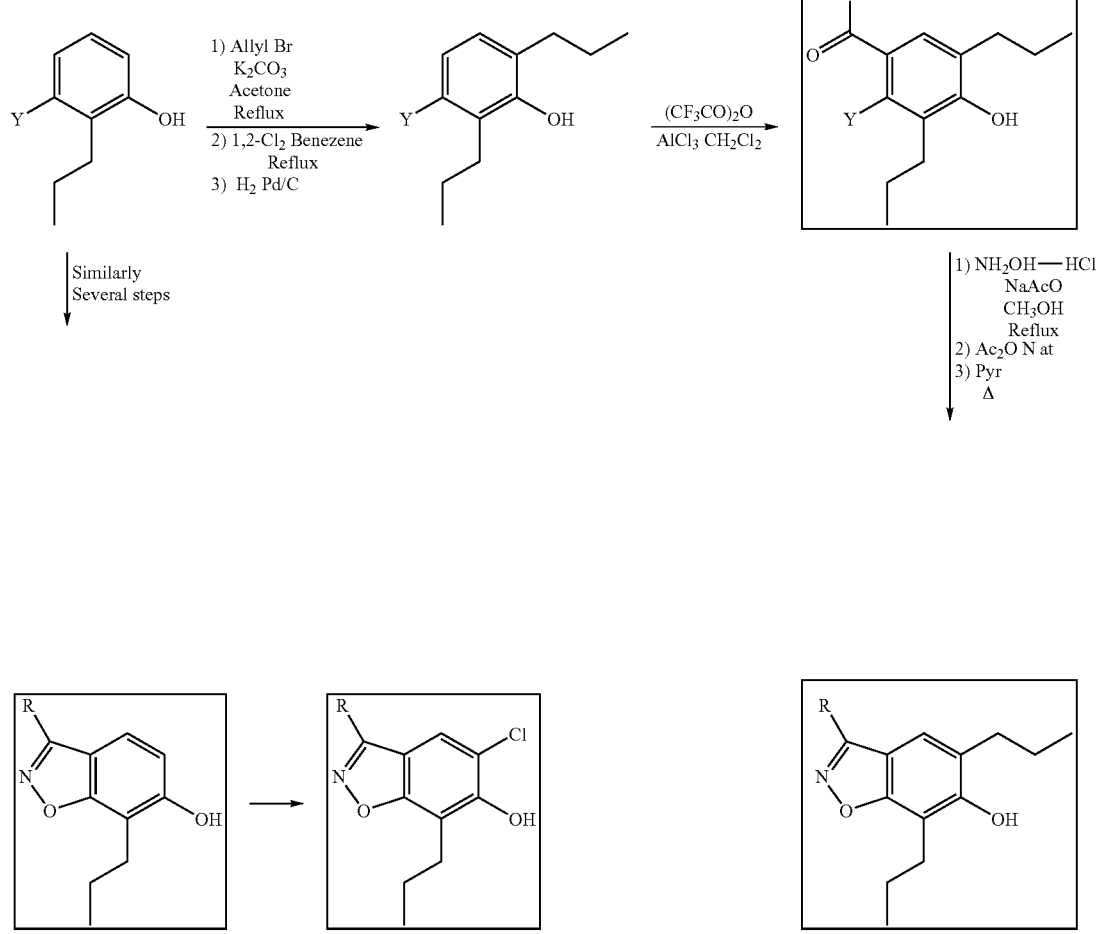

Coupling and hydrolysis to a 2-(aryloxy)-2-arylacetic acids

The 2-(aryloxy)-2-arylacetic acids are prepared from the above partners by coupling in the presence of base. For racemic examples the partners are coupled using a base in a polar solvent such as $Cs_2CO_3$ in DMF or $K_2CO_3$ in acetone. Couplings in acetone may require heating. For the diastereoselective coupling of the lactamide esters, phenolic partners are deprotonated with a lithium alkoxide base in aprotic solvent and added to the bromide partner in ThF at low temperature, typically −30° to −40° C. Most couplings are

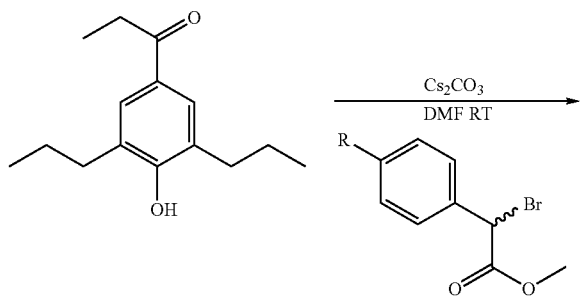

-continued

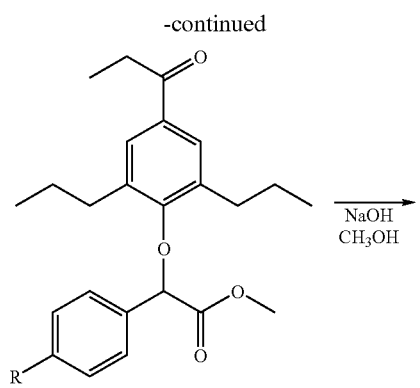

NaOH
CH₃OH
→

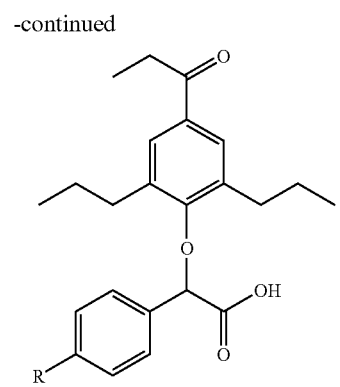

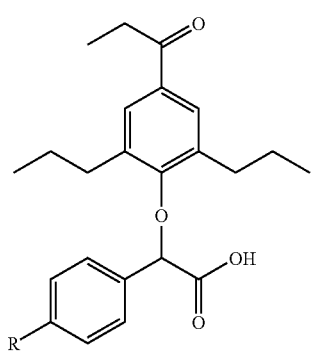

1) LiOtBu
2) Addition to

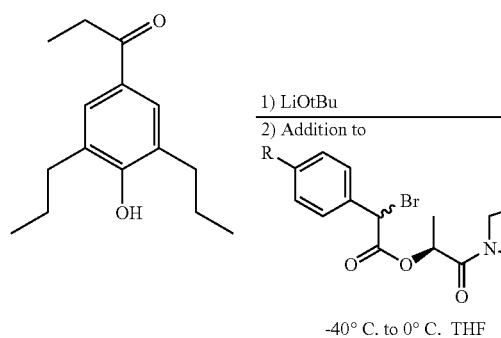

-40° C. to 0° C. THF

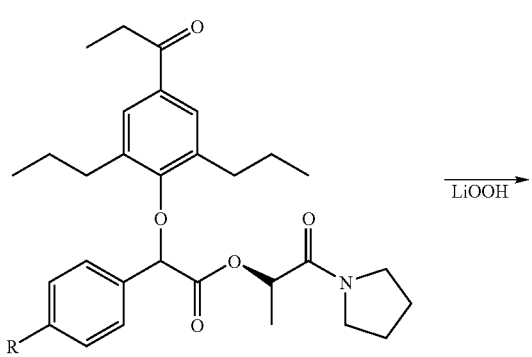

LiOOH
→

Alternate Non-basic Condensation

An alternate coupling protocol for the same type of partners involves the insertion of the acidic phenol into a diazo intermediate. The alpha-diazo intermediates are readily prepared by known methods from either arylacetic acids (Villalgordo, J. M.; Enderli, A.; Linden, A.; Heimgartner, H.; *Helv Chim Acta* 1995, 78 (8), 1983–1998) or alpha-keto acids (Shi, G.; Cai, W.; *J Chem Soc, Perkin Trans 1* 1996, (19), 2337–2338).

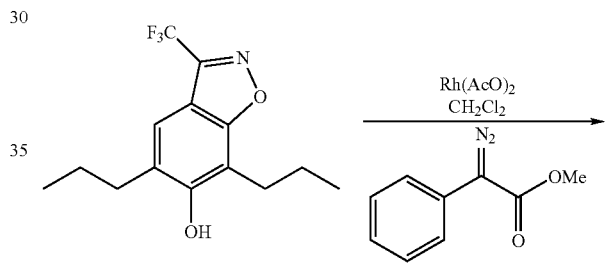

Rh(AcO)₂
CH₂Cl₂
→

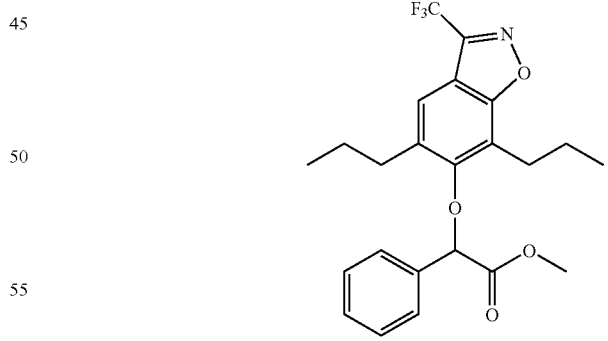

Tetrazole Synthesis

The tetrazole analogs of the 2-(aryloxy)-2-arylacetic acids are accessible by any of several standard conversions of the final acids or appropriately protected intermediates to nitriles and then to tetrazoles. The following example is typical of conditions used.

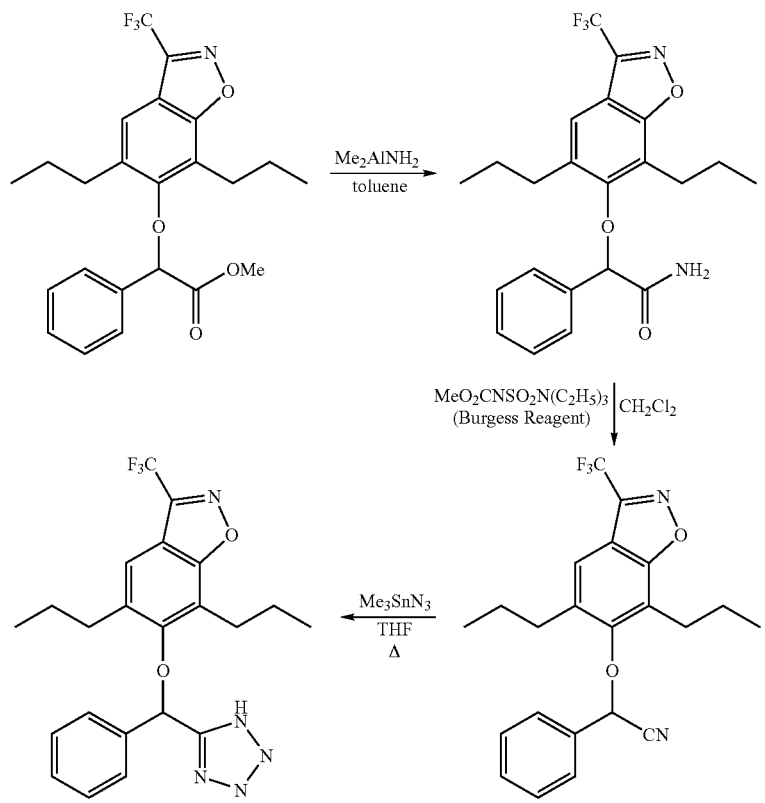

Acyl Sulfonamides

The acyl sulfonamides were prepared from the carboxylic acids by standard procedures. For the example given, an activated carboxylate was coupled with a sulfonamide in the presence of base to give the desired acid surrogate.

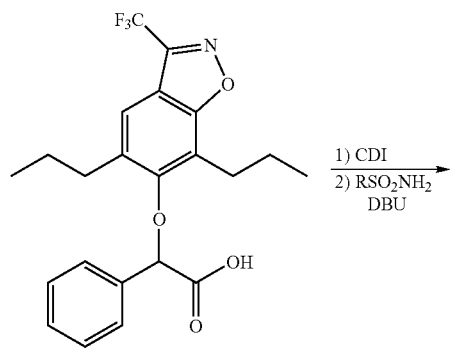

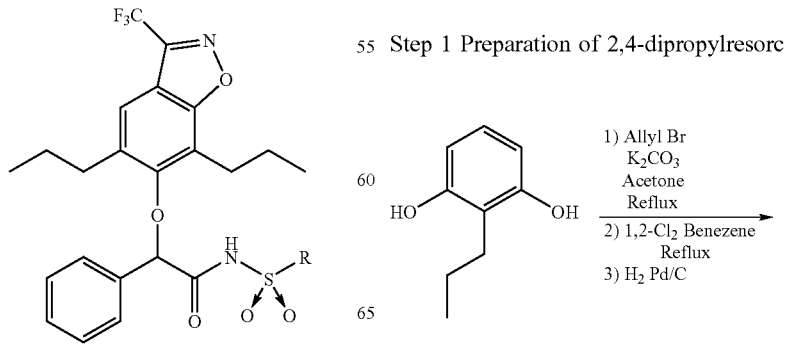

EXAMPLES

The following Examples are provided to illustrate the invention, including methods used to make the compounds, and are not to be construed as limiting the invention in any manner. The scope of the invention is defined in the appended claims.

EXAMPLES

The following Examples are provided to illustrate the invention, including methods of making the compounds of the invention, and are not to be construed as limiting the invention in any manner.

Example 1

Step 1 Preparation of 2,4-dipropylresorcinol

-continued

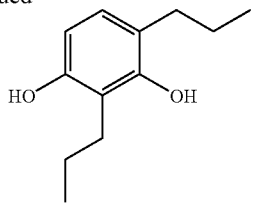

Commercially available 2-propylresorcinol (55 gm) was dissolved in acetone (650 ml). Allyl Bromide (100 ml) and K$_2$CO$_3$ (152 Gm) were added. The mixture was stirred briefly at RT followed by heating under reflux. Additional allyl bromide (20 ml) was added at 3.5 Hrs. Heating was stopped at 8 Hrs. The cooled mixture was filtered and the cake washed with acetone. The acetone filtrate was diluted with ethyl ether (1L), washed with brine and dried over MgSO$_4$. The organic extracts were reduced i. vac. The crude allyl ether was used in the following step.

The allyl ether (0.5 mol) was dissoved in ortho-dichlorobenzene (500 ml) and the reaction vessel purged with nitrogen. The mixture was heated under reflux 24 Hrs followed by cooling to RT. The reaction mixture was diluted with hexanes (1L) and extracted twice with 2 N NaOH (500 ml). The aqueous phase was washed twice with ether and washes discarded. The aqueous phase was acidified with 2N HCl and extracted three times with ether. Combined ether extracts from the acidified aqueous phase were washed with brine and dried over MgSO$_4$. Extracts were reduced in vac. The product was purified by elution from a silica gel column (1.5 Kilo E. Merck 40–63 µ) with 3L 1:1 CH$_2$Cl$_2$:Hexanes, 5L 3:1 CH$_2$Cl$_2$:Hexanes and 100% CH$_2$Cl$_2$.

The product 2,6-bis-allylresorcinol (33.5 gm) was dissolved in methanol and hydrogenated under H$_2$ Pressure (initial pressure 45 psig) over 10% Pd on carbon (300 mg). The reaction mixture was filtered through celite and reduced i. vac. The crude oil was flushed through a short SiO$_2$ gel column eluting with ethyl ether. The resulting oil was purified by crystallization from hexanes:ether.

Step 2 Preparation of 2,4-dihydroxy-3,5-dipropyl-1',1',1'-trifluoroacetophenone

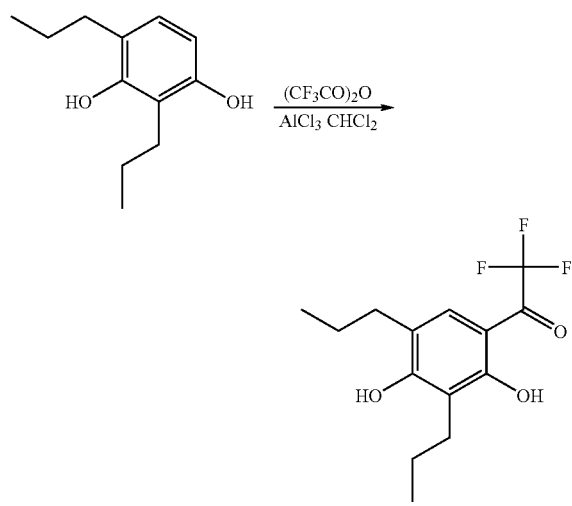

A mixture of 2,6-dipropylresorcinol (3.28 grams) with aluminum chloride (8.56 grams) in dichloromethane (100.0 mL) was cooled to 0° C. Trifluoroacetic anhydride (3.96 mL) was added dropwise over 30 minutes. This mixture was allowed to warm to RT and stirred overnight. The reaction mixture was partitioned between methylene choride and water. The organic phase was dried over sodium sulfate and filtered. The solvent was evaporated and the resulting solid was chromatographed on silica gel using ethyl acetate and hexane (4:96) to give the titled compound.

NMR (CDCl$_3$) σ7.45 (brd m, 1H), 5.65 (s, 1H), 2.66 (collapsed dd, J=7.6 Hz, 2H), 2.56 (collapsed dd, J=7.6 Hz, 2H), 1.65 (m, 4H), 1.01 (t, J=7.4 Hz, 3H), 1.00 (t, J=7.4 Hz, 3H).

MS ESI 291 M+1.

Step 3 Preparation of 5,7-dipropyl-6-hydroxy-3-trifluoromethyl-1,2-benzisoxazole

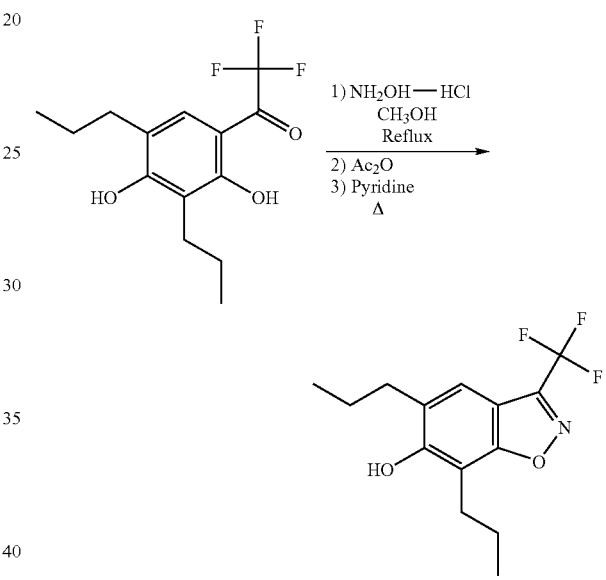

A mixture of 2,4-dihydroxy-3,5-dipropyl-1',1',1'-trifluoroacetophenone(1.0 gram), sodium acetate (3.53 grams), hydroxylamine hydrochloride (2.63 grams) and methanol (20 mL) was refluxed overnight. The solvent was then evaporated and the resulting solid was partitioned between ethyl acetate and water. The organic phase was separated and washed with brine. The organic phase was dried over sodium sulfate and the solvent was evaporated to give an oil. The resulting oil was chromatographed on silica gel using ethyl acetate and hexane (4:96) to give the indicated oxime. The oil was then dissolved in acetic anhydride (4 ml). The solution was stirred for six hours, then the acetic anhydride was evaporated in vac. to give an oil. This was dissolved in pyridine and refluxed 3 Hrs. The pyridine was removed in vac. and the resulting paste partitioned between ethyl acetate and 1 N HCl. The organic phase was seperated and washed with brine. The organic phase was dried over sodium sulfate and the solvent was evaporated to give an oil. The resulting oil was chromatographed on silica gel using ethyl acetate and hexane (3:97) to give the indicated benzisoxazole.

NMR (CDCl$_3$) σ7.37 (brd m, 1H), 5.33 (s, 1H), 2.93 (collapsed dd, J=7.6 Hz, 2H), 2.71 (collapsed dd, J=7.7 Hz, 2H), 1.73 (m, 4H), 1.033 (t, J=7.4 Hz, 3H), 1.025 (t, J=7.4 Hz, 3H).

MS ESI 288.3 M+1.

Step 4 Preparation of Methyl α-[[5,7-dipropyl-3-(trifluoromethyl)-1,2-benzisoxazol-6-yl]oxy]benzeneacetate.

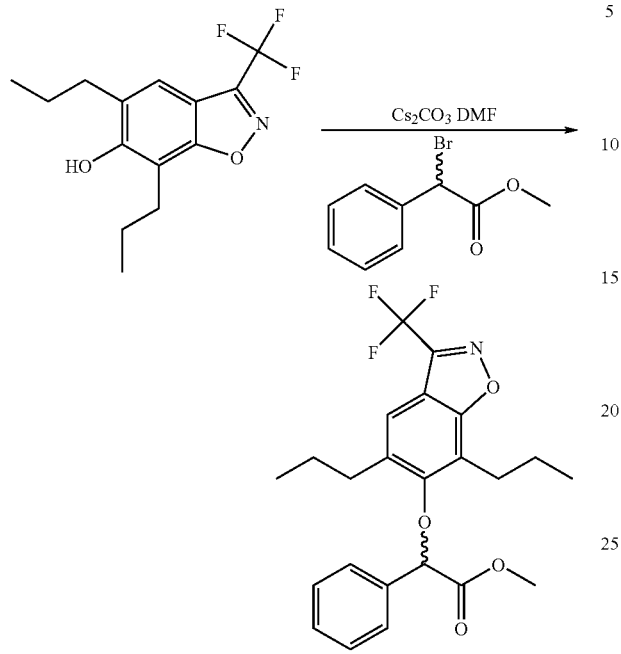

Methyl 2-bromo-2-phenylacetate (9.16 gm 1.05 eq), Cs$_2$CO$_3$ (10.03 grams, 1.05 eq) and the indicated benzisoxazole (10.93 grams, 1.0 eq) were combined in 100 ml DMF at room temperature. The mixture was stirred 19 Hrs. The suspension was poured into 1 L 1 N HCl and extracted with ethyl acetate. The organic phase was separated and washed with water followed by brine. The organic phase was dried over sodium sulfate and the solvent was evaporated to give an oil. The resulting oil was chromatographed on silica gel using ethyl acetate and hexanes (4:96) to give the titled compound.

Characteristic NMR Resonances; $^1$H NMR 400 MHz (CDCl$_3$); 7.51–7.53 (m, 2H), 7.41–7.45 (m, 4H), 5.26 (s, 1H), 3.78 (s, 3H), 2.73 (m, 2H), 2.55 (m, 2H), 1.5–1.7 (m, 4H), 0.884 (t, 3H, J=7.4 Hz), 0.877 (t, 3H, J=7.4 Hz).

Step 5 Preparation of α-[[5,7-dipropyl-3-(trifluoromethyl)-1,2-benzisoxazol-6-yl]oxy]benzeneacetic acid.

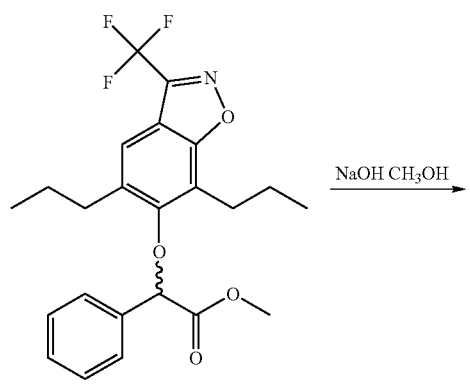

—continued

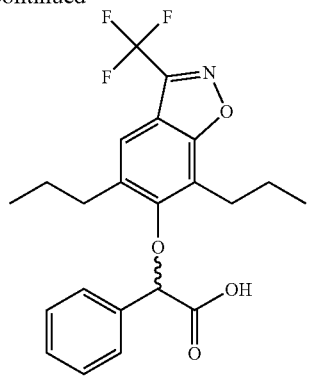

The ester (15 grams, 1.0 Eq) was dissolved in 90% methanol water (300 ml). Approximately 10% (vol/vol) THF was added. Aqueous NaOH (1.02 M, 38 ml) was added. The mixture was left to stand 5 Hrs. Solvent volume was reduced by approximately 50% in vac. and the resulting solution acidified to pH 2 with 1 N HCl. The mixture was extracted with ethyl acetate. The organic phase was separated and washed with water followed by brine. The organic phase was dried over sodium sulfate and the solvent was evaporated to give an oil. The resulting oil was crystallized from hexanes to give the titled compound.

Characteristic NMR Resonances; $^1$H NMR 400 MHz (CDCl$_3$); 7.41–7.53 (m, 6H), 2.71 (m, 2H), 2.53 (m, 2H), 1.5–1.7 (m, 4H), 0.862 (t, 3H, J=7.4 Hz).

Example 2

Step, 1 Preparation of Methyl 2-Bromo-2-(4-chlorophenyl)acetate

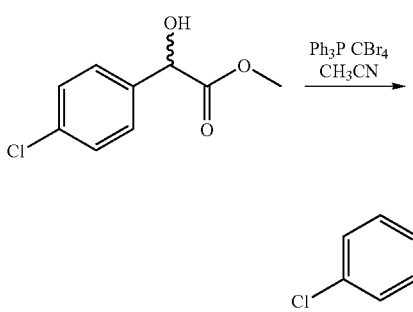

Commercially available 4-Cl mandelic acid was esterified with methanol and catalytic sulfuric acid. The crude ester (10 gm, 1.0 eq) was dissoved in acetonitrile (75 ml) with triphenylphosphine (15.7 gm, 1.2 eq) and cooled to 0° C. Solid CBr$_4$ (19.9 gm, 1.2 eq) was added over approximately 5 mins. The solution was stirred 5 minutes at 0° C. and allowed to warm to RT. The reaction mixture was loaded directly onto a SiO$_2$ (1 kg) column for purification. The title compound was eluted with hexanes and ethyl acetate (97:3).

Characteristic NMR Resonances; $^1$H NMR 400 MHz (CDCl$_3$); 7.45 (aromatic ABq, 4H, J=8.6 Hz, Δσ=57.8 Hz), 5.33 (s, 1H), 3.81 (s, 3H).

Step 2 Preparation of Methyl α-[[5,7-dipropyl-3-(trifluoromethyl)-1,2-benzisoxazol-6-yl]oxy]-4-chlorobenzeneacetate.

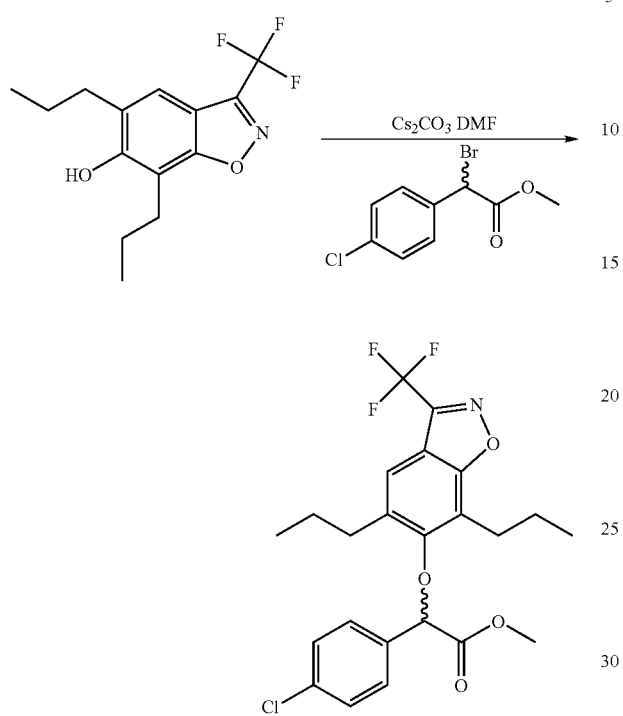

The title ester was prepared as was described for example 1, step 4 from the indicated bromide (10.7 gm, 1.05 eq) and phenol (11.2 gm, 1.0 eq). The resulting solid was purified by chromatography on silica gel using ethyl acetate and hexane (4:96) as eluent to give the titled compound.

Characteristic NMR Resonances; $^1$H NMR 400 MHz (CDCl$_3$); 7.45 (aromatic ABq, 4H, J=8.4 Hz, Δσ=23.6 Hz), 5.24 (s, 1H), 3.78 (s, 3H), 2.75 (m, 2H), 2.56 (m, 2H), 1.5–1.7 (m, 4H), 0.904 (t, 3H, J=7.3 Hz), 0.87 (t, 3H, J=7.2 Hz).

Step 3 Preparation of α-([-[5,7-dipropyl-3-(trifluoromethyl)-1,2-benzisoxazol-6-yl]oxy]-4-chlorobenzeneacetic acid.

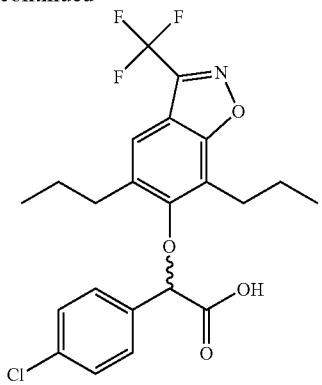

The title acid was prepared as was described for example 1, step 5 from the indicated ester (18.9 gm, 1.0 eq) and NaOH (39.4 ml, 1.02 M, 1.0 eq). The resulting oil was crystallized from hexanes to give the titled compound.

Characteristic NMR Resonances; $^1$H NMR 400 MHz (CDCl$_3$); 7.45 (aromatic ABq, 4H, J=8.3 Hz, Δσ=15.1 Hz), 5.28 (s, 1H), 2.77 (m, 2H), 2.54 (m, 2H), 1.5–1.7 (m, 4H), 0.886 (t, 3H, J=7.3 Hz), 0.875 (t, 3H, J=7.2 Hz).

Example 3

Step 1 Preparation of Methyl 2-Bromo-2-(4-trifluoromethylthiophenyl)acetate

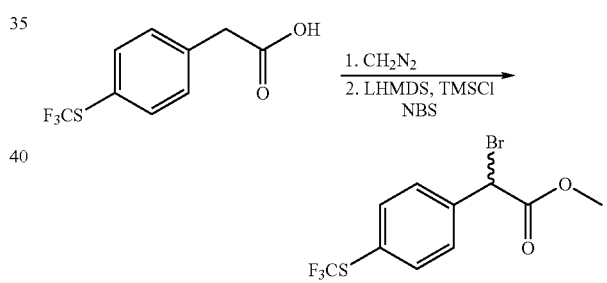

Commercially available 4-(trifluoromethylthio) phenylacetic acid (0.950 g,) was dissolved in ether (20 mL). Diazomethane was added until the reaction mixture remained yellow. Excess diazomethane was destroyed and the solution was reduced i. vac. The crude oil was cooled to −78° C. in THF (100 mL). Lithium bis (trimethylsilyl) amide (5.5 mL, 1.1 eq) was added to the reaction and stirred for 20 minutes. Chlorotrimethylsilane (0.875 mL, 1.875 eq) was added at −78° C. and stirred for 20 minutes. N-bromosuccinimide (0.938 g, 1.05 eq) was added to the reaction mixture. The reaction mixture was allowed to stir and warm to room temperature overnight. The reaction mixture was diluted with H$_2$O. The organic layer was extracted with ethyl acetate. The organic phase was dried over sodium sulfate and the solvent was evaporated to give a yellow oil. The resulting oil was chromatographed on silica gel using hexanes:ethyl acetate (95:5) to give methyl 2-bromo-2-(4-trifluoromethylthiophenyl)acetate.

Characteristic NMR Resonances; $^1$H NMR 500 MHz (CDCl$_3$); 7.64 (d, 2H), 7.70 (d 2H), 5.37 (s, 1H), 3.82 (s, 3H)

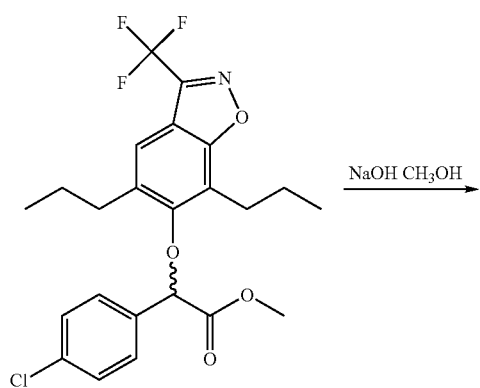

Step 2 Preparation of Methyl α-[[5,7-dipropyl-3-(trifluoromethyl)-1,2-benzisoxazol-6-yl]oxy]-4-[(trifluoromethyl)thio]benzeneacetate.

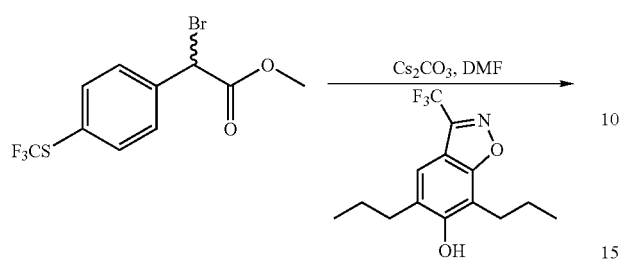

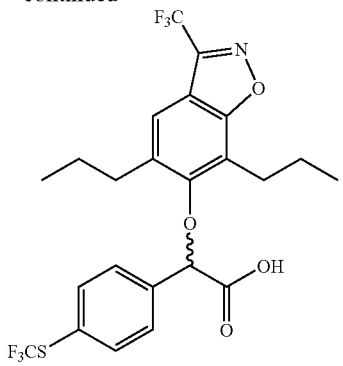

-continued

The title acid was prepared as was described for example 1, step 5 from the indicated ester (105 mg, 1.0 eq) and NaOH (0.49 mL, 2 M, 2.5 eq).

Characteristic NMR Resonances: $^1$H NMR 500 MHz (CDCl$_3$); 7.74 (d, 2H), 7.63 (d, 2H), 5.30 (s, 1H), 2.76 (m, 2H), 2.58 (m, 2H), 1.61 (m, 4H), 0.92 (m, 6H), Example 4

Step 1 Preparation of Methyl α-[[5,7-dipropyl-3-(trifluoromethyl)-1,2-benzisoxazol-6-yl]oxy]-4-(1-methylethyl)benzeneacetate.

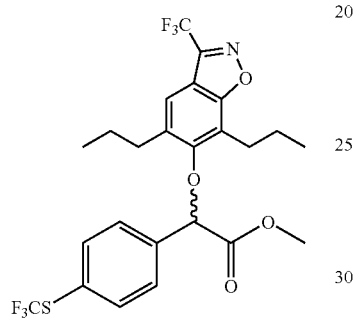

The title ester was prepared as was described for example 1, step 4 from the indicated bromide (85 mg) and the indicated phenol (74 mg). The product was purified by silica gel chromatography (toluene) to yield the desired ester.

Characteristic NMR Resonances; $^1$H NMR 500 MHz (CDCl$_3$); 7.74 (d, 2H), 7.62 (dd, 2H), 7.42 (s, 1H), 5.30 (s 1H), 3.79 (s, 3H), 2.75 (m, 2H), 2.55 (m, 2H), 1.63 (m, 4H), 0.88 (m, 6H).

Step 3 Preparation of α-[[5,7-dipropyl-3-(trifluoromethyl)-1,2-benzisoxazol-6-yl]oxy]-4-[(trifluoromethyl)thio]benzeneacetic acid.

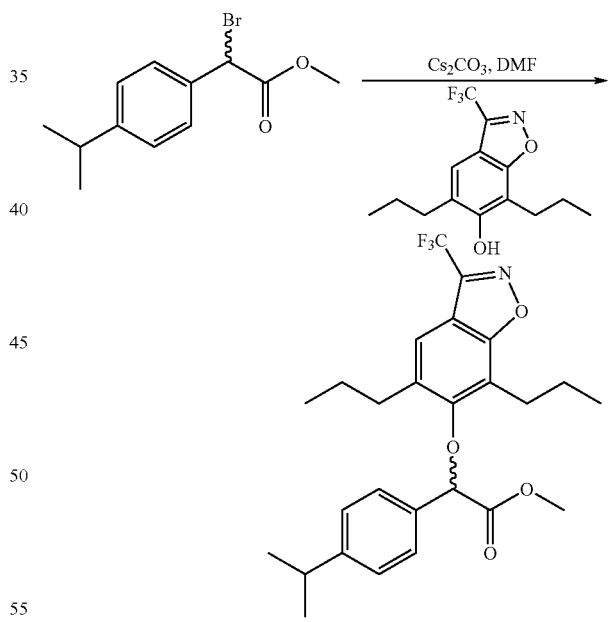

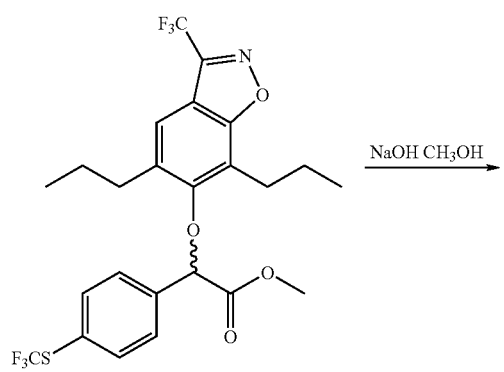

The title ester was prepared as was described for example 1, step 4 from the indicated bromide (54 mg) and the indicated phenol (57 mg). The product was purified by silica gel chromatography (hexanes:ethyl acetate 95:5) to yield the desired ester.

Characteristic NMR Resonances; $^1$H NMR 500 MHz (CDCl$_3$); 7.42 (d, 2H), 7.39 (s, 1H), 7.28 (d, 2H), 5.42 (s, 1H), 3.56 (s, 3H), 2.95 (m, 1H), 2.63 (m, 4H), 1.61 (m, 4H), 1.38 (d, 6H), 0.89 (m, 6H)

Step 2 Preparation of α-[[5,7-dipropyl-3-(trifluoromethyl)-1,2-benzisoxazol-6-yl]oxy]-4-(1-methylethyl)benzeneacetic acid.

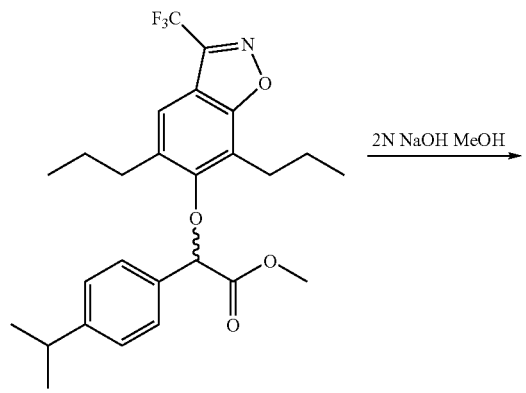

The title acid was prepared as was described for example 1, step 5 from the indicated ester (85 mg, 1.0 eq) and NaOH (0.356 mL, 5 M, 2.5 eq).

Characteristic NMR Resonances; $^1$H NMR 400 MHz (CDCl$_3$); 7.42 (m, 3H), 7.28 (d, 2H), 5.25 (s, 1H). 2.95 (m, 1H), 2.61 (m, 4H), 1.60 (m, 4H), 1.38 (d, 6H), 0.85 (m, 6H), Example 5

Step 1 Preparation of Methyl 4-(2-methylpropyl)phenylacetate.

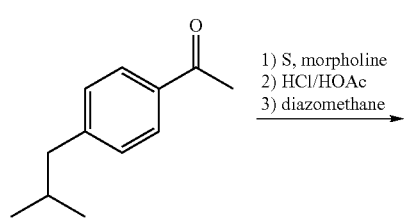

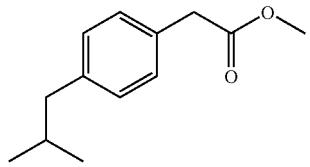

Sulfur (5.0 g, 156 mmol), 4-isobutyl acetophenone (14.4 g, 82 mmol) and morpholine (20 mL) were combined and heated under reflux for 18 hrs. The morpholine was distilled from the reaction leaving a dark residue. The residue was cooled to ambient temperature then treated with Conc. HCl/HOAc 1/1 (50 mL) and heated under reflux for 24 hrs. The volatiles were then distilled from the dark reaction mixture. The residue was suspended in acetone then filtered to remove a colorless solid. The filtrate was treated with decolorizing charcoal, filtered through Celite and concentrated to give an orange solid. The crude solid was suspended in ether and treated with excess diazomethane, let stand for 1 hour. Excess diazomethane was destroyed and the solution concentrated. The residue was purified by silica gel chromatography to yield the desired product.

Characteristic NMR Resonances; $^1$H NMR 400 MHz (CDCl$_3$); 7.12 (ABq, 4H), 3.72 (s, 3H), 3.61 (s, 2H), 2.45 (d, 2H), 1.90 (m, 1H), 0.96 (d, 6H).

Step 2 Preparation of Methyl 2-Bromo-2-(4-(2-methylpropyl)phenyl)acetate

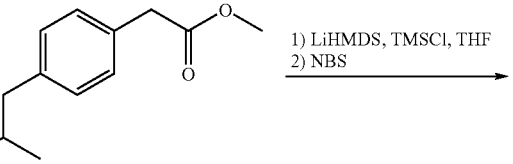

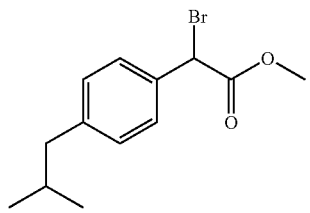

The bromide was prepared following the procedure of Example 3, Step 1 to give the desired compound as an oil.

Characteristic NMR Resonances; $^1$H NMR 400 MHz (CDCl$_3$); 7.10 (ABq, 4H), 5.15 (s, 1H), 3.72 (s, 3H), 2.45 (d, 2H), 1.90 (m, 1H), 0.96 (d, 6H).

Step 3 Preparation of Methyl α-[[5,7-dipropyl-3-(trifluoromethyl)-1,2-benzisoxazol-6-yl]oxy]-4-(2-methylpropyl) benzeneacetate.

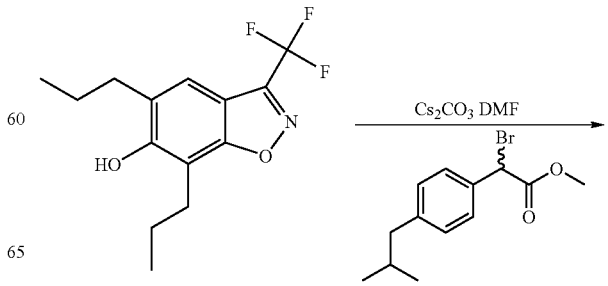

-continued

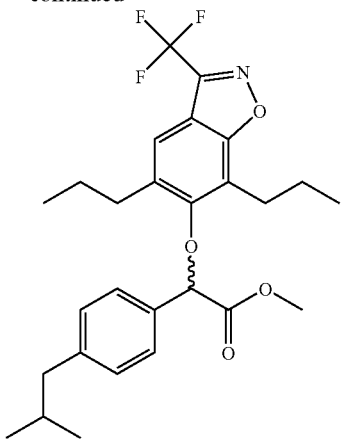

The title ester was prepared as for example 1, step 4 from the indicated bromide (82.3 mg, 0.2 mmol) and the indicated phenol (82.8 g, 0.29 mmol). The product was purified by silica gel chromatography (toluene) to yield the desired ester.

Characteristic NMR Resonances; $^1$H NMR 400 MHz (CDCl$_3$); 7.45 (aromatic ABq, 4H), 5.28 (s, 1H), 3.70 (s, 3H), 2.77 (m, 2H), 2.54 (m, 2H), 2.45 (d, 2H), 1.90 (m, 1H), 1.5–1.7 (m, 4H), 0.95 (d, 6H), 0.88 (t, 3H, J=7.3 Hz), 0.87 (t, 3H).

4 Preparation of α-[[5,7-dipropyl-3-(trifluoromethyl)-1,2-benzisoxazol-6-yl]oxy]-4-(2-methylpropyl)benzeneacetic acid.

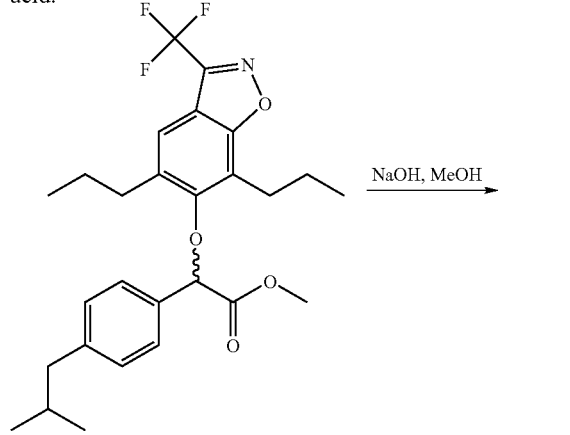

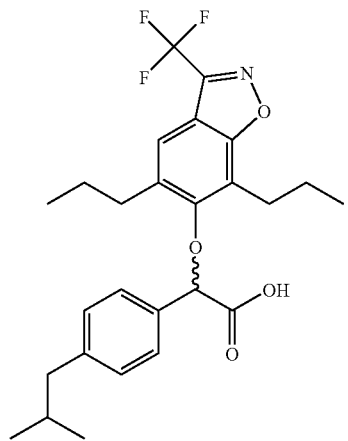

The title acid was prepared as for example 1, step 5 from the indicated ester (100 mg, 1.0 eq) and NaOH (0.08 mL, 5 M, 2.0 eq).

Characteristic NMR Resonances; $^1$H NMR 400 MHz (CDCl$_3$); 7.45 (aromatic ABq, 4H), 5.28 (s, 1H), 2.77 (m, 2H), 2.54 (m, 2H), 2.45 (d, 2H), 1.90 (m, 1H), 1.5–1.7 (m, 4H), 0.95 (d, 6H), 0.88 (t, 3H), 0.87 (t, 3H).

Example 6

Step 1

The alpha-bromoester of the following step which is derived from the (S) enantiomer of pyrrolidine lactamide is known. See *Tet Let*, 37, 2683–2686, 1996. Synthesis is identical to the reported route, starting in this case from (R) isobutyl lactate. NMR (CDCl$_3$) σ7.57 (m, 2H), 7.37 (m, 3H), 5.47 (s, 1H), 4.13 (q, 1H, J=7.1 Hz) 3.3–3.62 (m, 4H), 1.8–2.0 (m, 4H), 1.50 (d, 3H, J=6.7 Hz), 1.43 (d, 3H, J=6.8 Hz).

Step 2 Preparation of α-[[5,7-dipropyl-3-(trifluoromethyl)-1,2-benzisoxazol-6-yl]oxy]benzeneacetic acid (R)Pyrrolidinelactamide ester.

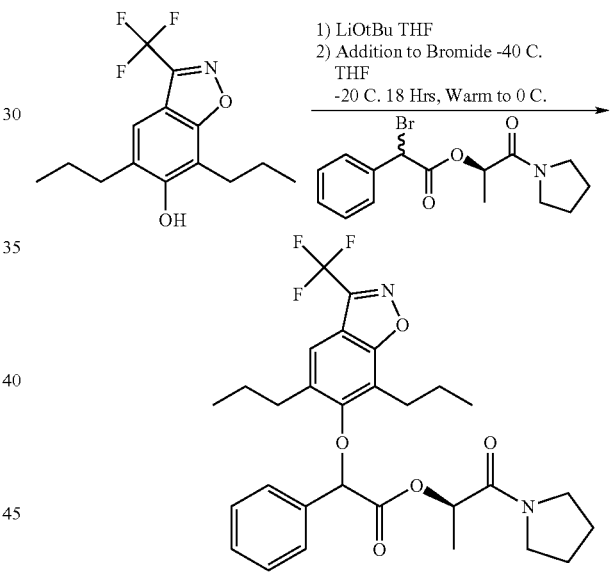

The phenol (377 mg, 1.2 eq) was dissolved in THF (1.5 ml). Lithium tert-butoxide in THF (1 M solution, 1.2 ml, 1.0 eq) was added. The bromide (372 mg, 1.0 eq) was dissolved in THF (6 ml) and cooled to −30 C. The solution of the lithium phenoxide was added dropwise to the solution of the bromide. The mixture was left at −20 C. 19 Hrs followed by slow warming to 0 C. over 3 Hrs. The mixture was quenched with 1 N HCl and extracted with ethyl acetate. The organic phase was separated and washed with water followed by brine. The organic phase was dried over sodium sulfate and the solvent was evaporated to give a oil. The resulting oil was chromatographed on silica gel with toluene:hexanes: tert-butanol as eluent (48:48:4) to give the titled compound.

NMR (CDCl$_3$) σ7.52 (brd m, 2H), 7.42 (m, 4H), 5.34 (s, 1H), 5.26 (q, 1H, J=6.8 Hz), 3.56 (m, 2H), 3.45 (m, 2H), 2.69 (m, 2H), 2.54 (m, 2H), 1.94 (p, 2H, J=6.6 Hz), 1.87 (p, 2H, J=6.6 Hz), 1.45–1.75 (m, H), 1.36 (d, 3H, J=6.6 Hz), 0.866 (t, 3H, J=7.2 Hz), 0.847 (t, 3H, J=7.2 Hz).

Step 2 Preparation of α-[[5,7-dipropyl-3-(trifluoromethyl)-1,2-benzisoxazol-6-yl]oxy]benzeneacetic acid.

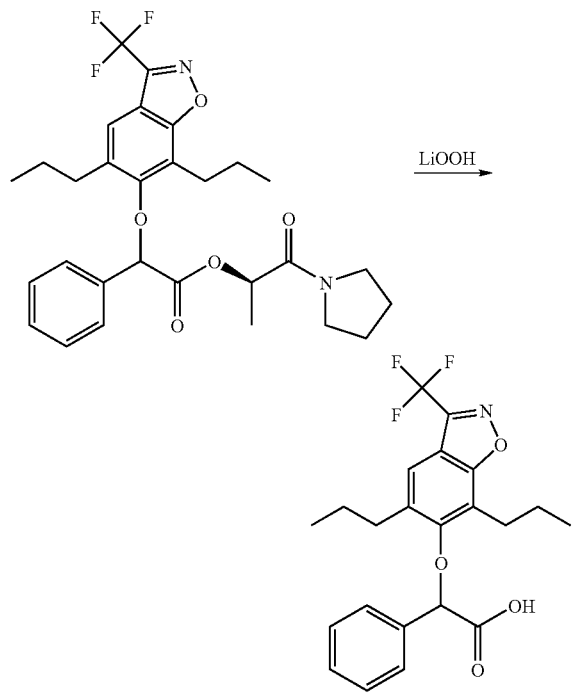

The ester (466 mg, 1.0 eq) was dissolved in methanol (15 ml). Aqueous lithium hydroxide (1.0 M, 1.71 ml, 2.0 eq) was diluted into aqueous hydrogen peroxide (30% nominal, 5 ml). The solution of LiOOH was added to the methanol solution of the ester at RT. After 1 Hr the mixture was quenched with 2 N HCl and extracted with ethyl acetate. The organic phase was separated and washed with water followed dilute aqueous sodium bisulfite and brine. The organic phase was dried over sodium sulfate and the solvent was evaporated to give a oil. The resulting oil was chromatographed on silica gel with hexanes:ethyl acetate plus 2% acetic acid as eluent (95:5) to give the titled compound.

The enantiomeric excess of the final product was determined by HPLC using a ChiralCel OD-R analytical column with acetonitrile water 0.1% TFA as eluent.

Spectra are as were described for the racemic material of Example 1

Example 7

Step 1 Preparation of 2,4-dihydroxy-3-propyl-1',1',1'-trifluoroacetophenone

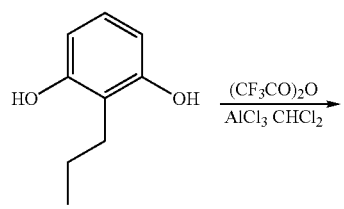

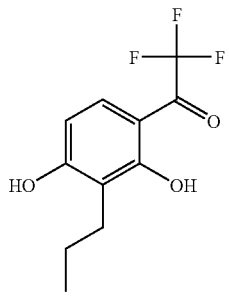

A solution of 2-propylresorcinol (5.0 grams) and trifluoroacetic anhydride (9.6 mL) in 1,2-dichloroethane (30.0 mL) was treated with aluminum chloride(4.38 grams). This mixture was stirred overnight. The reaction mixture was partitioned between methylene choride and water. The organic phase was dried over sodium sulfate and filtered. The solvent was evaporated and the resulting solid was recrystalized using methylene chloride and cyclohexane (1:1) to give the titled compound.

NMR (CDCl$_3$) δ7.59 (d, 1H), 6.24 (d, 1H), 5.92 (s, 1H), 2.63 (t, 2H), 1.74 (s, 1H), 1.58 (m, 2H), 0.98 (t, 3H).

Step 2 Preparation of 3-trifluoromethyl-7-propyl-6-hydroxy-1,2-benzisoxazole.

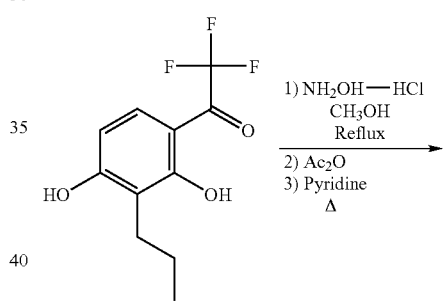

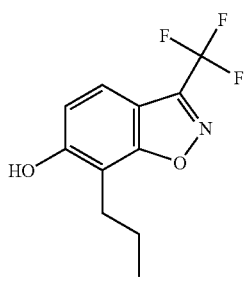

A mixture of 2,4-dihydroxy-3-propyl-1',1',1'-trifluoroacetophenone(2.5 grams), sodium acetate (4.18 grams), hydroxylamine hydrochloride (3.59 grams) and methanol (80 mL) was refluxed overnight. The solvent was then evaporated and the resulting solid was partitioned between ethyl acetate and pH 7 buffer. The organic phase was separated and washed with brine. The organic phase was dried over sodium sulfate and the solvent was evaporated to give a oil. The oil was then dissolved in acetic anhydride. The solution was stirred for two hours, then the acetic anhydride was evaporated in vac. The residue was partitioned between ethyl acetate and pH 7 buffer and the organic phase was dried over sodium sulfate. The organic phase was evaporated to give an oil. This was dissolved in pyridine and refluxed overnight. The solvent was evaporated in vac to give an oil which was chromatographed on silica gel using ethyl acetate and hexane (1:4) to give the titled compound.

NMR (CDCl$_3$) δ7.46 (d, 1H), 6.92 (d, 1H), 5.42 (bs, 1H), 2.89 (t, 2H), 1.74 (m, 2H), 0.98 (t, 3H).

Step 3 Preparation of 5-Chloro-6-hydroxy-7-propyl-3-trifluoromethyl-1,2-benzisoxazole.

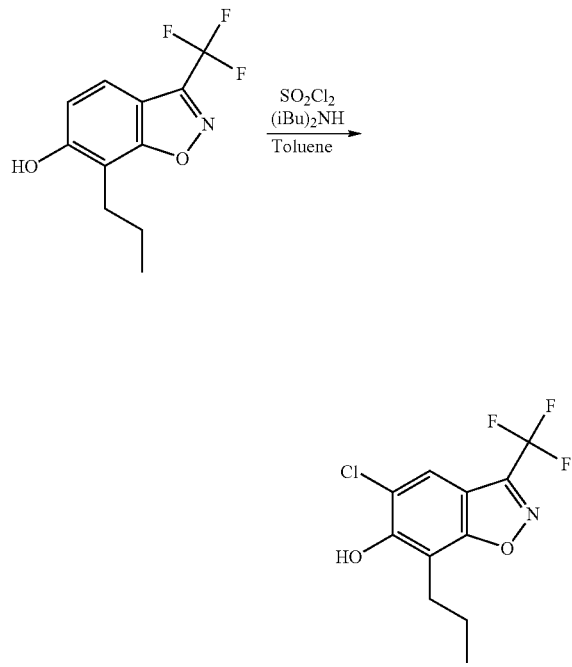

Diisobutylamine (0.8 ml, 0.10 eq) and 6-hydroxy-7-propyl-3-trifluoromethylbenzisoxazole (11 gm, 1.0 eq) were dissolved in toluene (275 ml) at room temperature. Slow addition of sulfuryl chloride (4.20 ml, 1.15 eq) results in a suspension which was stirred overnight. Additional diisobutylamine (total 1.6 ml, 0.4 eq) was added in four equal portions over 24 hr until no further starting benzisoxazole was detected by analytical TLC. The reaction mixture was poured into saturated sodium bisulfite (500 ml) and ethyl ether (700 ml). The phases were separated. The ether phase was washed with brine and dried over Na$_2$SO$_4$. The solvent was evaporated in vac to give an orange solid which was purified by chromatography on silica gel eluting with acetone:hexane (2:98) to give the title compound.

Step 4 Preparation of α-[[5-chloro-7-propyl-3-(trifluoromethyl)-1,2-benzisoxazol-6-yl]oxy]-4-chlorobenzeneacetic acid (R)Pyrrolidinelactamide ester.

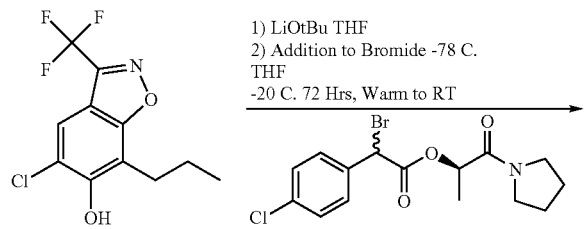

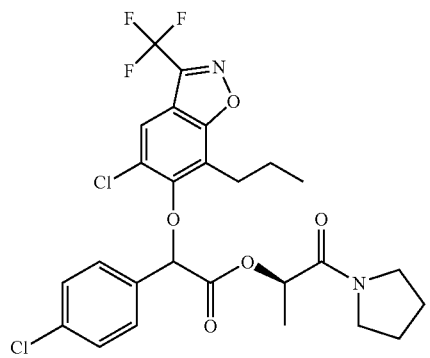

To a solution of the phenol (1.0 eq) in THF (5 ml) was added a solution of lithium tert-butoxide in THF (1M, 3.74 ml, 0.95 eq). The phenoxide solution was added dropwise to a solution of the bromide (1.478 g, 1 eq) in THF (1 ml) at −78° C. The resulting solution was allowed to stand at approx. −20° C. for 72 Hrs. The reaction mixture was allowed to warm to room temperature and quench with 1N HCl. The mixture was extracted with ethyl acetate. The organic phase was separated and washed with brine. The organic phase was dried over sodium sulfate. The solvent was evaporated to give an oil. The crude oil was chromatographed on a silica gel column, eluting with toluene:hexane:tert-butanol (20:77:3) to give the title compound.

$^1$H NMR (400 MHz, CDCl$_3$); δ7.68 (s, 1H), 7.45 (aromatic ABq, 4H, J=8.5 Hz, Δδ=44.0), 5.72 (s, 1H), 5.28 (q, 1H, J=6.8 Hz), 3.58 (m, 2H), 3.40 (m, 2H), 2.83 (m, 2H), 2.68 (m, 2H), 1.97 (m, 2H), 1.88 (m, 2H), 1.61–1.68 (m, 1H), 1.37–1.43 (m, 1H), 1.39 (d, 3H, J=6.6 Hz), 0.87 (t, 3H, J=7.3 Hz).

MS ESI 596.1 M+Na

Step 5 Preparation of α-[[5-chloro-7-propyl-3-(trifluoromethyl)-1,2-benzisoxazol-6-yl]oxy]chlorobenzeneacetic acid.

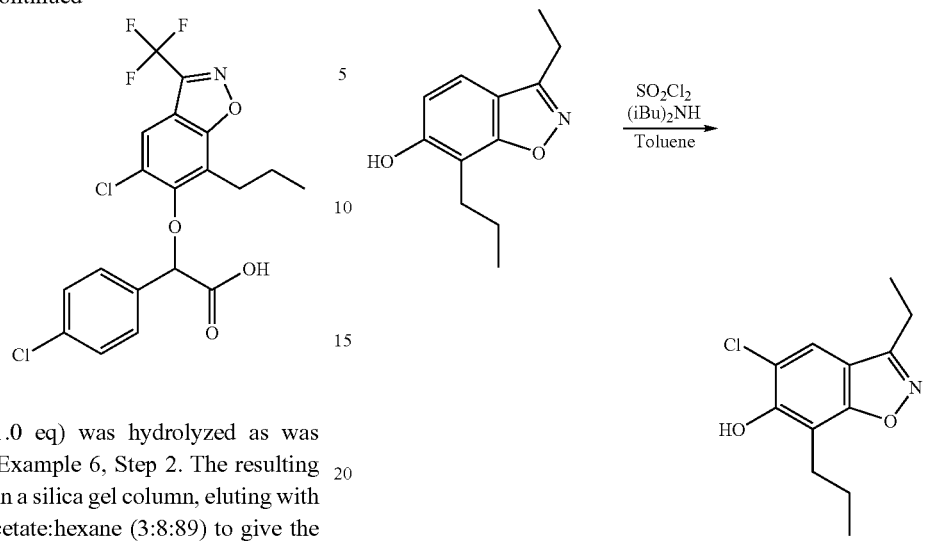

The ester (1.1142 g, 1.0 eq) was hydrolyzed as was described for the ester of Example 6, Step 2. The resulting oil was chromatographed on a silica gel column, eluting with glacial acetic acid:ethyl acetate:hexane (3:8:89) to give the title compound as a white solid. The enantiomeric excess of this product was determined by HPLC using a ChiralCel OD-R analytical column with acetonitrile:water (55:45) containing 0.1% TFA as eluent.

$^1$H NMR (400 MHz, CDCl$_3$); δ7.45 (aromatic ABq, 4H, J=8.5 Hz, Δδ=22.9), 5.66 (s, 1H), 2.81 (m, 1H), 2.63 (m, 1H), 1.61–1.66 (m, 1H), 1.34–1.37 (m, 1H), 0.86 (t, 3H, J=7.3 Hz).

MS ESI 449.0 M+1

Example 8

Step 1 Preparation of 5-Chloro-3-ethyl-6-hydroxy-7-propyl-1,2-benzisoxazole

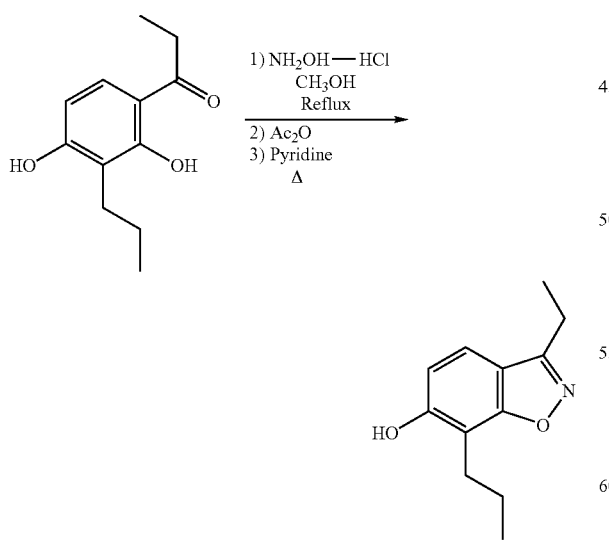

Commercially available 2,4-dihydroxy-3-propylpropiophenone was converted to the benzisoxazole as was described for example 1, step 3.

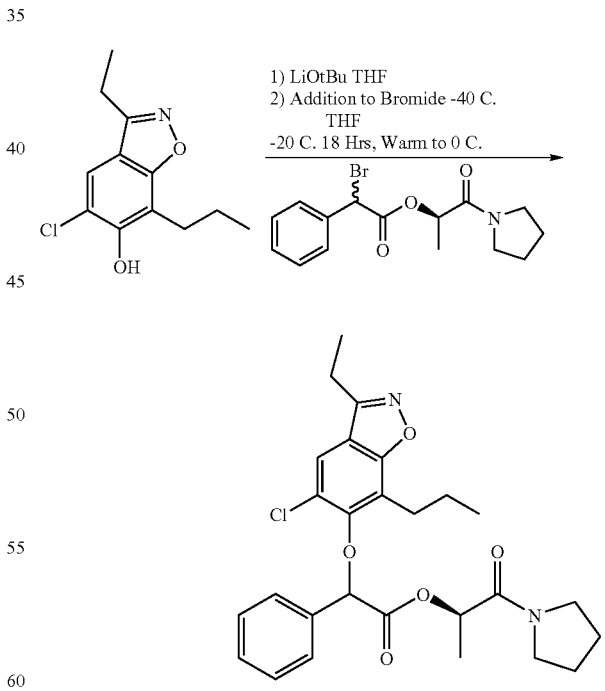

Chlorination of the 3-ethyl-6-hydroxy-7-propyl-1,2-benzisoxazole was carried out as for Example 7, Step 3. The product was purified by recrystallization from hexanes.

Characteristic NMR Resonances; $^1$H NMR 400 MHz (CDCl$_3$) d 7.49 (s, 1H), 5.97 (s, 1H), 2.94 (m, 4H), 1.75 (sex, 2H, J=7.6 Hz), 1.43 (t, 3H, J=7.5 Hz), 0.994 (t, 3H, J=7.3 Hz).

Step, 4 Preparation of α-[[5-chloro-3-ethyl-7-propyl-1,2-benzisoxazol-6-yl]oxy]benzeneacetic acid (R)Pyrrolidinelactamide ester.

The title compound was prepared as was described for example 6, step 2. The phenol (1.46 g mg, 1.2 eq) was dissolved in THF (5.0 ml). Lithium tert-butoxide in THF (1 M solution, 5.57 ml, 1.0 eq) was added. The bromide (1.72 mg, 1.0 eq) was dissolved in THF (10 ml) and cooled to −30° C. The solution of the lithium phenoxide was added dropwise to the solution of the bromide. The mixture was left at −20° C. for 19 Hrs followed by slow warming to 0° C. over 3 Hrs. The mixture was quenched with 1 N HCl and extracted with ethyl acetate. The organic phase was separated and washed with water followed by brine. The organic phase was dried over sodium sulfate and the solvent was evaporated to give a oil. The resulting oil was chromatographed on silica gel with toluene:hexanes:tert-butanol as eluent (48:48:4) to give the titled compound.

NMR (CDCl$_3$) σ7.52 (m, 3H), 7.41 (m, 2H), 5.66 (s, 1H), 5.33 (q, 1H, J=6.8), 3.33 to 3.65 (4 highly symmetric multiplets, 4H), 2.94 (q, 2H, J=7.6 Hz), 2.59 (ABX$_2$ pattern, 2H), 1.94 (m, 2H), 1.87 (m, 2H), 1.61 (m, 1H), 1.43 (t, 3H, J=7.6 Hz 1.31 (d, 3H, J=6.9 Hz), 1.28 (m, 1H), 0.795 (t, 3H, J=7.3 Hz).

Step 5 Preparation of α-[[5-chloro-3-ethyl-7-propyl-1,2-benzisoxazol-6-yl]oxy]benzeneacetic acid.

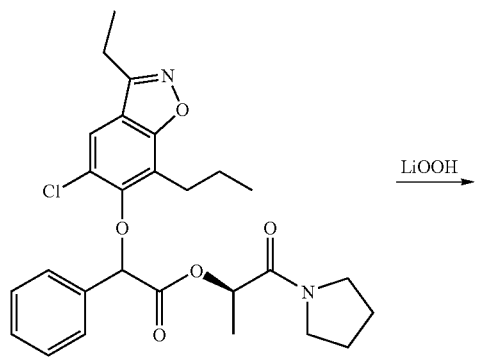

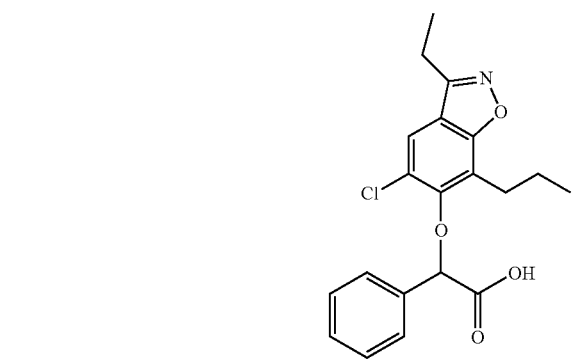

The ester (452 mg, 1.0 eq) was hydrolyzed as was described for the ester of Example 6, Step 2. The resulting oil was chromatographed on a YMC RP8 HPLC column eluting with a linear water:acetonitrile (0.1% TFA) gradient, 90:10 to 0:100 to give the titled compound as an oil.

The enantiomeric excess of the final product was determined by HPLC using a ChiralCel OD-R analytical column with 60:40 acetonitrile:water 0.1% TFA as eluent.

NMR (CDCl$_3$) δ7.56 (s, 1H), 7.41–7.51 (m, 5H), 5.59 (s, 1H), 2.96 (q, 2H, J=7.6 Hz), 2.53 (ABX$_2$ pattern, 2H), 1.58 (m, 1H), 1.44 (t, 3H, J=7.6 Hz), 1.22 (m, 1H), 0.779 (t, 3H, J=7.4 Hz).

Example 9

Step, 1 Preparation of 2,4-Dihydroxy-3-allylbenzophenone

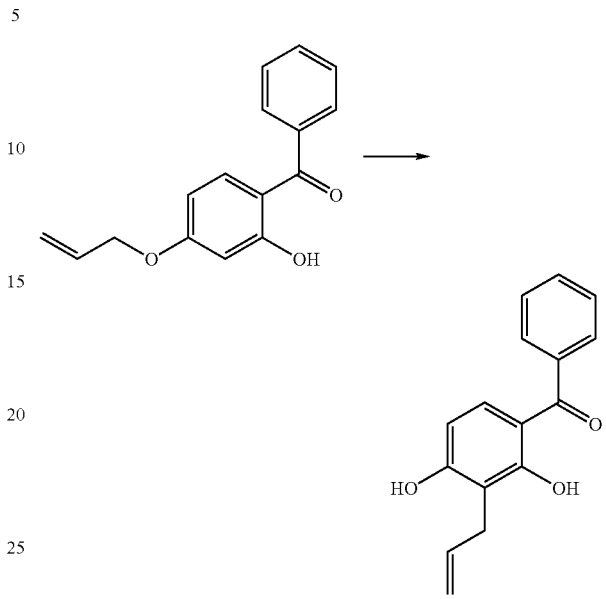

Commercially available 4-allyloxy-2-hydroxybenzophenone (15 g) was rearranged by heating under reflux in ortho-dichlorobenzene (60 mL) for 26 hours. The product was isolated by dilution of the reaction mixture with 5 volumes hexanes to give a crystalline product as fine needles.

Characteristic NMR Resonances; $^1$H NMR 400 MHz (CDCl$_3$); 7.62–7.59 (m, 2H), 7.56–7.52 (m, 2H), 7.49–7.44 (m, 2H), 7.40 (d, 1H, J=8.9 Hz), 6.34 (d, 1H, J=8.8 Hz), 6.02 (ddt, 1H, J=17.21, 10.1, 6.2 Hz), 5.72 (s, 1H, phenol OH), 5.14–5.24 (m, 2H), 3.53 (d with fine splitting, 2H, J=6.2 Hz).

Step 2 Preparation of 2,4-Dihydroxy-3-propylbenzophenone

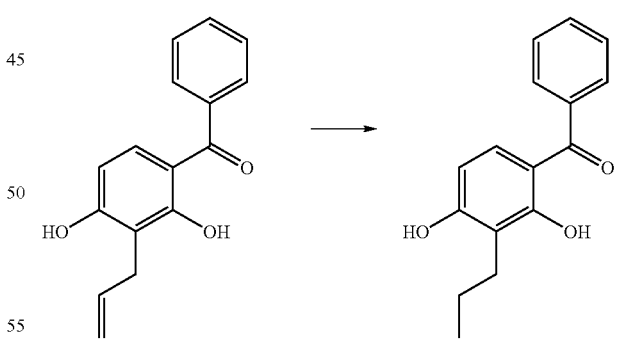

A solution of 2,4-dihydroxy-3-(2-propenyl)benzophenone (3 g) was reduced under ~1 atm H$_2$ in ethyl acetate (100 mL) over 10% Pd/C catalyst (0.3 grams) for 3 hours. The product was purified by crystallization from methanol/water. The product is obtained as small yellow plates.

Characteristic NMR Resonances; $^1$H NMR 400 MHz (CDCl$_3$); 7.61–7.59 (m, 2H), 7.55–7.51 (m, 1H), 7.48–7.44 (m, 2H), 7.33 (d, 1H, J=8.8 Hz), 6.29 (d, 1H, J=8.8 Hz), 5.51 (s, 1H, phenol OH), 2.66 (dd, 2H, J=7.6, 9.3 Hz), 1.61 (sext, 2H, J=7.7 Hz), 0.99 (t, 3H, J=7.3 Hz).

Step 3 Preparation of 6-hydroxy-7-propyl-3-phenyl-1,2-benzisoxazole

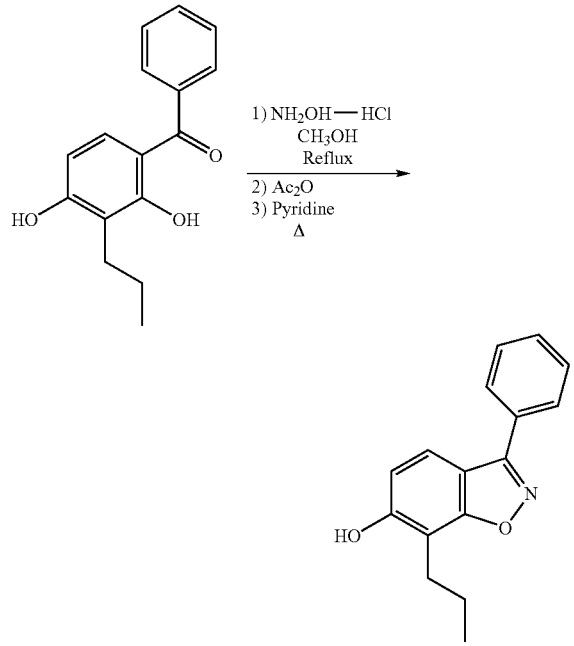

The 2,4-dihydroxy-3-propylbenzophenone (2.5 g, 1.0 Eq, 9.8 mmol) was converted to the oxime with NH$_2$OH—HCl (2.7 g, 4.0 Eq, 39 mmol) and NaOAc (3.21 g, 4.0 Eq, 39 mmol) as in Example 1 Step 3. The oxime was purified by elution from a silica gel column (180 g E. Merck 40–63μ) with 97:3 Toluene:EtOAc. The product oxime (1.82 g) was further treated as in Example 1 Step 3 with acetic anhydride (15 ml) and subsequent reflux in pyridine (15 ml).

The cooled reaction mixture was poured into 2 N HCl and EtOAc. The aqueous phase was extracted with EtOAc and washed with sat'd aq NaHCO$_3$, followed by sat'd aq NaCl. The EtOAc extracts were dried over Na$_2$SO$_4$ and reduced i. vac. The residue was taken up in refluxing toluene (50 ml). The product benzisoxazole is obtained as colorless crystals upon cooling to RT.

Characteristic NMR Resonances; $^1$H NMR 400 MHz (CDCl$_3$); 7.92–7.89 (m, 2H), 7.57 (d, 1H, J=8.5 Hz), 7.55–7.49 (m, 3H), 6.86 (d, 1H, J=8.6 Hz), 5.14 (s, 1H, phenol OH), 2.90 (dd, 2H, J=8.9, 7.6 Hz), 1.76 (sext, 2H, J=7.5 Hz), 1.01 (t, 3H, J=7.3 Hz).

MS CI NH$_3$ M+1 254.1

Step 4 Preparation of 5,7-dipropyl-6-hydroxy-3-phenyl-1,2-benzisoxazole.

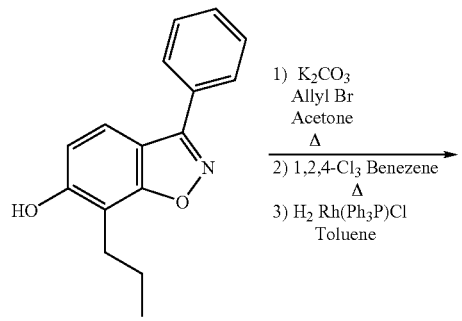

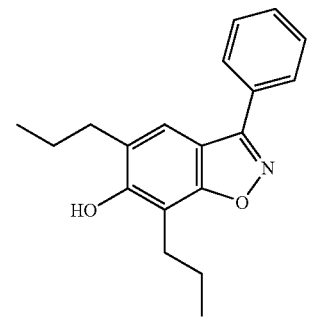

A heterogeneous mixture of 6-hydroxy-3-phenyl-7-propyl-1,2-benzisoxazole (12.6 g, 50 mmol), allyl bromide (12.1 g, 8.6 mL, 100 mmol) and K$_2$CO$_3$ (20.7 g, 150 mmol) in acetone (0.50 L) was vigorously stirred at 50° C. for 5 h. The reaction mixture was then filtered through a pad of silica gel and the filtrate was concentrated. The residue was azeotroped with toluene in vac. to give the allyl ether which was used without purification.

The allyl ether (14.7 g, 50 mmol) was dissolved in 1,2,4-trichlorobenzene (50 mL). The solution was heated under reflux for 6 h. After being cooled to room temperature, the reaction mixture was loaded onto a silica gel column and eluted first with hexane and then with ethyl acetate:hexane (1:9) to give the ortho allyl rearrangement product. The ortho allyl product (8.8 g, 30 mmol) was dissolved in toluene (250 mL). After addition of the catalyst Rh(PPh$_3$)$_3$Cl (1.38 g, 1.5 mmol), the homogeneous solution was stirred under H$_2$ (1 atm) for 5 h. The solvent was evaporated and the residue was chromatographed on silica gel eluting with ethyl acetate:hexane (1:9) to give the title compound.

Characteristic $^1$H NMR (CDCl$_3$, 400 MHz): δ7.50–7.26 (m, 5H), 7.48(s, 1H), 5.20(s, 1H), 2.95(symm.m, 2H), 2.73(symm.m., 2H), 1.68–1.83(m, 4H), 1.03(t, J=7.0 Hz, 3H), 1.01(t, J=7.0 Hz, 3H).

MS(ESI): 294.1(M$^+$+1)

Step 5 Preparation of Methyl α-[[5,7-dipropyl-3-phenyl-1,2-benzisoxazol-6-yl]oxy]benzeneacetate.

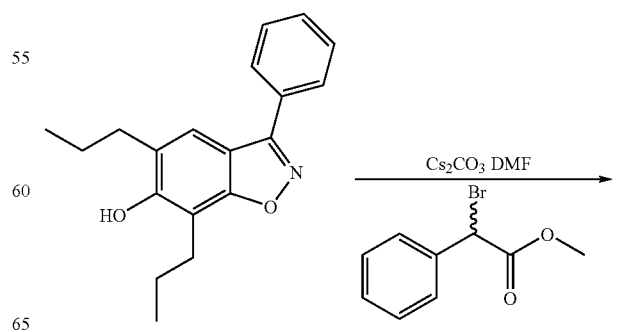

-continued

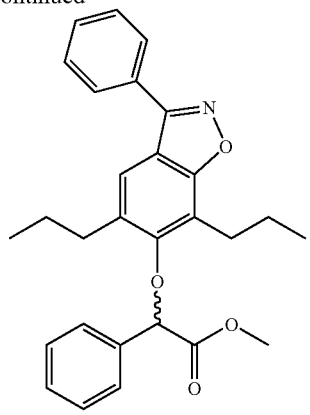

Methyl 2-bromo-2-phenylacetate (2.29 g 10.0 mmol), Cs$_2$CO$_3$ (3.25 g, 10.0 mmol) and the indicated benzisoxazole (3.09 g, 10.5 mmol) were combined in 50 ml DMF at room temperature. The mixture was stirred 19 h. The suspension was poured into water (250 mL) and extracted with ethyl acetate. The organic phase was separated and washed with water followed by brine. The organic phase was dried over sodium sulfate and the solvent was evaporated to give an oil. The resulting oil was chromatographed on silica gel using ethyl acetate:hexanes (15:85) to give the desired compound.

Characteristic $^1$H NMR (CDCl$_3$, 400 MHz): δ7.30–7.95 (m, 10H), 7.58(s, 1H), 5.41(s, 1H), 3.97(s, 3H), 2.62–2.80 (m, 2H), 2.50–2.61(m., 2H), 1.50–1.71(m, 4H), 0.88(t, 7.1 Hz, 3H), 0.86(t, J=7.1 Hz, 3H).

Step 6 Preparation of α-[[5,7-dipropyl-3-phenyl-1,2-benzisoxazol-6-yl]oxy]benzeneacetic acid.

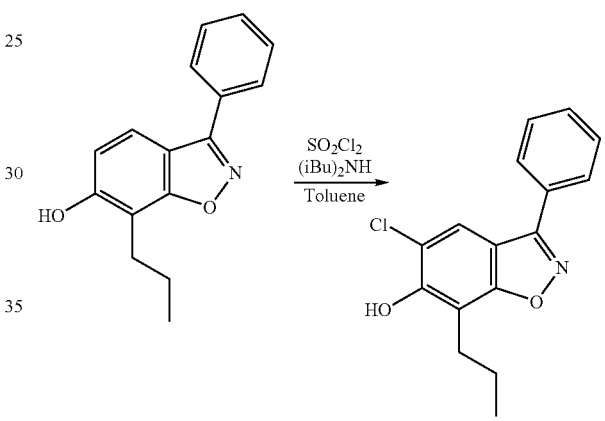

The ester (4.00 g, 9.0 mmol) was dissolved in THF (200 ml). An aqueous solution of lithium hydroxide (2 N, 25 ml) was added. The mixture was stirred at room temperature for 4 h and then acidified with 2 N hydrochloric acid to pH 2. The mixture was extracted with ethyl acetate. The organic phase was washed with brine, dried and concentrated. The residue was chromatographed on silica gel eluting with ethyl acetate:hexane:acetic acid (1:1:0.01) to give the title compound as a white solid.

Characteristic $^1$H NMR (CDCl$_3$, 400 MHz): δ7.29–7.95 (m, 10H), 7.59(s, 1H), 5.29(s, 1H), 2.64–2.84(m, 2H), 2.52–2.63(m., 2H), 1.52–1.73(m, 4H), 0.89(t, 7.1Hz, 3H), 0.88(t, J=7.1 Hz, 3H).

MS(ESI): 430.2(M$^+$+1).

Example 10

Step, 1 Preparation of 5-Chloro-6-hydroxy-3-phenyl-7-propyl-1,2-benzisoxazole

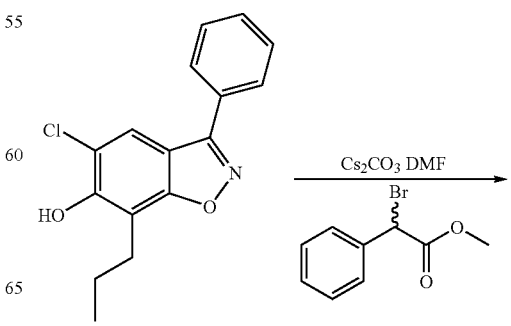

The phenol of example 9 step 3 (0.25 g, 0.86 mmol) was chlorinated as for example 7, step 3. The product was purified by chromatography on silica gel eluting with ethyl acetate:hexane (10:90).

Characteristic $^1$H NMR (CDCl$_3$, 400 MHz): δ7.94(s, 1H), 7.90–7.93(m, 2H), 7.48–7.55(m, 3H), 5.99(s, 1H), 2.79(t, J=7.2 Hz, 2H), 1.70–1.79(m., 2H), 1.02 (t, J=7.0 Hz, 3H)

MS(ESI): 288.1(M$^+$+1).

Step 2 Preparation of Methyl α-[[5-chloro-3-phenyl-7-propyl-1,2-benzisoxazol-6-yl]oxy]benzeneacetate.

-continued

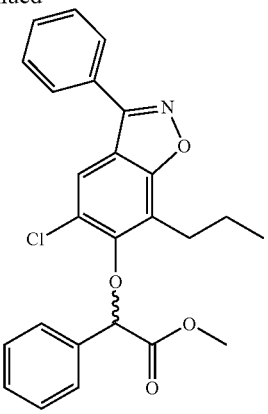

The phenol of step 1(0.25 g, 0.86 mmol) was coupled with commercially available methyl 2-bromo-2-phenylacetate (0.20 g, 0.86 mmol) as was described for example 9, step 5. The product was purified by chromatography on silica gel eluting with ethyl acetate:hexane (10:90).

Characteristic $^1$H NMR (CDCl$_3$, 400 MHz): δ7.92(s, 1H), 7.40–7.95(m, 10H), 1H), 5.77(s, 1H), 3.97(s, 3H), 2.65–2.77 (m, 1H), 2.48–2.57(m, 1H), 1.50–2.65(m, 1H),1.21–1.32(m, 1H), 0.81(t, J=7.1 Hz, 3H).

Step 3 Preparation of α-[[5-chloro-3-phenyl-7-propyl-1,2-benzisoxazol-6-yl]oxy]benzeneacetic acid

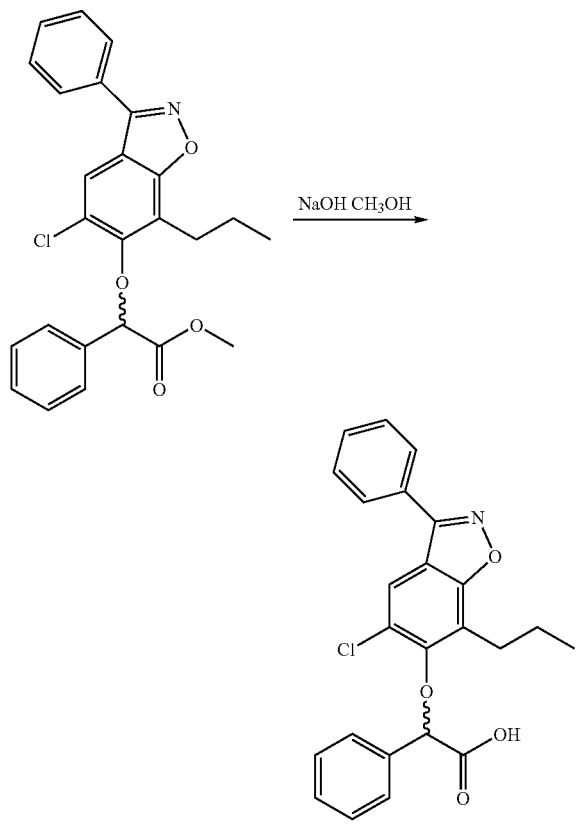

The ester of example 10, step 2 (0.34 g, 0.77 mmol) was hydrolyzed under conditions similar to those described for example 1, step 5. The product was purified by preparative HPLC on a YMC-pack C8 column. CH$_3$CN:H$_2$O (10:90 to 100:0, 15 min gradient) containing 0.1% TFA as eluent.

Characteristic $^1$H NMR (CD$_3$OD, 400 MHz): δ7.91(s, 1H), 7.41–7.95(m, 10H), 5.66(s, 1H), 2.65–2.77(m, 1H), 2.49–2.59(m., 1H), 1.57–1.64(m, 1H), 1.24–1.35(m, 1H), 0.83(t, 7.1 Hz, 3H).

MS(ESI): 422.1(M$^+$+1).

Example 11

Step 1. Preparation of methyl 2,4-dihydroxy-3,5-dipropylbenzoate

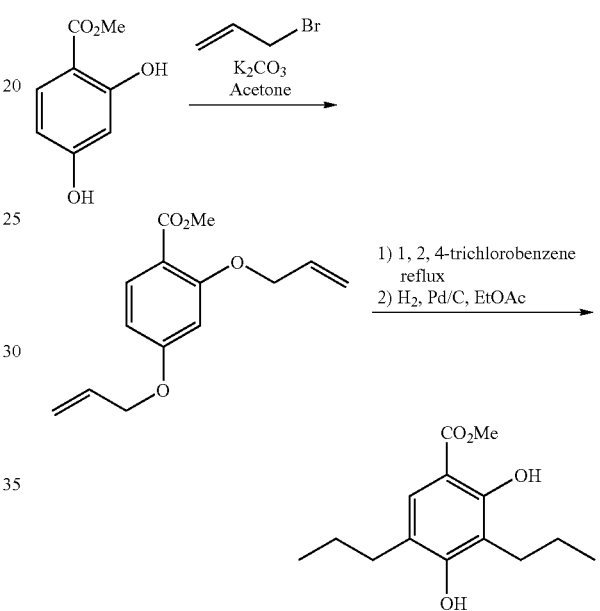

Commercially available 2,4-dihydroxybenzoic acid (25.2 g, 150 mmol) was allylated as was described for example 9, step 4, except that the molar equivalents of the allyl bromide and K$_2$CO$_3$ were doubled. The crude product obtained was used without purification.

The crude allylation product (37.2 g, 150 mmol) was dissolved in 1,2,4-trichlorobenzene (150 mL). The solution was heated under reflux for 7 h and then cooled to 25° C. The reaction mixture was loaded directly onto a silica gel column eluting first with hexane and then with hexane:ethyl acetate (1:9) to give the rearrangment product.

Characteristic $^1$H NMR (CDCl$_3$, 400 MHz) δ11.2(s, 1H), 7.59 (s, 1H), 6.0(m, 2H), 5.95–6.05(m, 2H), 5.16–5.21(m, 4H), 3.95 (s, 3H), 3.52(br. d, J=7.6 Hz, 2d, J=7.7 Hz, 2H).

The bis-allyl product (31.5 g, 127 mmol) was dissolved in ethyl acetate (500 mL). 10% palladium on carbon (1.5 g) was added. The resulting solution was stirred under H$_2$ (1 atm) for 16 h and filtered through a pad of silica gel. Concentration of the filtrate gave the title compound as a liquid.

Characteristic $^1$H NMR (CDCl$_3$, 400 MHz): 11.0 (s, 1H), 7.60 (s, 1H), 3.96(s, 3H), 2.70(symm. m, 2H), 2.59(symm. m, 2H), 1.60–1.72(m, 4H), 1.05(t, J=7.2 Hz, 3H), 1.03(t, J=7.2 Hz, 3H).

Step 2. Preparation of N-Alkyl-4-acetoxy-3,5-dipropyl-6-hydroxybenzohydroxamic acid.

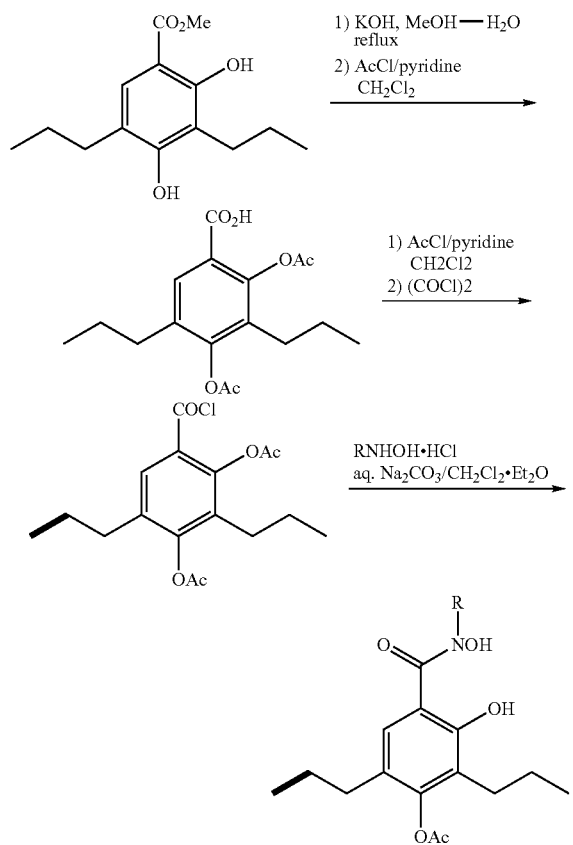

Methyl 2,4-dihydroxy-3,5-dipropylbenzoate (31.6 g, 127 mmol) was dissovled in methanol (500 mL). An aqueous solution of NaOH (2 N, 380 mL, 0.762 mol) was added. After being stirred under reflux for 20 h. the reaction mixture was poured into brine (500 mL), acidified with 2 N HCl to pH 2 and extracted with ethyl acetate. The organic phase was washed with brine, dried over MgSO$_4$ and concentrated. The residue was used without purification.

The crude acid (25.4 g, 108 mmol) and acetyl chloride (25.4 g, 23.0 mL, 324 mmol) were dissolved in methylene chloride (500 mL). Pyridine (34.1 g, 35.0 mL, 432 mmol) was added at 0° C. The reaction mixture was warmed to 25° C. over 1 h and then poured into 0.5 N hydrochloric acid (250 mL). The organic layer was separated and washed with brine. Removal of the solvent give the crude 2,4-diacetoxy-3,5-dipropylbenzoic acid.

The crude acid (4.1 g, 12.7 mmol) was suspended in oxalyl chloride (4.83 g, 3.12 mL, 38.1 mmol). After addition of 2 drops of DMF, the reaction mixture was heated at 60° C. for 1 h. Excess reagent was distilled off under reduced pressure and the residue was azeotroped with toluene (2×20 mL) to afford the crude acid chloride.

The crude acid chloride (1.0 equiv.) was dissolved in methylene chloride (4.0 mL/mmol) and the solution was added to a vigorously stirred biphasic mixture of the appropriate N-alkylhydroxyamine hydrochloride (3.0 equiv.) in diethyl ether (25 mL/mmol) and 2 N aqueous sodium carbonate (4.0 equiv.). After 30 min, the reaction mixture was acidified with 2 N HCl to pH 2 and extracted with ethyl acetate. The organic layer was washed with brine, dried over MgSO$_4$ and concentrated. The residue was purified by chromatography on silica gel eluting with hexane:ethyl acetate (8:2) to give the title compound (R=Me, i-Pr) as brown oil.

R=i-Pr

Characteristic $^1$H NMR(CDCl$_3$, 400 MHz): δ7.02(s, 1H), 4.59(septet, J=6.8 Hz, 1H), 2.36–2.60(m, 4H), 2.38(s, 3H), 1.41–1.56(m, 4H), 1.39 (d, J=6.8 Hz, 6H), 0.98(t, J=7.2 Hz, 3H), 0.96(t, J=7.2 Hz, 3H).

MS(ESI): 338 (M$^+$+1).

R=Me

Characteristic $^1$H NMR(CDCl$_3$, 400 MHz): δ7.05, s, 1H), 3.59(s, 3H), 2.46–2.60(m, 2H), 2.30–2.41(m, 2H), 2.38(s, 3H), 1.41–1.56(m, 4H), 0.98(t, J=7.2 Hz, 3H), 0.96(t, J=7.2 Hz, 3H).

MS(ESI): 310(M$^+$+1).

Step 3. 2,3-dihydro-6-hydroxy-2-methyl-3-oxo-5,7-dipropyl-1,2-benzisoxazole.

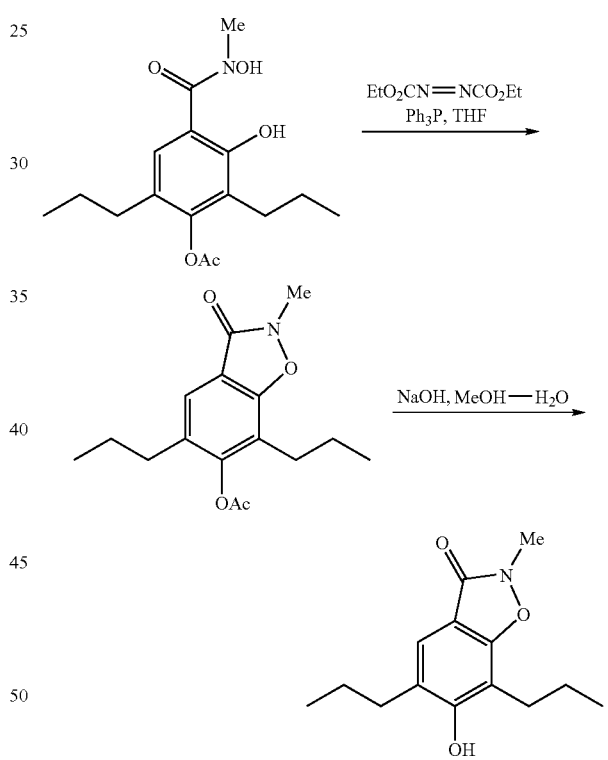

The hydroxamic acid (0.31 g, 1.0 mmol) and triphenyl phosphine (0.39 g, 1.5 mmol) were dissolved in dry THF (10 mL). To the resulting solution was added dropwise diethyl azodicarboxylate (0.26 g, 1.5 mmol). The reaction was stirred at 25° C. for 30 min before it was quenched with methanol:acetic acid (1:1, 0.10 mL). The reaction mixture was concentrated and the residue was loaded onto a silica gel column. Elution with hexane:ethyl acetate (8:2) gave the acetylate title compound as an.

Characteristic $^1$H NMR (CDCl$_3$, 400 MHz): δ7.55(s, 1H), 3.68(s, 3H), 2.40 (s, 3H), 2.80(t, J=7.1 Hz, 2H), 2.73(t, J=7.1 Hz, 2H).

The crude product (0.23 g, 0.80 mmol) was dissolved in methanol (5.0 mL). 2 N sodium hydroxide solution (1.0 mL) was added. After being stirred for 30 min, the reaction mixture was neutralized with 2N hydrochloric acid and evaporated to dryness under reduced pressure. The residue was taken up in ethyl acetate and filtered through silica gel to give the title compound as a solid.

Characteristic ¹H NMR (CDCl₃, 400 MHz): δ7.43(s, 1H), 3.62(s, 3H), 2.77(t, J=7.1 Hz, 2H), 2.63(t, J=7.1 Hz, 2H).
MS(ESI): 250.1(M⁺+1).

Step 4 Preparation of α-[(2,3-dihydro-2-methyl-3-oxo-5,7-dipropyl-1,2-benzisoxazol-6-yl)oxy]-4-(1-methylethyl)benzeneacetic acid.

Characteristic ¹H NMR (CD₃OD, 500 MHz): δ7.45 (d, J=6.7 Hz, 2H), 7.43(s, 1H), 7.40 (d, J=6.7 Hz, 2H), 5.17(s, 1H), 3.62(s, 3H), 2.86(septet, J=7.2 Hz, 1H), 1.24(d, J=7.2 Hz, 6H).

MS(ESI): 426.2(M⁺+1)

Example 12

Step 1. Preparation of 2,3-dihydro-6-hydroxy-3-(1-methylethyl)-2-oxo-5,7-dipropyl-1,3-benzoxazole.

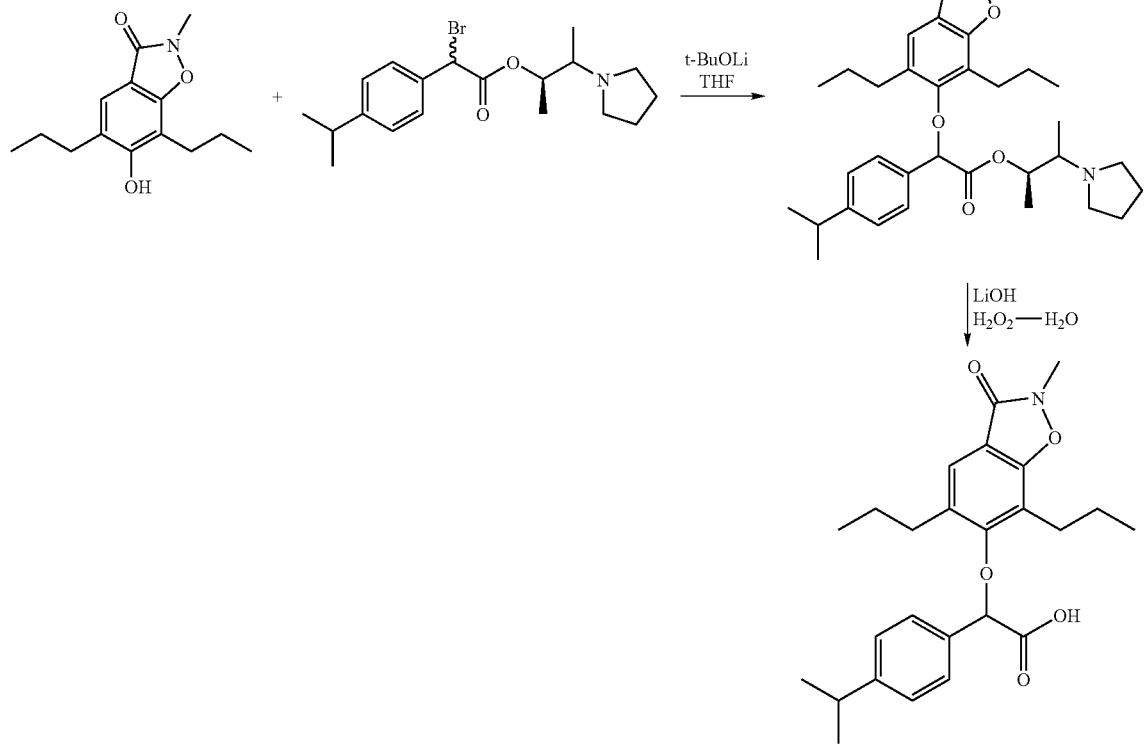

The phenol of step 3 (0.20 g, 0.80 mmol) was coupled with the indicated bromide (0.3 g, 0.80 mmol) as was described for example 6, step 1. The product was purified by chromatography on silica gel eluting with ethyl acetate: hexane (50:50).

Characteristic ¹H NMR (400 MHz, CDCl₃): δ7.45 (s, 1H), 7.40 (d, J=6.7 Hz, 2H), 7.25(d, J=6.7 Hz), 5.28 (s, 1H), 5.27 (q, J=7.1 Hz, 1H), 3.62(s, 3H), 2.95(septet, J=7.2 Hz, 1H) 1.37(d, J=7.1 Hz, 3H), 1.24(d, J=7.2 Hz, 6H).
MS(ESI): 573.1(M+Na⁺).

The coupling product (0.42 g, 0.72 mmol) was hydrolyzed under conditions similar to those described for example 6, step 2. The product was purified by preparative HPLC on a YMC-pack C8 column with CH₃CN:H₂O (10:90 to 100:0, 15 min gradient) containing 0.1% TFA as eluent.

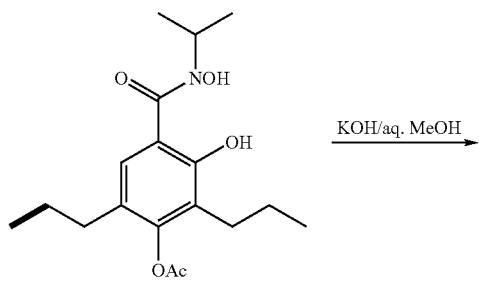

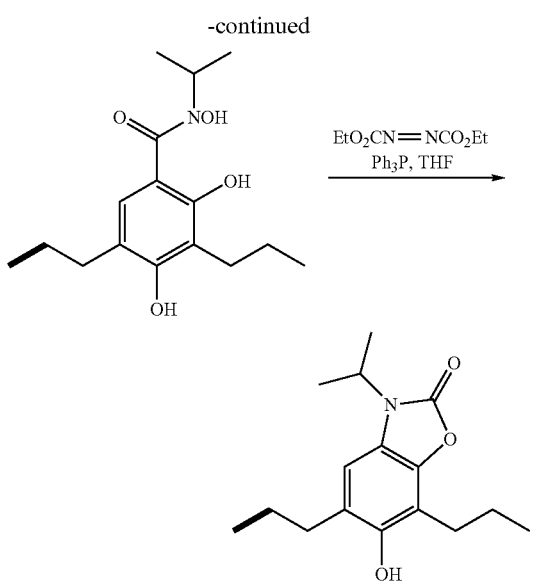

The N-isopropylhydroxamic acid of example 11 step 2 (1.0 g, 3.0 mmol) was dissolved in methanol (30 mL). 2 N KOH solution was added (5 mL). After being stirred at 25° C. for 30 min the reaction mixture was acidified with 2 N hydrochloric acid to pH 2 and extracted with ethyl acetate (2×20 mL). The organic phase was washed with brine, dried and concentrated. The residue was purified by chromatography on silica gel eluting with hexane-ethyl acetate (7:3) to give the deacetylated product as a brown oil.

The deacetylated product (0.74 g, 2.4 mmol) was mixed with triphenylphosphine (0.94 g, 3.6 mmol) in dry THF (20 mmol). Diethyl azodicarboxylate (0.63 g, 3.6 mmol) was added dropwise. The reaction mixture was stirred for 30 min before it was quenched with methanol:acetic acid (1:1, 0.1 mL). The solvent was evaporated and the residue was subjected to chromatography on silica gel eluting with hexane:ethyl acetate (7:3) to give the title compound as an oil.

Characteristic $^1$H NMR (CD$_3$OD, 500 MHz): δ6.82(s, 1H), 4.47(septet, J=6.8 Hz, 1H), 1.50(d, J=6.8 Hz, 6H).

MS(ESI): 278.1 (M$^+$+1).

Step 2 Preparation of α-[(2,3-dihydro-3-(1-methylethyl)-2-oxo-5,7-dipropyl-1,3-benzoxazol-6-yl)oxy]4-(1-methylethyl)benzeneacetic acid.

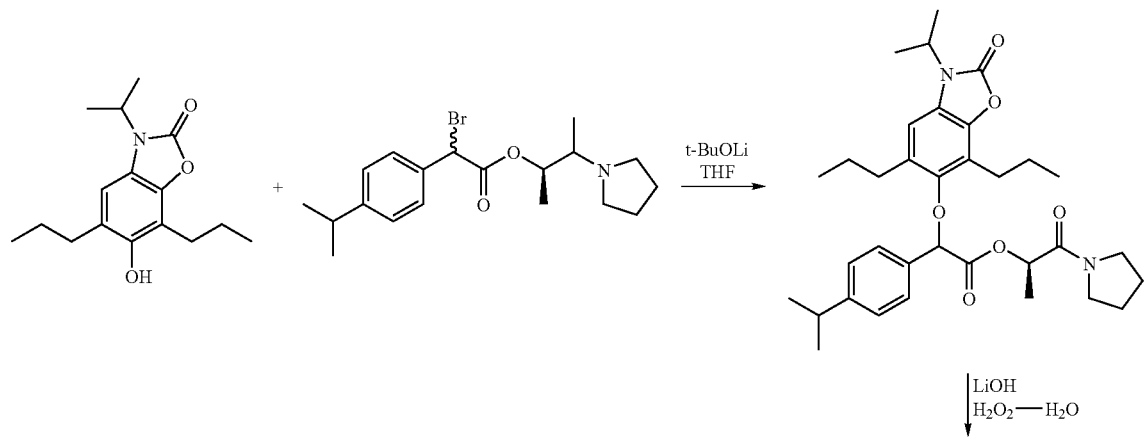

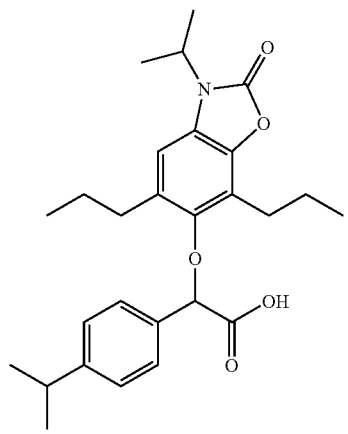

The phenol of step 1 (0.28 g, 1.0 mmol) was coupled with the indicated bromide(0.38 g, 1.0 mmol) as for example 6, step 1. The product was purified by chromatography on silica gel eluting with ethyl acetate:hexane (50:50).

Characteristic $^1$H NMR (CD$_3$Cl$_3$, 500 MHz): δ7.40(d, J=6.7, 2H), 7.22(d, J=6.7 Hz, 2H), 6.70(s, 1H), 5.25 (q, J=7.1 Hz, 1H), 5.15 (s, 1H), 4.50(septet, J=7.0 Hz, 1H), 2.95(septet, J=7.2 Hz, 1H) 1.52(d, J=7.0 Hz, 6H), 1.37(d, J=7.1 Hz, 3H), 1.23(d, J=7.2 Hz, 6H).

MS(ESI): 578.2(M$^+$+1)

The coupling product (0.50 g, 0.88 mmol) was hydrolyzed under conditions similar to those described for example 6, step 2. The product was purified by preparative HPLC on a YMC-pack C8 column CH$_3$CN:H$_2$O (10:90 to 100:0, 15 min gradient) containing 0.1% TFA as eluent.

Characteristic $^1$H NMR (CD$_3$OD, 500 MHz): δ7.40 (d, J=6.7 Hz, 2H), 7.28(d, J=6.7 Hz, 2H), 6.92 (s, 1H), 5.05(s, 1H), 4.50(septet, J=7.0 Hz, 1H), 2.95(septet, J=7.2 Hz, 1H), 1.50(d, J=7.0 Hz, 6H), 1.25(d, J=7.2 Hz, 6H)

MS(ESI): 453.1 (M$^+$+1)

Example 13

Step 1 Preparation of 2,4-Dihydroxy-3,5-dipropylpropiophenone.

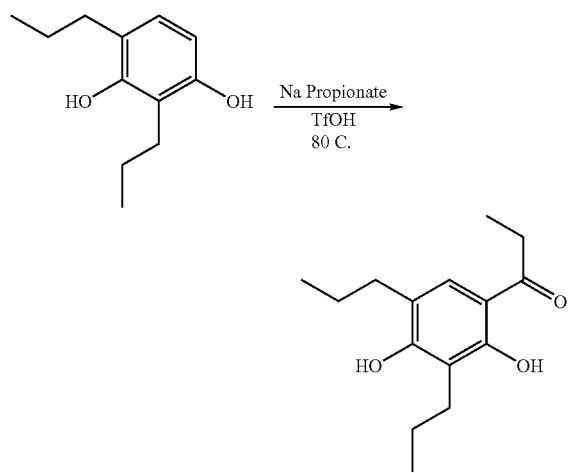

The 2,6-bis-allylresorcinol (5.0 gm, 1.0 Eq) was dissolved in trifluoromethanesulfonic acid (25 ml) with sodium propionate (2.96 gm, 1.2 Eq). The mixture was heated to 85° C. for 1½ Hrs and then cooled to RT. The mixture was diluted with H$_2$O and ethyl acetate. The phases were separated and the aqueous phase extracted again with EtOAc. The EtOAc extracts were washed with saturated aq NaCl, dried over MgSO$_4$ and reduced i. vac.

The product was purified by elution from a silica gel column (200 g E. Merck 40–63μ) with hexanes:EtOAc 96:4.

Characteristic NMR Resonances; $^1$H NMR 400 MHz (CDCl$_3$); 7.40 (s, 1H), 5.29 (s, 1H), 2.98 (q, 2H, J=7.4 Hz), 2.64 (dd, 2H, J=6.3, 7.7 Hz), 2.55 (collapsed dd, 2H, J obscured), 1.6 (m, 4H), 1.25 (t, 3H, J=7.4 Hz), 1.003 (t, 3H, J=7.4 Hz), 0.999 (t, 3H, J=7.4 Hz).

Step 2 Preparation of Methyl α-[3-hydroxy-4-(1-oxopropyl)-2,6-dipropylphenoxy]benzeneacetate.

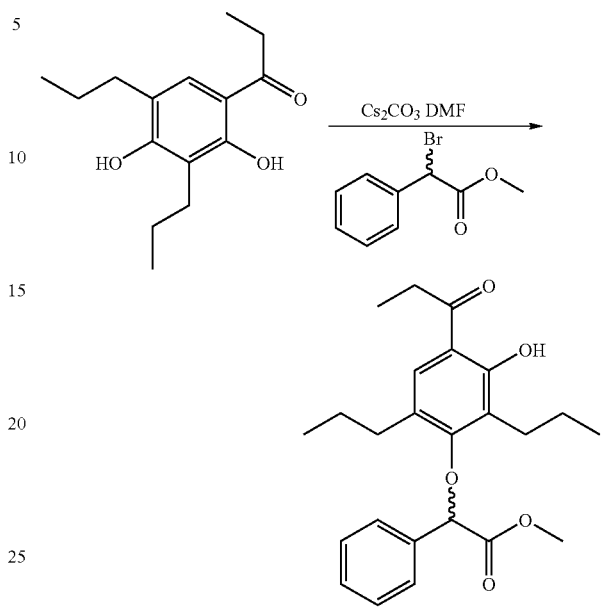

The phenol of step 1 (12 gm, 1.0 Eq) was coupled with commercially available methyl 2-bromo-2-phenylacetate (11.5 gm, 1.05 Eq) as for example 1, step 4. The product was purified by elution from a silica gel column (700 g E. Merck 40–63μ) with hexanes:EtOAc 96:4.

Characteristic NMR Resonances; $^1$H NMR 400 MHz (CDCl$_3$); 7.51–7.53 (m, 2H), 7.42 (m, 3H), 5.24 (s, 1H), 3.77 (s, 3H), 2.99 (q, 2H, J=7.3 Hz), 2.48 (m, 2H), 2.36 (m, 2H), 1.53 (m, 4H), 1.24 (t, 3H, J=7.3 Hz), 0.848 (t, 3H, J=7.3 Hz), 0.835 (t, 3H), J=7.3 Hz).

Step 4 Preparation of α-[3-hydroxy-4-(1-oxopropyl)-2,6-dipropylphenoxy]benzeneacetic acid

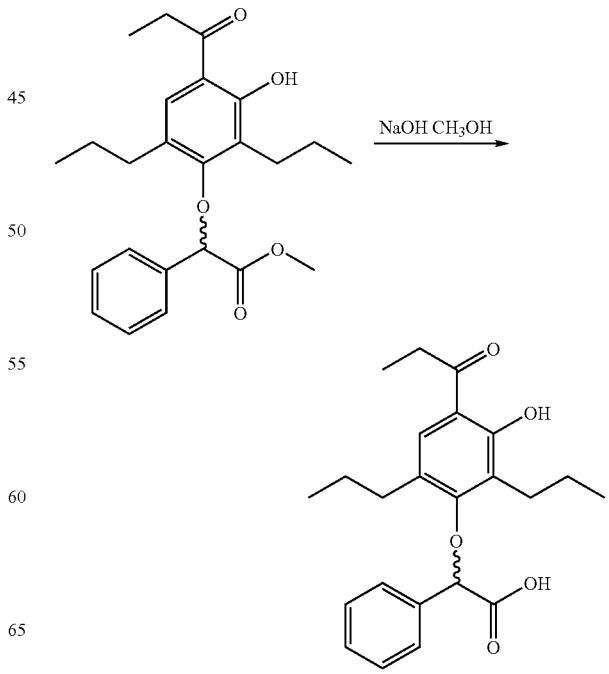

The ester of step 2 (18.6 gm) was hydrolyzed with NaOH (98 ml) as for example 1, step 5.

The product was purified by elution from a silica gel column (700 g E. Merck 40–63µ) with hexanes:EtOAc:AcOH 88:10:2. The resulting oil was crystallized from hexanes to give the titled compound.

Characteristic NMR Resonances; ¹H NMR 400 MHz (CDCl₃); 7.50 (m, 2H), 7.42 (m, 3H), 5.26 (s, 1H), 2.99 (q, 2H, J=7.3 Hz), 2.45 (m, 2H), 2.32 (m, 2H), 1.45 (m, 4H), 1.24 (t, 3H, J=7.3 Hz), 0.824 (t, 3H, J=7.3 Hz), 0.814 (t, 3H, J=7.2 Hz).

Example 14

Step 1 Preparation of 2,6-dipropyl-4-propionylphenol

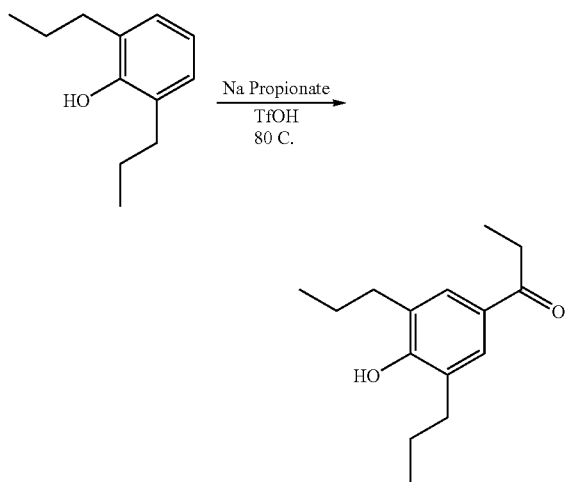

Sodium propanoate (0.88 g, 1.5 eq) and 2,6-dipropylphenol (1.09 g, 1.0 eq) were combined in Triflic Acid (5.0 g) as in Example 13, step 1. The resulting waxy solid was purified by chromatography on silica gel using ethyl acetate:hexanes:acetic acid (10:90:1) to give the titled phenol.

Characteristic NMR Resonances; ¹H NMR 500 MHz (CDCl₃); 7.66 (s, 2H), 5.19 (s, 1H, phenol OH), 2.96 (q, 2H, J=7.3), 2.62 (t, 4H, J=7.7 Hz), 1.68 (m, 4H), 1.22 (t, 3H, J=7.3 Hz), 1.01 (t, 6H, J=7.3 Hz)

MS (ESI): (M+H)=235.1.

Step 2 Preparation of Methyl α-[4-(1-oxopropyl)-2,6-dipropylphenoxy]benzeneacetate.

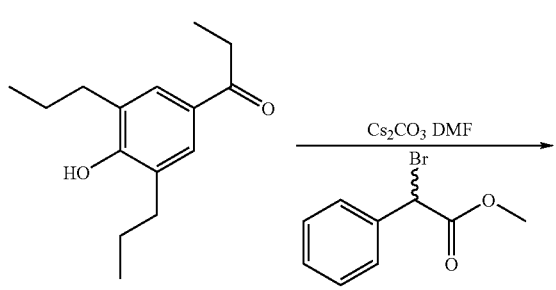

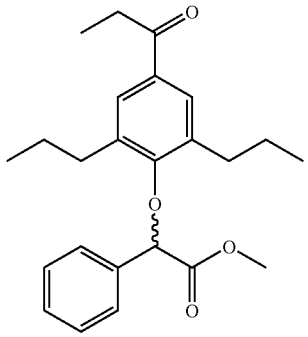

Methyl 2-bromo-2-phenylacetate (0.95 eq), Cs₂CO₃ (1.20 eq) and the indicated phenol (1.0 eq) were combined in 1.5 ml DMF at 50° C. The mixture was stirred for 1.5 Hrs. The suspension was then cooled and poured into 10% citric acid solution and extracted with ethyl acetate. The organic phase was separated and washed with water followed by brine. The organic phase was then dried over magnesium sulfate and the solvent was evaporated i. vac. to give an oil. The resulting oil was purified by chromatography on silica gel using ethyl acetate:hexanes (10:90) to give the titled compound.

Step 3 Preparation of racemic α-[4-(1-oxopropyl)-2,6-dipropylphenoxy]benzeneacetic acid.

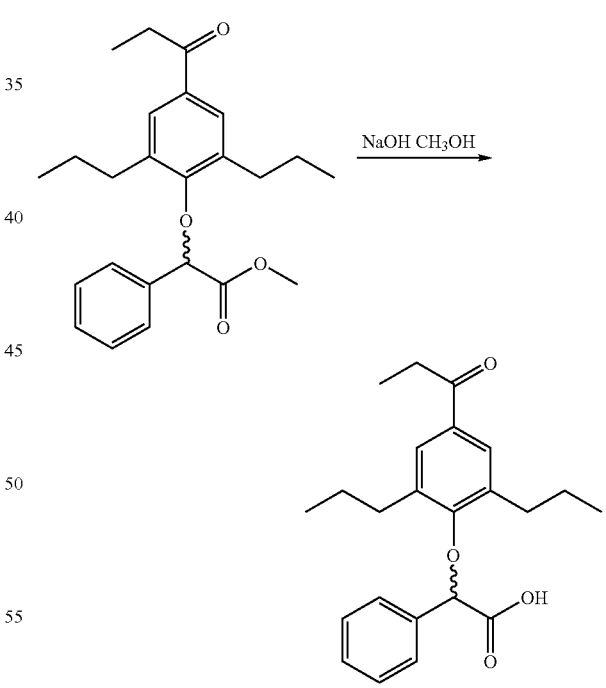

The title acid was prepared as for example 1, step 5 from the indicated ester (30.0 mg, 1.0 eq) and 2 N KOH (1.1 eq). After work-up, the resulting oil was purified by chromatography on a Zorbax C8 RP (21.2×250 mm) HPLC column eluting with 70:30 water:acetonitrile (0.1% TFA) to give the titled compound as an oil.

Characteristic NMR Resonances; ¹H NMR 500 MHz (CD₃OD); 7.65 (s, 2H), 7.49 (m, 2H), 7.40 (m, 3H) 5.18 (s, 1H) 2.99 (q, 2H, J=7.3 Hz), 2.44 (m, 4H), 1.51 (m, 4H) 1.15 (t, 3H, J=7.3 Hz) 0.83 (t, 6H, J=7.3 Hz).

MS (ESI): (M+H)=369.1, (M+Na)=391.1

Example 15

Step 1 Preparation of Methyl 2-Bromo-2(4-(1-methylethyl)phenyl)acetate.

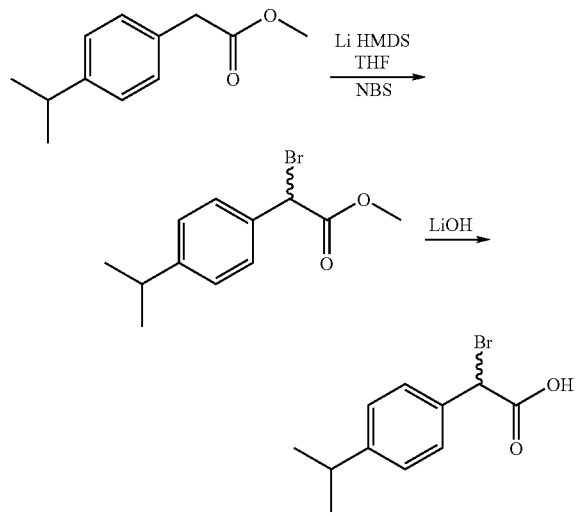

Commercially available 4-isopropylphenylacetic acid (1 gram) was dissolved in ether (20 mL). Diazomethane was added until the reaction mixture remained yellow. The crude reaction mixture was cooled to −78° C. in THF (50 mL). Lithium bis (trimethylsilyl) amide (7.05 mL, 1.1 eq) was added to the reaction and stirred for 20 minutes. Chlorotrimethylsilane (1.52 mL, 1.875 eq) was added at −78° C. and stirred for 20 minutes. N-bromosuccinimide (1.20 g, 1.05 eq) was added to the reaction mixture. The reaction mixture was allowed to stir and warm to room temperature overnight. The reaction mixture was diluted with H₂O. The aqueous layer was extracted with ethyl acetate. The organic phase was dried over sodium sulfate and the solvent was evaporated to give yellow oil. The resulting oil was chromatographed on silica gel using hexanes and ethyl acetate (95:5) to give methyl 2-bromo-2-(4-(1-methylethyl)phenyl) acetate.

Characteristic NMR Resonances; ¹H NMR 500 MHz (CDCl₃); 7.46–7.56 (m, 2H), 7.22–7.26 (m, 2H), 5.39 (s, 1H), 3.80 (s, 3H), 2.93 (m, 1H), 1.26 (d, 6H)

The methyl ester (0.052 moles) and 1 N LiOH (0.053 moles) was stirred at 0° C. for 1H. The reaction was then acidified with 2 N HCl (pH=2) and partitioned between ethyl acetate/water. The organic phase was separated and washed with water followed by brine. The organic phase was then dried over magnesium sulfate and the solvent was evaporated i. vac. to give an oil which became crystalline i. vac. The α-bromo acid was used in the following condensation without purification.

Characteristic NMR Resonances; ¹H NMR 500 MHz (CD₃OD); 7.46 (d, 2H, J=8.0 Hz), 7.23 (d, 2H, J=8.3 Hz) 5.48 (s, 1H) 2.90 (m, 1H) 1.24 (d, 6H, J=6.9 Hz)

Step 2 Preparation of 2-Bromo-2-(4-(1-methylethyl)phenyl) acetate (R)Pyrrolidinelactamide ester.

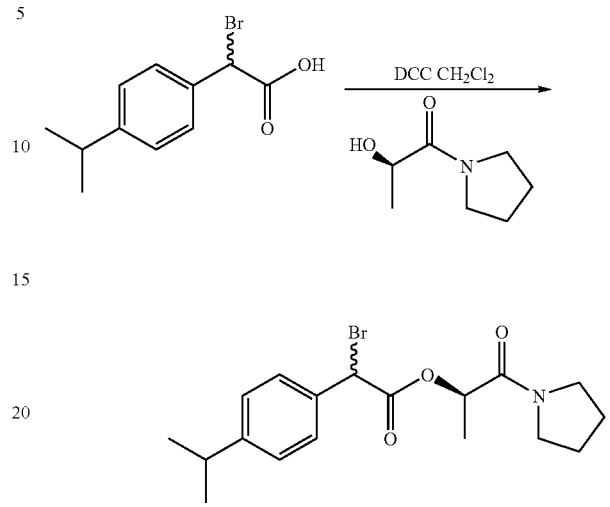

The acid from step 1 (0.053 moles) was treated with DCC (1.1 equiv., 1.0M in dichloromethane) and DMAP (0.05 equiv.) in dry dichloromethane at 0° C. as described in Tet Let 37, 2683–2686, 1996 and references cited therein. After work-up, the reaction mixture was purified on silica gel using ethyl acetate:hexanes:acetic acid (30:70:1) as eluent. The product is an approximately one to one mixture of diastereomers.

Characteristic NMR Resonances; ¹H NMR 500 MHz (CD₃OD); 7.48 (d, 0.5×2H, J=8.2 Hz), 7.47 (d, 0.5×2H, J=8.3 Hz), 7.24 (d, 0.5×2H, J=8.2 Hz), 7.23 (d, 0.5×2H, J=8.3 Hz), 5.64 (s, 0.5×1H), 5.62 (s, 0.5×1H) 5.26 (m, 1H), 3.32–3.64 (m, 4H), 2.90 (m, 1H) 1.82–2.02 (m, 4H), 1.44 (d, 0.5×3H, J=6.6 Hz), 1.38 (d, 0.5×3H, J=6.6 Hz), 1.24 (d, 6H, J=6.9 Hz)

MS (ESI): (M+Na)=558.3

Alternate Preparation of Pyrrolidine-lactamide Ester of α-Bromo-(p-(isdpropylphenyl)acetic Acid Step 1a. Preparation of (R) Pyrrolidine Lactamide

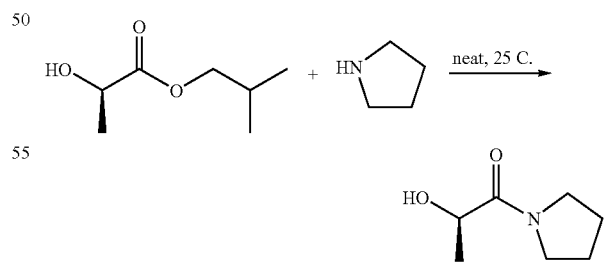

A mixture of commercially available (R)-(+)-isobutyl lactate (25 mL, 166 mmol) and pyrrolidine (23.61 g, 27.7 mL, 332 mmol) were kept at 25° C. for 3 days. The reaction mixture was evaporated i. vac. The residued was azeotroped with toluene (2×100 mL) to give title compound as a brown liquid.

Step 2a Preparation of 2-oxo-2-(4-(1-methylethyl)phenyl)acetic (R)Pyrrolidinelactamide ester.

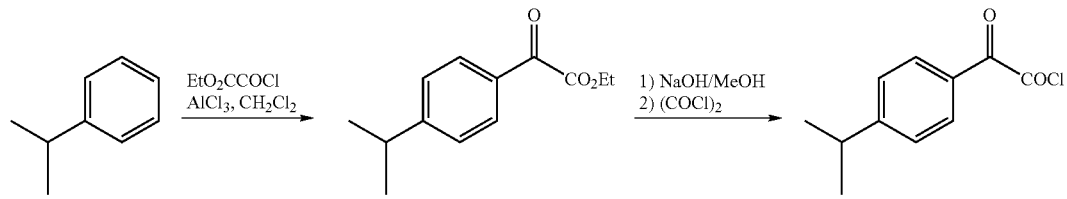

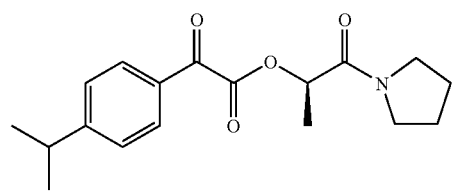

At 25° C., aluminum trichloride (26.7 g, 0.20 mmol) was added to a solution of isopropylbenzene (24.0 g, 0.20 mole) and ethyl chlorooxoacetate (41.0 g, 0.30 mol) in dry methylene chloride (0.50 L). The resulting mixture was stirred at 25° C. for 2 h and then poured into 0.5 N hydrochloric acid (0.50 L). The organic layer was separated and the aqueous phase was extracted with methylene chloride (2×200 mL). The combined organic layers were washed successively with brine (1×300 mL) and saturated sodium bicarbonate (1×300 mL) and dried over $MgSO_4$. Removal of all volatiles i. vac. gave the α-keto ester, which was used without purification. The crude keto ester (25.0 g, 114 mmol) was dissolved in methanol (0.50 L). 2 N sodium hydroxide (83.0 mL) solution was added. After being stirred for 30 min., the reaction mixture was diluted with water (0.50 L), acidified with 2 N hydrochloric acid to pH 2 and extracted with ethyl acetate (3×250 mL). The extracts were washed with brine (2×250 mL), dried over $MgSO_4$ and concentrated. The crude keto acid (23.0 g) was used without purification.

The crude keto acid (4.6. g, 22.8 mmol) was dissolved in dry methylene chloride (20 mL). Oxalyl chloride (5.78 g, 4.0 mL, 45.6 mmol) was added followed by addition of 1 drop of dimethylformamide. The reaction mixture was stirred at 25° C. for 30 min and heated under reflux for another 30 min. After all volatiles were distilled off, the residue was azeotroped with toluene (1×100 mL) under reduced presure to give the crude acid chloride.

The crude acid chloride (ca. 4.6 g, 21.8 mmol) was mixed with pyrrolidine (R)-lactamide (3.12 g, 21.8 mmol) in dry methylene chloride (100 mL). The resulting solution was cooled to 0° C., and triethylamine (4.4 g, 6.06 mL, 43.6 mmol) was added dropwise. The reaction mixture was left stirring at 25 C for 30 min and then poured into 0.5 N hydrochloric acid (50 mL). The organic layer was separated and the aqueous phase was extracted with methylene chloride (2×50 mL). The combined organic phases were washed with brine, dried over $MgSO_4$ and concentrated. The residue was subjected to chromatography on silica gel eluting with hexane:ethyl acetate (1:1) to give pure title compound as a solid.

Characteristic $^1H$ NMR (CDCl3, 400 MHz) δ8.1 (d, J=6.0 Hz, 2H), 7.31(d, J=6.0 Hz, 2H), 5.39 (q, J=7.0 Hz, 1H), 3.20 (m, 1H), 1.60 (d, J=7.0 Hz. 3H), 1.26 (d, J=7.2 Hz, 6 h)

Step 3a. Preparation of 2-Bromo-2-(4-(1-methylethyl)phenyl)acetate (R)Pyrrolidinelactamide ester.

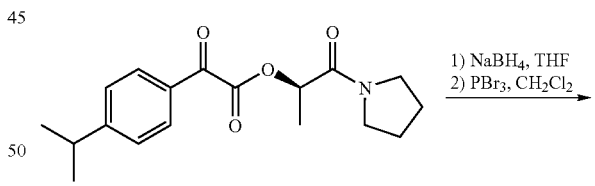

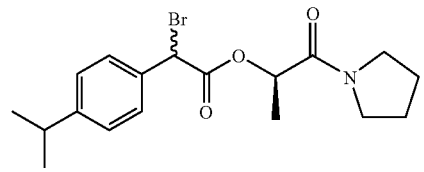

To a solution of the lactamide keto ester (5.08 g, 16.0 mmol) in dry THF (100 mL) cooled at 0° C. was added sodium borohydride (0.302 g, 8.0 mmol). The reaction mixture was stirred at 0° C. for 30 min and then poured into a cold mixture of brine (50 mL) and 2 N hydrochloric acid (4 mL). The organic layer was separated and the aqueous-phase was extracted with ethyl acetate (3×50 mL). The combined organic layers were washed with brine (1×50 mL), dried and concentrated. The residue (ca 4.6 g) was used directly for the next step.

The crude product (ca. 4.6 g, 14.5 mmol) was dissolved in dry methylene chloride (50 mL) at 25° C. Phosphorus tribromide (3.92 g, 1.37 mL, 14.5 mmol) was added. The reaction mixture was stirred at 25° C. for 30 min and then poured into brine (100 mL). The organic phase was separated and the aqueous phase was extracted with methylenechloride (2×50 mL). The combined organic phases were washed with brine, dried over MgSO$_4$ and concentrated. The residue was purified by chromatography on silica gel eluting with hexane:ethyl acetate (1:1) to give the title compound as a 1:1 mixture of diastereoisomers.

Characteristic $^1$H NMR (CDCl$_3$, 500 MHz): δ5.42 (s, 1H), 5.29 (q, J=7.0 Hz, 0.5×1H), 5.27 (q, J=7.0 Hz, 0.5×1H), 2.9 (m, 1H), 1.50 (d, J=7.0 Hz, 0.5×3H), 1.45 (d, J=7.0 Hz, 0.5×3H), 1.25 (d, J=7.2 Hz, 0.5×6H), 1.24 (d, J=7.2 Hz, 0.5×6H).

Step 3 Preparation of α-[4-(1-oxopropyl)-2,6-dipropylphenoxy]benzeneacetic acid (R)Pyrrolidinelactamide ester.

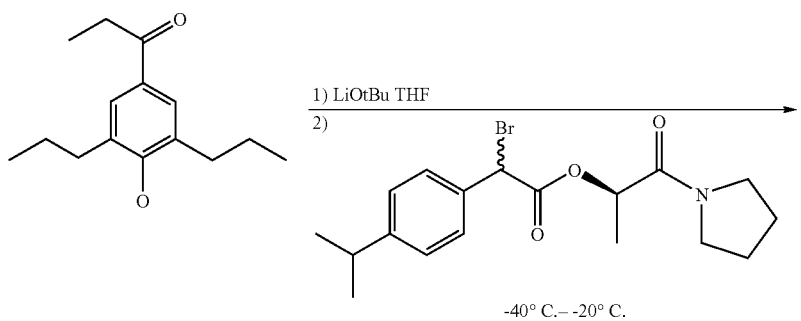

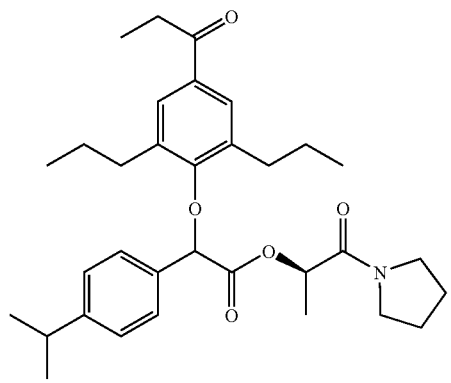

The bromide described immediately above (0.045 moles) and 1.05 equiv. of the phenol from Example 14 Step 1 were combined as in Example 6 Step 1. After work-up, the reaction mixture was purified by chromatography on silica gel using acetone:hexanes (20:80) as eluent to give the titled compound.

Characteristic NMR Resonances; $^1$H NMR 500 MHz (CD$_3$OD); 7.64 (s, 2H), 7.39 (d, 2H, J=8.0 Hz), 7.28 (d, 2H, J=8.1 Hz), 5.32 (s, 1H), 5.27 (q, 1H, J=6.9 Hz), 3.72 (m, 1H), 3.61 (m, 1H), 3.35–3.50 (m, 4H), 2.98 (q, 2H, J=7.2 Hz), 2.93 (m, 1H), 2.41 (m, 4H), 1.93 (m, 2H), 1.86 (m, 3H), 1.53 (m, 2H), 1.42 (m, 2H), 1.32 (d, 3H, J=6.9 Hz), 1.25 (d, 6H, J=6.9 Hz), 1.15 (t, 3H, J=7.3 Hz), 0.80 (t, 6H, J=7.3 Hz).

Step 4 Preparation of 2-(2,6-dipropyl-4-propionylphenoxy)-2-phenylacetic acid.

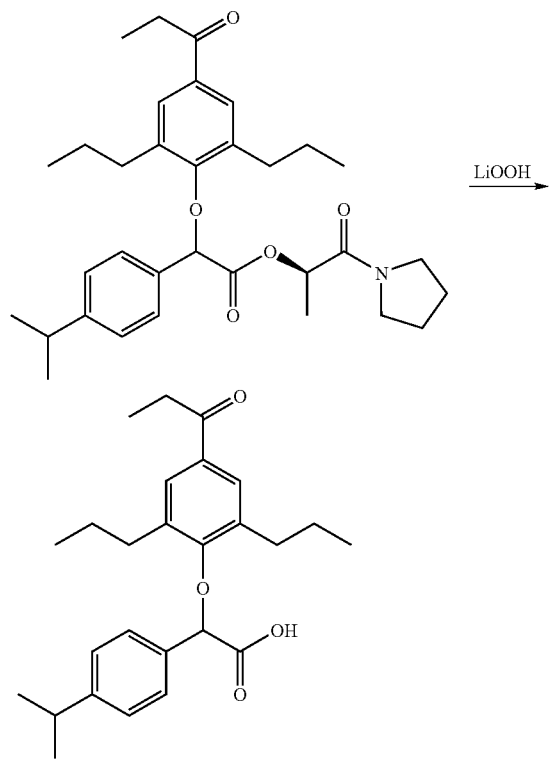

The ester from step 3 (0.033 moles) was treated with 2.1 equiv. 1 N LiOH pre-mixed with 30% hydrogen peroxide (51.0 ml.) and added at 0° C. as per Example 6 Step 2. After work-up, the reaction mixture was purified by chromatography on silica gel using ethyl acetate:hexanes:acetic acid (30:70:1) as eluent to give the titled acid. Enantiomeric purity was determined by HPLC using a Cyclobond 2000 column (4.6×250 mm) and a solvent system of methanol:acetonitrile:acetic acid (20:80:1) at a flow rate of 1.5 ml/min.

Characteristic NMR Resonances; $^1$H NMR 500 MHz (CD$_3$OD); 7.64 (s, 2H), 7.38 (d, 2H, J=8.2 Hz), 7.27 (d, 2H, J=8.2 Hz), 5.13 (s, 1H), 2.99 (q, 2H, J=7.2), 2.92 (m, 1H), 2.42 (m, 4H), 1.53 (m, 2H), 1.43 (m, 2H), 1.26 (d, 6H, J=6.8 Hz), 1.15 (t, 3H, J=7.2 Hz), 0.82 (t, 6H, J=7.3 Hz).

MS (ESI): (M+H)=411.2, (M+Na)=433.3

Example 16

Step 1 Preparation of Methyl 2-Bromo-2-(4-(1-methylethoxy)phenyl)acetate.

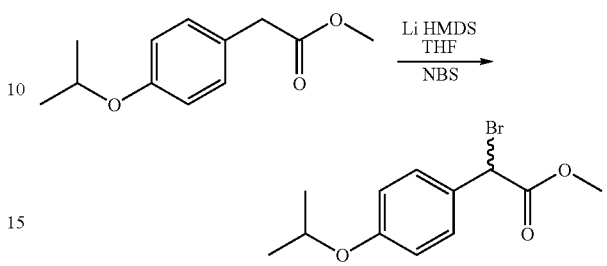

Methyl (4-hydroxyphenyl)acetate (1.0 g, 1.0 eq), Cs$_2$CO$_3$ (2.15 g, 1.1 eq) and 2-bromopropane (0.565 mL. 1.0 eq) were combined in 100 ml DMF at room temperature. The mixture was stirred overnight. The suspension was poured into 50 mL 1 N HCl and extracted with ethyl acetate. The organic phase was separated and washed with water followed by sodium bicarbonate. The organic phase was dried over sodium sulfate and the solvent was evaporated to give an oil. The resulting oil was chromatographed on silica gel using hexanes and ethyl acetate (95:5) to give methyl (4-(1-methylethoxy)phenyl)acetate.

Characteristic NMR Resonances; $^1$H NMR 500 MHz (CDCl$_3$); 6.84 (d, 2H), 7.21 (d, 2H), 5.58 (m 1H), 3.65 (s, 3H), 3.59(s, 2H), 2.36(d, 6H)

Step 2 Preparation of Methyl α-[4-(1-oxopropyl)-2,6-dipropylphenoxy]-4-(1-methylethoxy)benzeneacetate.

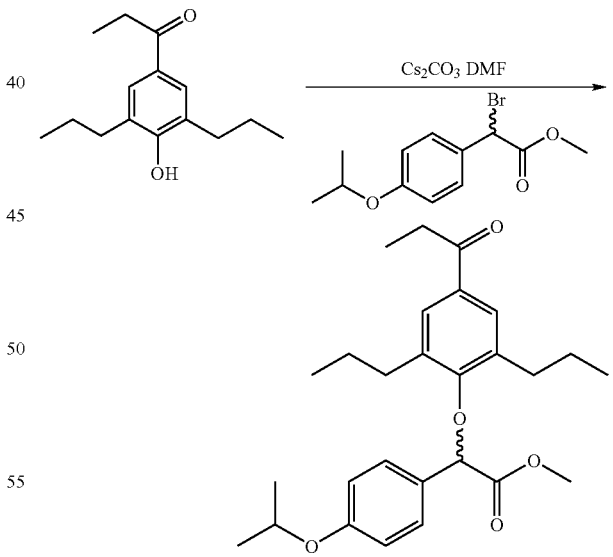

The bromide (0.094 mmoles) described in step 1, Cs$_2$CO$_3$ (1.20 eq) and the phenol from Example 14 step 1 (1.0 eq) were combined in 1.5 ml DMF at 50° C. The mixture was stirred for 1.5 Hrs. The suspension was then cooled and poured into aqueous 10% citric acid solution and extracted with ethyl acetate. The organic phase was separated and washed with water followed by brine. The organic phase was then dried over magnesium sulfate and the solvent was evaporated to give an oil. This crude ester was then used in the following hydrolysis without purification.

Step 3 Preparation of α-[4-(1-oxopropyl)-2,6-dipropylphenoxy]-4-(1-methylethoxy)benzeneacetic acid.

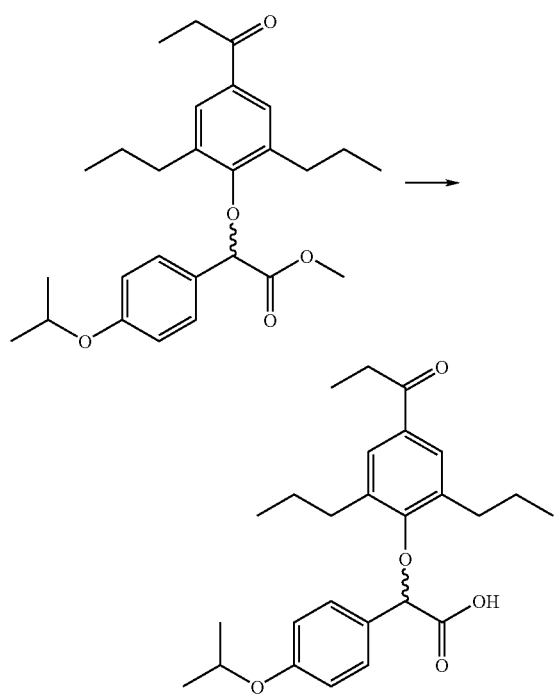

The title acid was prepared as for example 1, step 5 from the indicated ester (60.0 mg, 1.0 eq) and 2 N LiOH (1.1 eq) in 1:1 THF:methanol. After work-up, the resulting oil was purified by chromatography on a Zorbax C8 RP (21.2×250 mm) HPLC column eluting with 70:30 water:acetonitrile (0.1% TFA) to give the titled compound Characteristic NMR Resonances; $^1$H NMR 500 MHz (CD$_3$OD); 7.64 (s, 2H), 7.35 (d, 2H, J=8.7 Hz), 6.91 (d, 2H, J=8.7 Hz), 5.10 (s, 1H), 2.99 (q, 2H, J=7.2), 2.43 (t, 4H, J=8.0), 1.55 (m, 2H), 1.47 (m, 2H), 1.31 (d, 6H, J=6.0 Hz), 1.15 (t, 3H, J=7.2 Hz), 0.84 (t, 6H, J=7.3 Hz).

MS (ESI): (M+Na)=449.1

Example 17

Step 1 Preparation of 3-Fluoro-2,6-dipropyl-4-propionylphenol

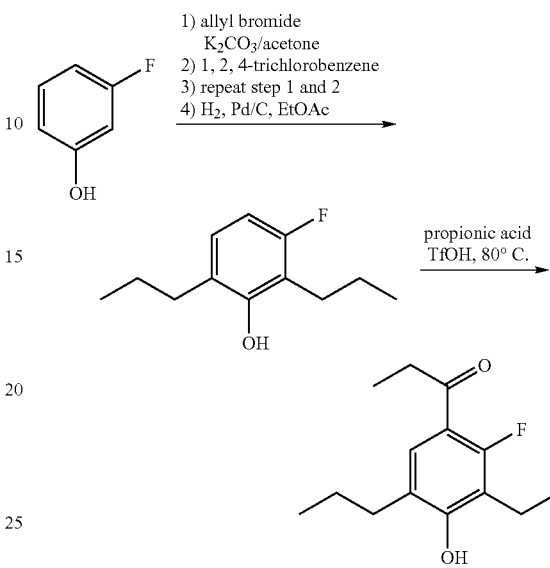

Commercially available 3-fluorophenol(11.2 g, 100 mmol) was subjected twice to the reaction sequence described in Example 11, step 1. The product, 3-fluoro-2,4-dipropylphenol, was purified by chromatography on silica gel using ethyl acetate:hexane(10:90) as eluent.

Characteristic $^1$H NMR (CDCl$_3$, 400 MHz): δ6.92 (dd, J=8.2, 6.4 Hz, 1H), 6.59(dd, J=8.2, 8.3 Hz, 1H), 4.79(s, 1H), 2.62(td, J=7.1, 1.5 Hz, 2H), 2.55(t, J=7.1 Hz, 2H), 1.69–1.80 (m, 4H), 0.99(t, J=7.2 Hz, 6H).

Propionic acid (9.07 g, 123 mmol) and 3-fluoro-2,4-dipropylphenol (9.60 g, 49.0 mmol) were mixed in trifluoromethanesulfonic acid (50 mL) as in Example 13, step 1. Purification by chramotography on silica gel using ethyl acetate:hexane (10:90) gave the title compound as a white solid.

Characteristic $^1$H NMR (CDCl$_3$, 400 MHz): δ7.41 (dd, J=8.2, 6.4 Hz, 1H), 6.59 (dd, J=8.2, 8.3 Hz, 1H), 4.97(s, 1H), 2.98(q, J=7.1 Hz, 2H), 2.62(dt, J=7.1, 1.5 Hz, 2H), 2.55 (t, J=7.1 Hz, 2H), 1.69–1.80 (m, 4H), 1.22 (t, J=7.3 Hz, 3H), 0.99 (t, 6H, J=7.3 Hz)

MS (ESI): (M$^+$+H)=253.1

Step 2 Preparation of α-[3-fluoro-4-(1-oxopropyl)-2,6-dipropylphenoxy]-4(1-methylethyl)benzeneacetic acid.

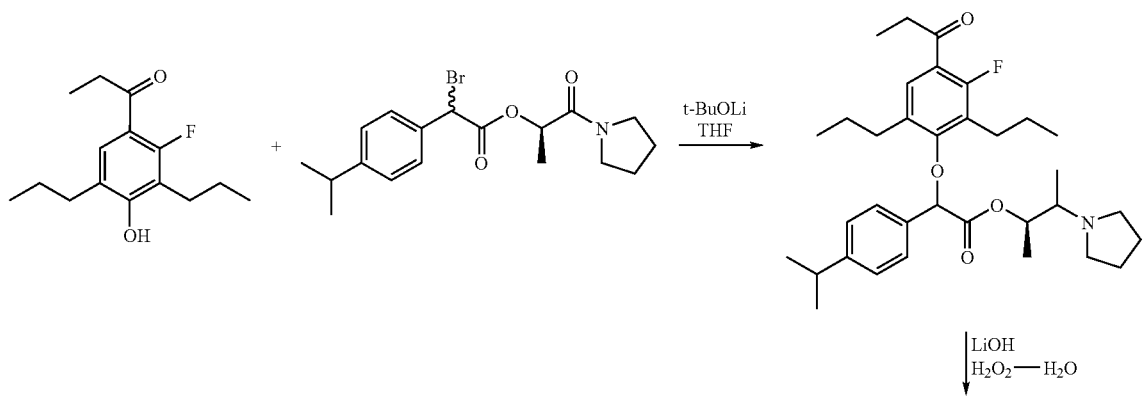

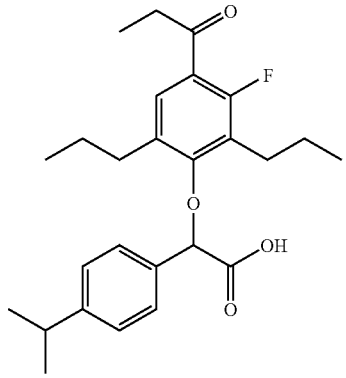

The indicated fluorophenol (0.252, 1.00 mmol) and the indicated bromide (0.382 g, 1.00 mmol) were coupled as was described for example 6, step 1. The coupling product was hydrolysed under conditions similar to those described for example 6, step 2. The crude product was purified by HPLC on a YMC-pack C8 column with $CH_3CN:H_2O$ (10:90 to 100:0, 15 min gradient) containing 0.1% TFA as eluent.

Characteristic $^1H$ NMR ($CD_3OD$, 500 MHz ): δ7.58 (d, J=8.2 Hz, 1H), 7.41(d, J=7.6 Hz, 2H), 7.24(d, J=7.6 Hz, 2H), 5.17(s, 1H), 2.99(q, J=7.2 Hz, 2H), 2.32–2.45 (m, 4H), 1.43–1.57(m, 2H), 1.33–1.47(m, 2H), 1.26 (d, J=6.8 Hz, 3H), 1.15(t, J=7.3 Hz, 3H), 0.82 (t, J=7.3 Hz, 6H)

MS (ESI): 429.2($M^+$+1).

Example 18

Step 1 Preparation of α-[[5,7-dipropyl-3-(trifluoromethyl)-1,2-benzisoxazol-6-yl]oxy]benzeneacetamide.

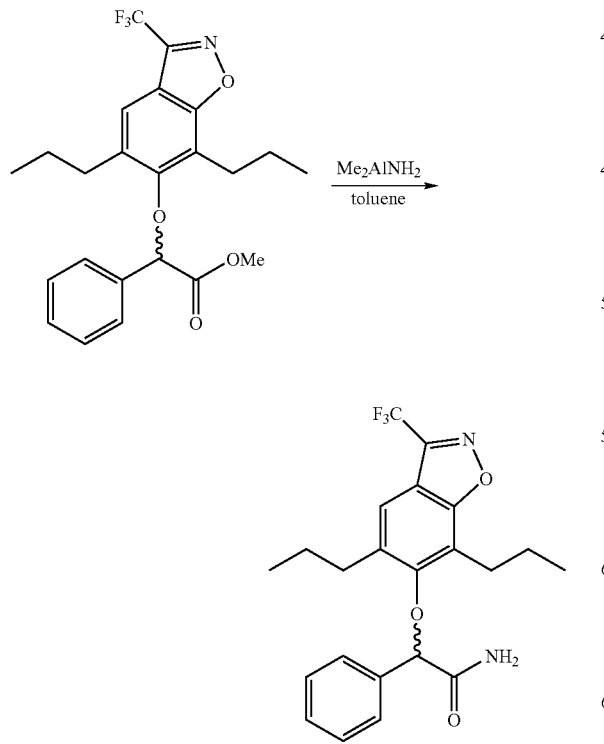

Dimethylaluminum amide was prepared by adding anhydrous toluene (10.6 ml) to ammonium chloride (0.5 g, 1 eq). The mixture was cooled to 0° C. and trimethylaluminum in toluene (2.0 M solution, 9.4 ml, 1 eq) was added dropwise. The reaction was allowed to stir at 0° C. for 15 min before warming to room temperature and stirring for an additional 1.5 h.

The indicated ester (0.5 g, 1 eq) was dissolved in toluene and freshly prepared 0.47 M dimethylaluminum amide (5 ml, 2 eq) was added. The reaction was then warmed to 100 C and allowed to stir for approximately 12 Hrs. The reaction was then cooled to room temperature and $Na_2SO_4.10\ H_2O$ was added and stirred for an additional hour. Filtration followed by concentration of the solvent gave a yellow liquid. This was chromatographed on silica gel using hexanes:ethyl acetate (90:10) to (1:1) to give the amide.

Characteristic NMR Resonances: $^1H$ NMR 400 MHz ($CDCl_3$): 7.23–7.36 (m, 6H), 7.03 (s, 1H), 6.37 (s, 1H), 5.11 (s, 1H), 2.47–2.54 (m, 2H), 2.33–2.39 (m, 2H), 1.55–1.62 (m, 2H), 1.39–1.46 (m, 2H), 0.81–0.86 (m, 6H)

Step 2 Preparation of α-[[5,7-dipropyl-3-(trifluoromethyl)-1,2-benzisoxazol-6-yl]oxy]benzeneacetonitrile.

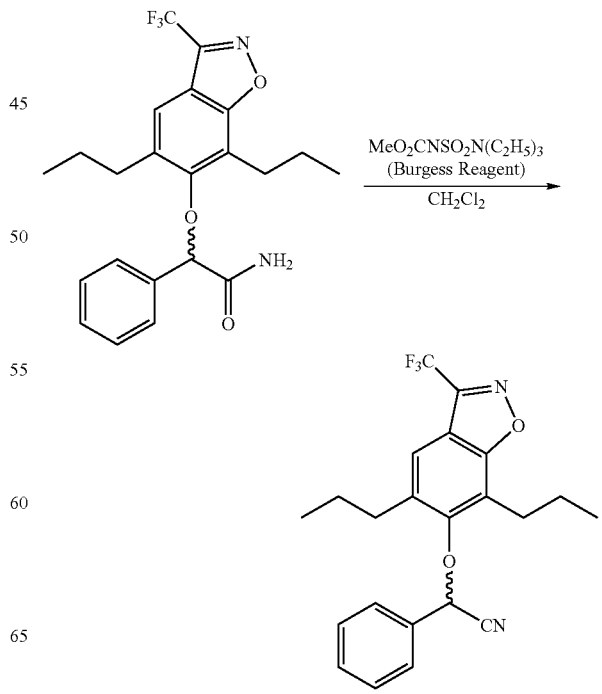

The indicated amide (0.24 g, 1 eq) was diluted with methylene chloride (5 ml) and (methoxycarbonylsulfamoyl)triethylammonium hydroxide, inner salt (0.312 g, 2.5 eq) was then added. The resulting mixture was stirred for 10 hours. The reaction mixture was then pipetted onto a silica gel column and eluted using hexane and ethyl acetate (20:1). The nitrile was obtained.

Characteristic NMR Resonances: $^1$H NMR 400 MHz (CDCl$_3$): 7.24–7.60 (m, 6H), 5.57 (s, 1H), 2.94–2.98 (m, 1H), 2.73–2.88 (m, 2H), 2.61–2.68 (m, 1H), 1.62–1.79 (m, 4H), 0.89–0.94 (m, 6H)

MS ESI M+1 403.2

Step 3 Preparation of 6-[phenyl(1H-tetrazol-5-yl)methoxy]-5,7-dipropyl-3-(trifluoromethyl)-1,2-benzisoxazole.

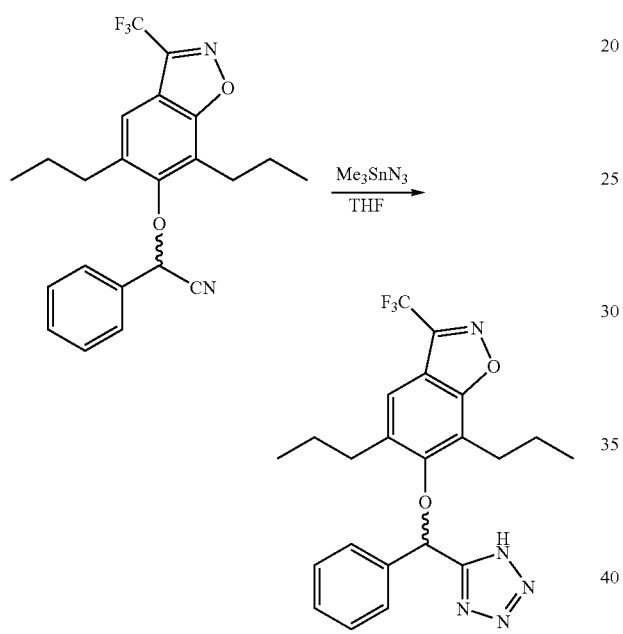

The indicated nitrile (0.13 g, 1 eq) was dissolve in anhydrous THF (5 ml). Trimethyltin azide (0.080 g, 1.2 eq) was then added. The reaction mixture was warmed to reflux and allowed to reflux for 12 hours. The solution was then cooled to room temperature. 0.5 N HCl was then added and the reaction was poured into a separatory funnel. The layers were separated and the aqueous layer was washed with ethyl acetate two more times. The combined organic fractions were dried with sodium sulfate and then concentrated. The crude mixture was chromatographed with hexanes:ethyl acetate under a gradient from 90:10 to 1:1 w/1% acetic acid to give a relatively pure tetrazole which was then purified further by HPLC on a YMC-pack C18 column CH$_3$CN:H$_2$O (30:90 to 100:0, 16 min gradient) containing 0.1% TFA as eluent.

Characteristic NMR Resonances: $^1$H NMR 400 MHz (CD3OD): 7.44–7.52 (m, 6H), 6.37 (s, 1H), 2.50–2.56 (m, 2H), 2.33–2.41 (m, 2H) 1.48–1.55 (m, 4H), 0.74–0.80 (m, 6H)

MS ESI M+1 446.2

Example 19

Step 1 Preparation of α-[[5,7-dipropyl-3-(trifluoromethyl)-1,2-benzisoxazol-6-yl]oxy]-4-chlorobenzeneacetamide.

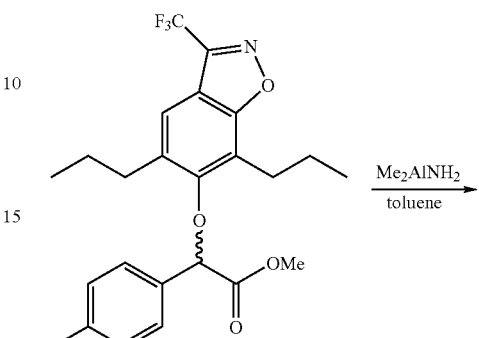

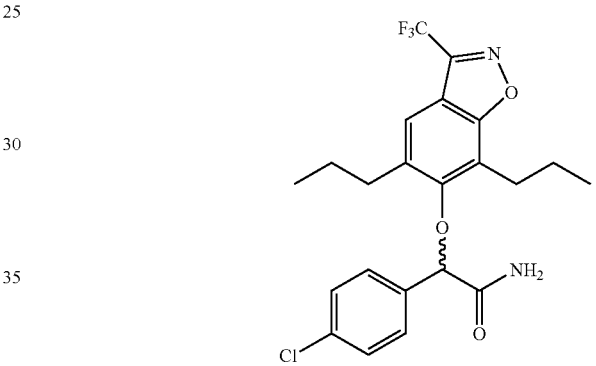

The title amide was prepared as was described for example 18, step 1 from the indicated ester (0.24 g, 1 eq) and Me$_2$AlNH$_2$ (0.89M, 1.15 ml, 2 eq).

Characteristic NMR Resonances: $^1$H NMR 400 MHz (CDCl$_3$): 7.18–7.37 (m, 5H), 7.04(s, 1H), 6.20 (s, 1H), 5.09 (s, 1H), 2.51–2.58 (m, 2H), 2.33–2.40 (m, 2H), 1.57–1.65 (m, 2H), 1.42–1.48 (m, 2H), 0.84–0.90 (m, 6H)

Step 2 Preparation of α-[[5,7-dipropyl-3-(trifluoromethyl)-1,2-benzisoxazol-6-yl]oxy]-4-chlorobenzeneacetonitrile.

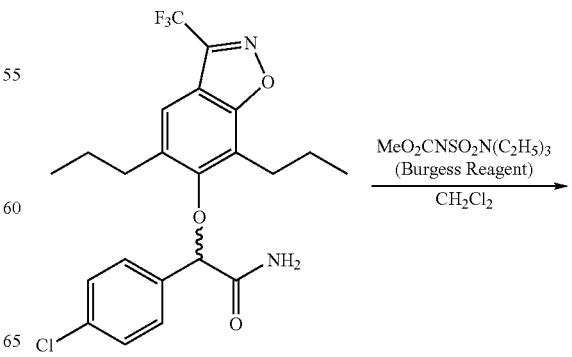

-continued

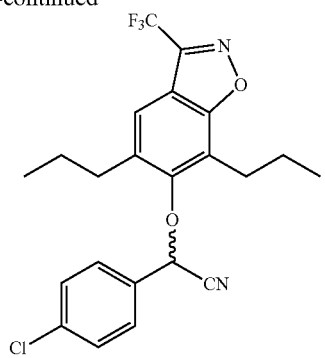

The title nitrile was prepared as was described for example 18, step 2 from the indicated amide (0.088 g, 1.0 eq) and (methoxycarbonylsulfamoyl)triethylammonium hydroxide, inner salt (0.115 g, 2.5 eq).

Characteristic NMR Resonances: $^1$H NMR 400 MHz (CDCl$_3$): 7.48–7.55 (m, 5H), 5.56 (s, 1H), 2.96–3.02 (m, 1H), 2.73–2.89 (m, 2H), 2.60–2.68 (m, 1H), 1.60–1.83 (m, 4H) 0.90–0.95 (m, 6H)

MS ESI M+1 437.1

Step 3. Preparation of 6-[(4-chlorophenyl)(1H-tetrazol-5-yl)methoxy]-5,7-dipropyl-3-(trifluoromethyl-1,2-benzisoxazole.

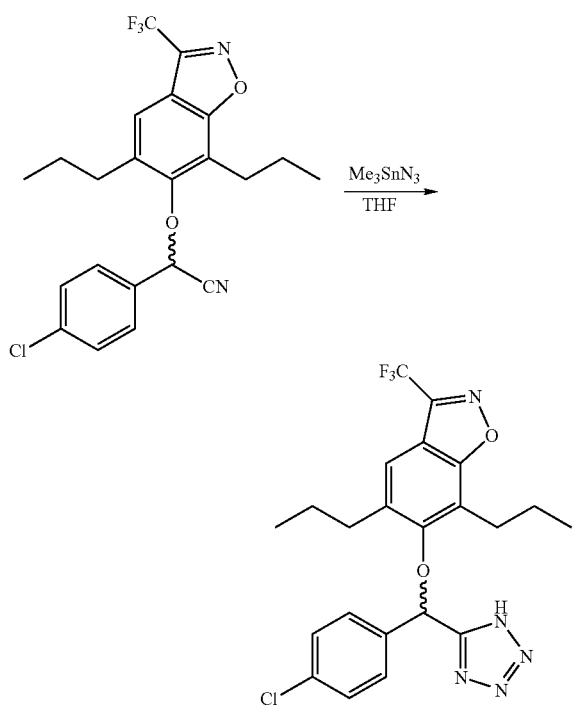

The title tetrazole was prepared as was described for example 18, step 3 from the indicated nitrile (0.1 g, 1.0 eq) and Me$_3$SnN$_3$ (0.057 g, 1.2 eq).

Characteristic NMR Resonances: 1H NMR 400 MHz (CD3OD): 7.46–7.54 (m, 5H), 6.40 (s, 1H), 2.50–2.62 (m, 2H), 2.31–2.42 (m, 2H), 1.46–1.60 (m, 4H), 0.75–0.82 (m, 6H)

MS ESI M+1 480.1

Example 20

Step 1 Preparation of α-[[5,7-dipropyl-3-(trifluoromethyl)-1,2-benzisoxazol-6-yl]oxy]4-(1-methylethyl)benzeneacetamide.

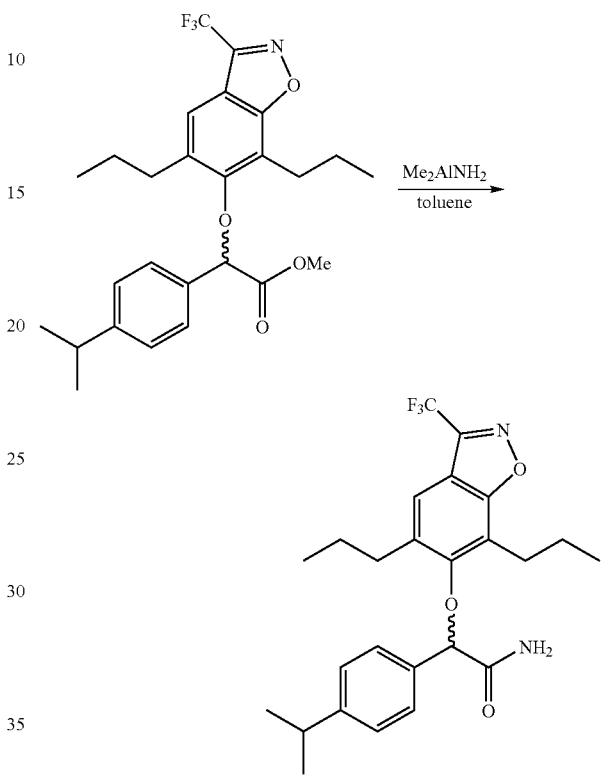

The title amide was prepared as was described for example 18, step 1 from the indicated ester (1.0, 1 eq) and Me$_2$AlNH$_2$ (0.38M, 10.3 ml, 2 eq).

Characteristic NMR Resonances: $^1$H NMR 400 MHz (CDCl$_3$): 7.36 (s, 1H), 7.13–7.18 (m, 4H), 7.05 (s, 1H), 5.60 (s, 1H), 5.08 (s, 1H), 2.83–2.87 (m, 1H), 2.33–2.52 (m, 4H), 1.24–1.62 (m, 4H), 1.17–1.23 (m, 6H), 0.77–0.84 (m, 6H)

Step 2 Preparation of α-[[5,7-dipropyl-3-(trifluoromethyl)-1,2-benzisoxazol-6-yl]oxy]4-(1-methylethyl)benzeneacetonitrile.

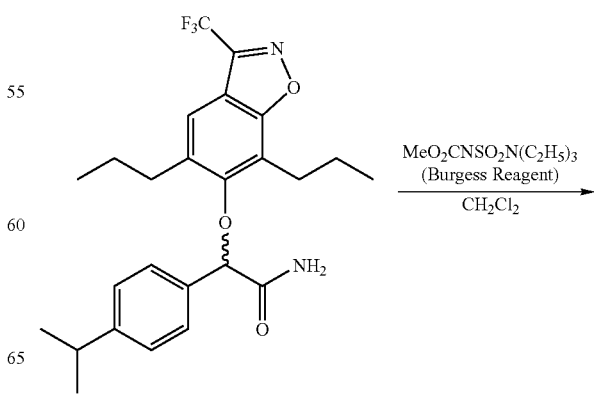

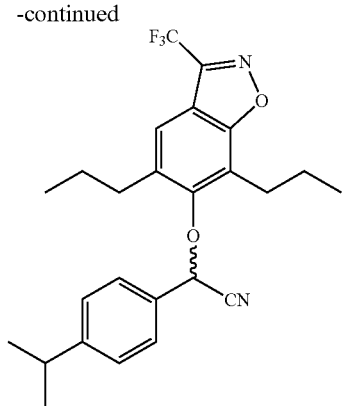

The title nitrile was prepared as for example 18, step 2 from the indicated amide (0.58 g, 1.0 eq) and (methoxycarbonylsulfamoyl)triethylammonium hydroxide, inner salt (0.747 g, 2.5 eq).

Characteristic NMR Resonances: $^1$H NMR 400 MHz (CDCl$_3$): 7.49 (d, J=10.1 Hz, 2H), 7.47 (s, 1H), 7.35(d, J=8.1 Hz, 2H), 5.53 (s, 1H), 2.93–3.02 (m, 2H), 2.7–2.88 (m, 2H), 2.62–2.68 (m, 1H), 1.61–1.84 (m, 4H), 1.27 (d, J=7.0 Hz, 6H), 0.91–0.95(m, 6H)

MS ESI M+1 445.2

Step 3 Preparation of 6-[[4-(1-methylethyl)phenyl](1H-tetrazol-5-yl)methoxy]-5,7-dipropyl-3-(trifluoromethyl)-1,2-benzisoxazole.

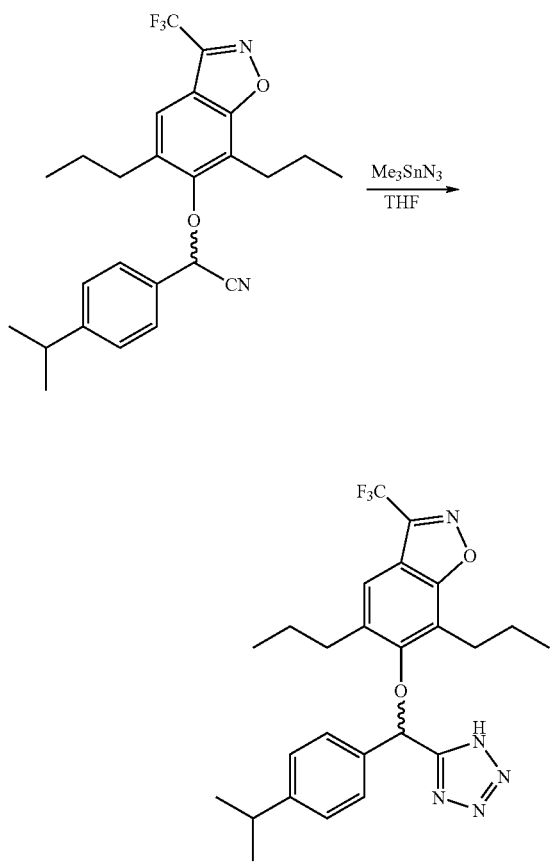

The title tetrazole was prepared as was described for example 18, step 3 from the indicated nitrile (0.56 g, 1.0 eq) and Me$_3$SnN$_3$ (0.311 g, 1.2 eq).

Characteristic NMR Resonances: 1H NMR 400 MHz (CD3OD): 7.49 (s, 1H), 7.35 (dd, J=8.4, 24.4 Hz, 4H), 6.32 (s, 1H), 2.90–2.98 (m, 1H), 2.50–2.55 (m, 2H), 2.30–2.44 (m, 2H), 1.36–1.60 (m, 4H), 1.25 (d, J=7.2 Hz, 6H), 0.76 (dd, J=7.2, 16.0 Hz, 6H)

MS ESI M+Na 510.2

Example 21

Step 1 Preparation of α-[[5,7-dipropyl-3-(trifluoromethyl)-1,2-benzisoxazol-6-yl]oxy]-4-(trifluoromethyl)benzeneacetamide.

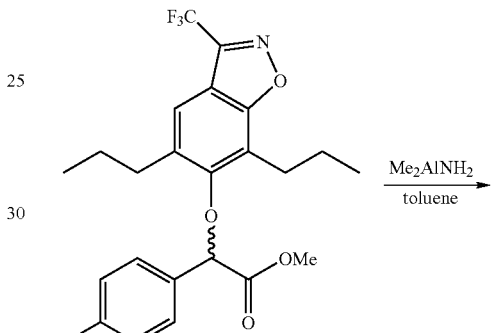

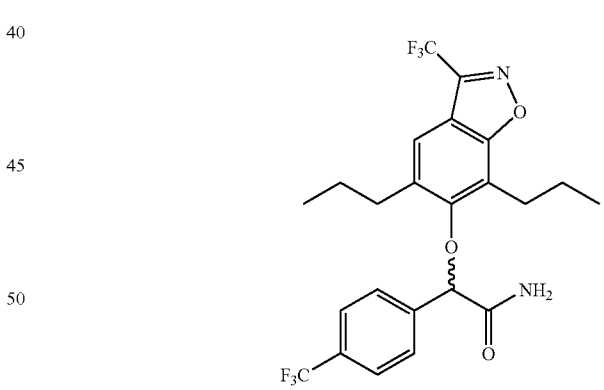

The title amide was prepared as was described for example 18, step 1 from the indicated ester (0.70 g, 1 eq) and Me$_2$AlNH$_2$ (0.93M, 3.0 ml, 2 eq).

Characteristic NMR Resonances: $^1$H NMR 400 MHz (CDCl$_3$): 7.61(d, J=8.4 Hz, 2H), 7.42 (d, J=8.0 Hz, 2H), 7.38 (s, 1H), 7.06 (s, 1H), 6.06 (s, 1H), 5.16 (s, 1H), 2.48–2.62 (m, 2H), 2.30–2.44 (m, 2H), 1.52–1.68 (m, 2H), 1.34–1.48 (m, 2H), 0.81–0.88 (m, 6H)

Step 2 Preparation of α-[[5,7-dipropyl-3-(trifluoromethyl)-1,2-benzisoxazol-6-yl]oxy]-4-(trifluoromethyl)benzeneacetonitrile.

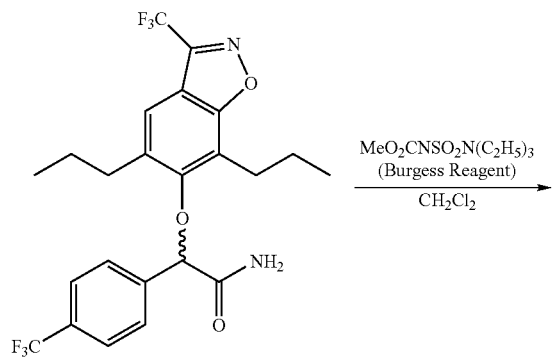

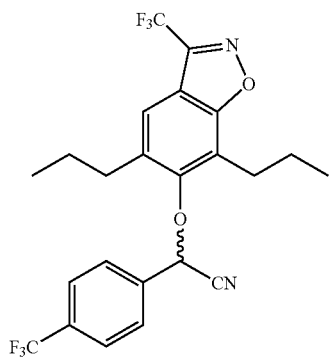

The title nitrile was prepared as for example 18, step 2 from the indicated amide (0.2383 g, 1.0 eq) and (methoxycarbonylsulfamoyl)triethylammonium hydroxide, inner salt (0.3 g, 2.5 eq).

Characteristic NMR Resonances: $^1$H NMR 400 MHz (CDCl$_3$): 7.78 (dd, J=8.5, 21.3 Hz, 4H), 7.50 (s, 1H), 5.67 (s, 1H), 2.97–3.03 (m, 1H), 2.84–2.90 (m, 1H), 2.75–2.81 (m, 1H), 2.62–2.68 (m, 1H), 1.62–1.84 (m, 4H), 0.92 (dd, J=7.5, 15.3 Hz, 6H)

MS ESI M+1 471.3

Step 3 Preparation of 6-[(1H-tetrazol-5-yl)[4-(trifluoromethyl)phenyl]methoxy]-5,7-dipropyl-3-(trifluoromethyl)-1,2-benzisoxazole.

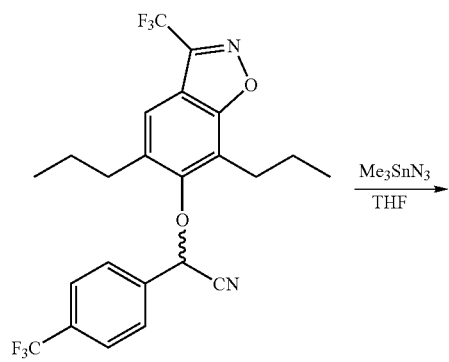

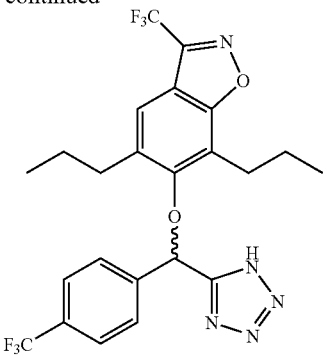

The title tetrazole was prepared as was described for example 18, step 3 from the indicated nitrile (0.2 g, 1.0 eq) and Me$_3$SnN$_3$ (0.105 g, 1.2 eq).

Characteristic NMR Resonances: $^1$H NMR 400 MHz (CD$_3$OD): 7.79 (s, 4H), 7.52 (s, 1H), 6.52 (s, 1H), 2.52–2.58 (m, 2H), 2.35–2.39 (m, 2H), 1.46–1.56 (m, 4H), 0.74–0.80 (m, 6H)

MS ESI M+1 514.2

Example 22

Step 1 Preparation of α-[[5,7-dipropyl-3-(trifluoromethyl)-1,2-benzisoxazol-6-yl]oxy]4-(2-methylpropyl)benzeneacetamide.

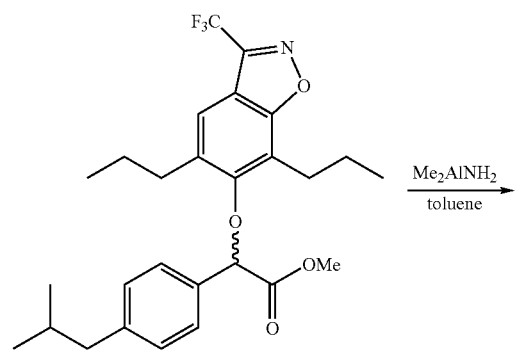

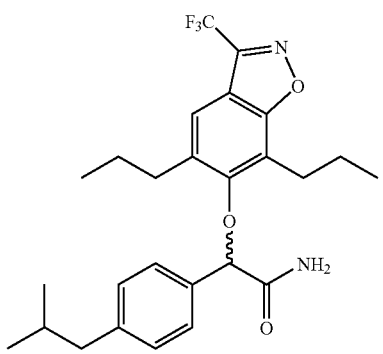

The title amide was prepared as was described for example 18, step 1 from the indicated ester (0.73 g, 1 eq) and Me$_2$AlNH$_2$ (0.39M, 7.6 ml, 2 eq).

Characteristic NMR Resonances: ¹H NMR 400 MHz (CDCl₃): 7.35 (d, J=3.9 Hz, 1H), 7.08–7.14 (m, 4H), 7.05 (s, 1H), 6.14 (s, 1H), 5.09 (s, 1H), 2.33–2.53 (m, 6H), 1.78–1.85 (m, 1H), 1.55–1.62 (m, 2H), 1.38–1.50 (m, 2H), 0.82–0.88 (m, 12H)

Step 2 Preparation of α-[[5,7-dipropyl-3-(trifluoromethyl)-1,2-benzisoxazol-6-yl]oxy]-4-(2-methylpropyl)benzeneacetonitrile.

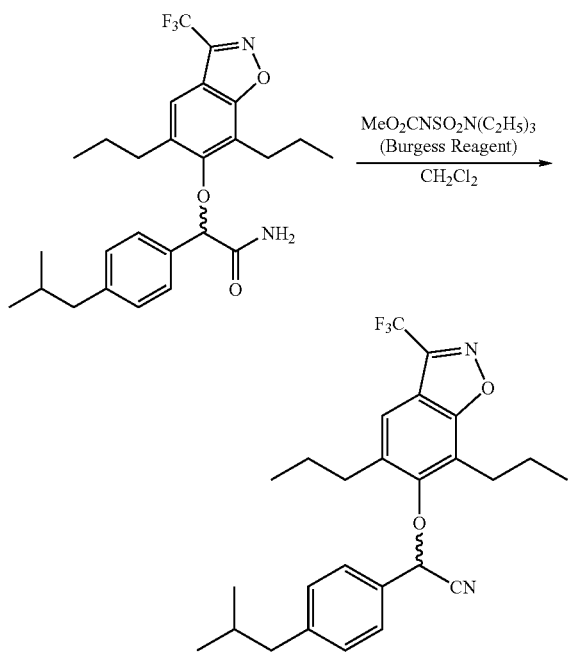

The title nitrile was prepared as was described for example 18, step 2 from the indicated amide (0.33 g, 1.0 eq) and (methoxycarbonylsulfamoyl)triethylammonium hydroxide, inner salt (0.412 g, 2.5 eq).

Characteristic NMR Resonances: ¹H NMR 400 MHz (CDCl₃): 7.47–7.49 (m, 3H), 7.27 (d, J=8.2 Hz, 2H), 5.53 (s, 1H), 2.93–2.99(m, 1H), 2.73–2.87 (m, 2H), 2.61–2.69 (m, 1H), 2.54 (d, J=7.0 Hz, 2H), 1.86–1.94 (m, 1H), 1.55–1.79 (m, 4H), 0.85–0.96 (m, 12H)

MS ESI M+1

Step 3 Preparation of 6-[[4-(2-methylpropyl)phenyl](1H-tetrazol-5-yl)methoxy]-5,7-dipropyl-3-(trifluoromethyl)-1,2-benzisoxazole

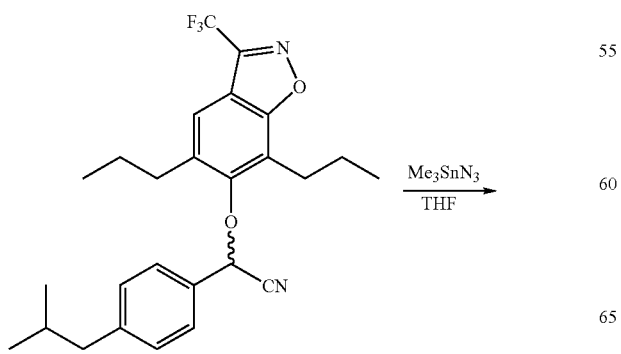

-continued

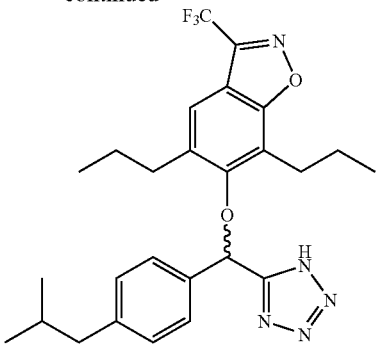

The title tetrazole was prepared as for example 18, step 3 from the indicated nitrile (0.3 g, 1.0 eq) and Me₃SnN₃ (0.162 g, 1.2 eq).

Characteristic NMR Resonances: ¹H NMR 400 MHz (CD₃OD): 7.49 (s, 1H), 7.29 (dd, J=8.4, 48.4 Hz, 4H), 6.32 (s, 1H), 2.49–2.54 (m, 4H), 2.33–2.40 (m, 2H), 1.84–1.91 (m, 1H), 1.47–1.54 (m, 4H), 0.090 (dd, J=1.2, 6.7 Hz, 6H), 0.74–0.80 (m, 6H)

MS ESI M+1

Example 23

Step 1 Preparation of α-[[5,7-dipropyl-3-(trifluoromethyl)-1,2-benzisoxazol-6-yl]oxy]-4-ethylbenzeneacetamide.

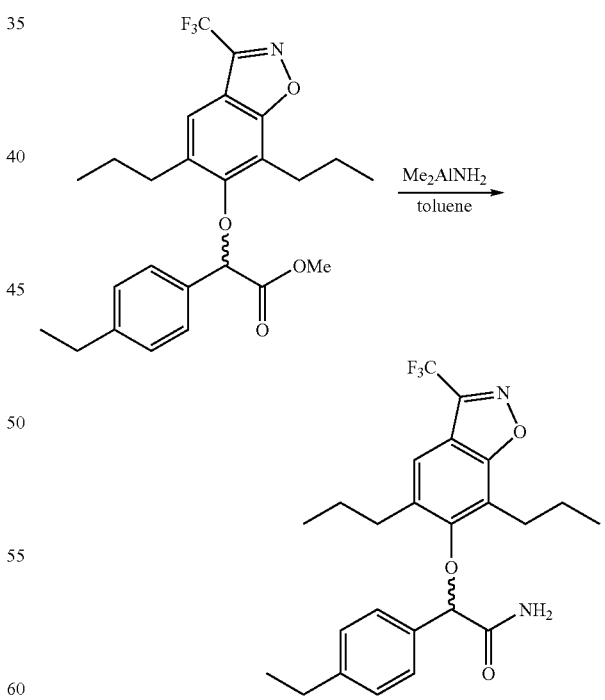

The title amide was prepared as was described for example 18, step 1 from the indicated ester (0.15 g, 1 eq) and Me₂AlNH₂ (0.39M, 1.7 ml, 2 eq).

Characteristic NMR Resonances: ¹H NMR 400 MHz (CDCl₃): 7.36 (s, 1H), 7.14 (s, 4H), 7.05 (s, 1H), 5.92 (s, 1H), 5.09 (s, 1H), 2.61 (dd, J=7.7, 15.3 Hz, 2H), 2.47–2.55 (m, 2H), 2.34–2.41 (m, 2H), 1.31–1.68 (m, 4H), 1.22–1.28 (m, 3H), 0.81–0.88 (m, 6H)

Step 2 Preparation of α-[[5,7-dipropyl-3-(trifluoromethyl)-1,2-benzisoxazol-6-yl]oxy]-4-ethylbenzeneacetonitrile.

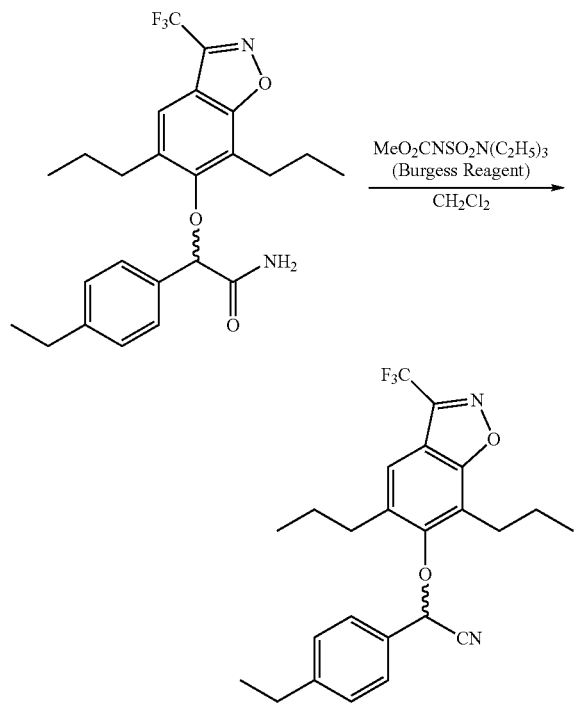

The title nitrile was prepared as was described for example 18, step 2 from the indicated amide (0.08 g, 1.0 eq) and (methoxycarbonylsulfamoyl)triethylammonium hydroxide, inner salt (0.106 g, 2.5 eq).

Characteristic NMR Resonances: $^1$H NMR 400 MHz (CDCl$_3$): 7.49 (d, J=8.0 Hz, 2H), 7.47 (s, 1H), 7.32 (d, J=8.0 Hz, 2H), 5.54 (s, 1H), 2.93–3.2 (m, 1H), 2.62–2.90 (m, 5H), 1.61–1.82 (m, 4H), 1.26 (t, J=7.6 Hz, 3H), 0.90–0.95 (m, 6H)

Step 3 Preparation of 6-[[(4-ethylphenyl)(1H-tetrazol-5-yl)methoxy]-5,7-dipropyl-3-(trifluoromethyl)-1,2-benzisoxazole.

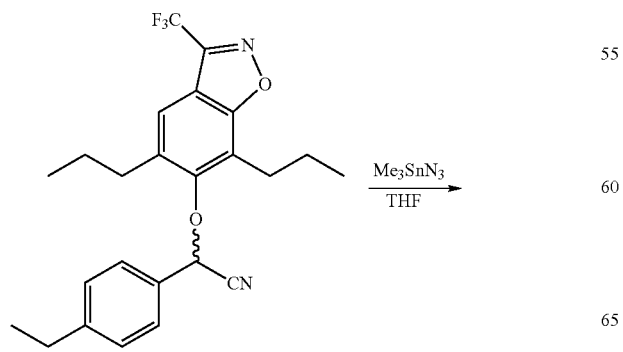

-continued

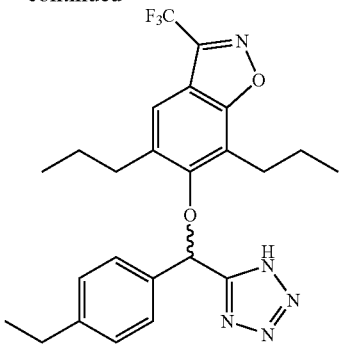

The title tetrazole was prepared as was described for example 18, step 3 from the indicated nitrile (0.075 g, 1.0 eq) and Me$_3$SnN$_3$ (0.054 g, 1.2 eq).

Characteristic NMR Resonances: $^1$H NMR 400 MHz (CD$_3$OD): 7.49 (s, 1H), 7.37 (d, J=8.2 Hz, 2H), 7.28 (d, J=8.4 Hz, 2H), 6.32 (s, 1H), 2.65 (dd, J=7.6, 15.2 Hz, 2H), 2.50–2.55 (m, 2H), 2.33–2.40 (m, 2H), 1.41–1.59 (m, 4H), 1.23 (t, J=7.6 Hz, 3H), 0.73–0.79 (m, 6H)

MS ESI M+Na 524.2

Example 24

Step 1 Preparation of α-[[5,7-dipropyl-3-phenyl-1,2-benzisoxazol-6-yl]oxy]benzeneacetamide.

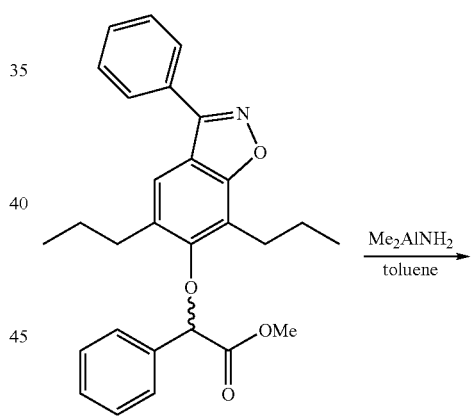

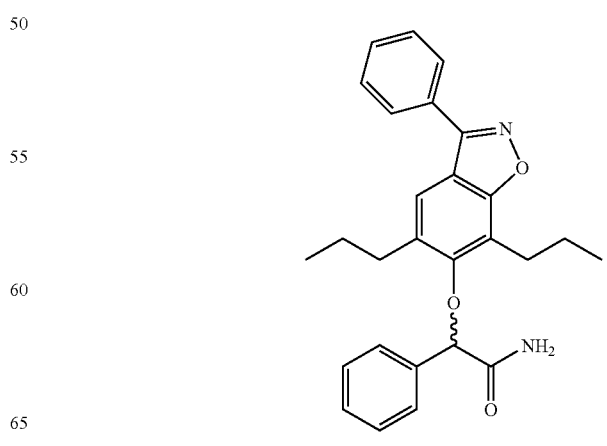

The title amide was prepared as was described for example 18, step 1 from the indicated ester (0.12 g, 1 eq) and Me$_2$AlNH$_2$ (0.57M, 0.95 ml, 2 eq).

Characteristic NMR Resonances: $^1$H NMR 400 MHz (CDCl$_3$): 7.89–7.90 (m, 2H), 7.51–7.55 (m, 3H), 7.13–7.47 (m, 6H), 7.13 (s, 1H), 6.06(s, 1H), 5.15 (s, 1H), 2.50–2.58 (m, 2H), 2.34–2.40 (m, 2H), 1.62–1.74 (m, 2H), 1.44–1.48 (m, 2H), 1.23–1.26 (m, 3H), 0.84–0.89 (m, 3H)

Step 2 Preparation of α-[[5,7-dipropyl-3-phenyl-1,2-benzisoxazol-6-yl]oxy]benzeneacetonitrile.

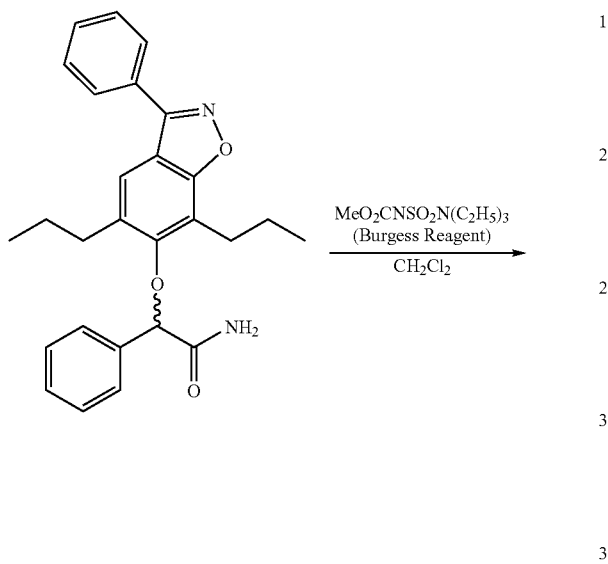

The title nitrile was prepared as was described for example 18, step 2 from the indicated amide (0.06 g, 1.0 eq) and (methoxycarbonylsulfamoyl)triethylammonium hydroxide, inner salt (0.083 g, 2.5 eq).

Characteristic NMR Resonances: $^1$H NMR 400 MHz (CDCl$_3$): 7.94–7.97 (m, 2H), 7.54–7.66 (m, 9H), 5.63 (s, 1H), 2.66–3.06 (m, 4H), 1.68–1.91 (m, 4H), 1.01–1.32 (m, 3H), 0.87–0.99 (m, 3H).

MS ESI M+1 411.3

Step 3 Preparation of 6-[(phenyl)(1H-tetrazol-5-yl)methoxy]-5,7-dipropyl-3-phenyl-1,2-benzisoxazole.

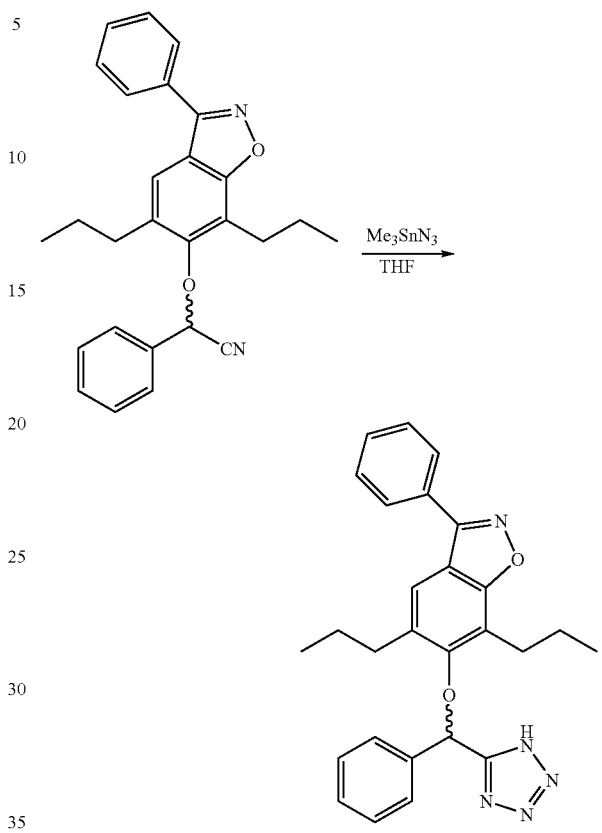

The title tetrazole was prepared as was described for example 18, step 3 from the indicated nitrile (0.057 g, 1.0 eq) and Me$_3$SnN$_3$ (0.034 g, 1.2 eq).

Characteristic NMR Resonances: $^1$H NMR 400 MHz (CD$_3$OD): 7.91–9.3 (m, 2H), 7.52–7.61 (m, 6H), 7.41–7.45 (m, 2H), 6.30 (s, 1H), 2.50–2.55 (m, 2H), 2.34–2.40 (m, 2H), 1.48–1.55 (m, 4H), 0.73–0.81 (m, 6H)

MS ESI M+1 454.1

Example 25

Step 1 Preparation of α-[4-(1-oxopropyl)-2,6-dipropylphenoxy]-4-(1-methylethyl)benzeneacetamide.

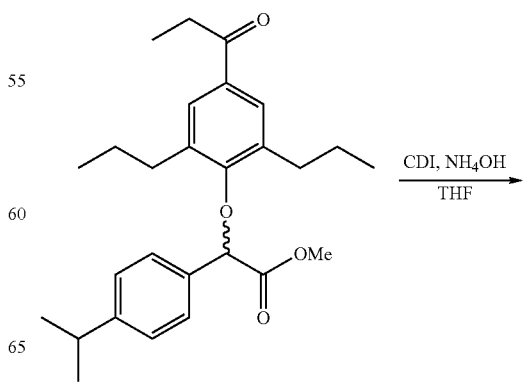

-continued

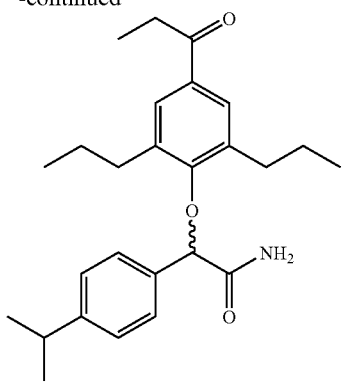

The indicated acid (0.10 g, 1.0 eq) was dissolved in THF. CDI (0.47 g, 1.2 eq) was added and allowed to warm to 60° C. for 1 h. The reaction was cooled to room temperature and NH₄OH (14.8N, 0.5 ml) was added. The reaction was then stirred for another 0.5 h. The reaction was poured into water and extracted with ethyl acetate. The organic phase was dried with sodium sulfate and concentrated to give a yellow oil. The oil was then chromatographed on silica gel with hexanes:ethyl acetate (1:1) to give the amide.

Characteristic NMR Resonances: ¹H NMR 400 MHz (CDCl₃): 7.58 (s, 2H), 7.15 (s, 4H), 7.09 (d, J=2.6 Hz, 1H), 6.55 (s, 1H), 5.27 (s, 1H), 2.83–2.94 (m, 3H),2.21–2.30 (m, 4H), 1.46–1.55 (m, 2H), 1.15–1.35 (m, 11H), 0.86 (t, J=6.6 Hz, 6H)

Step 2 Preparation of α-[4-(1-oxopropyl)-2,6-dipropylphenoxy]-4-(1-methylethyl)benzeneacetonitrile.

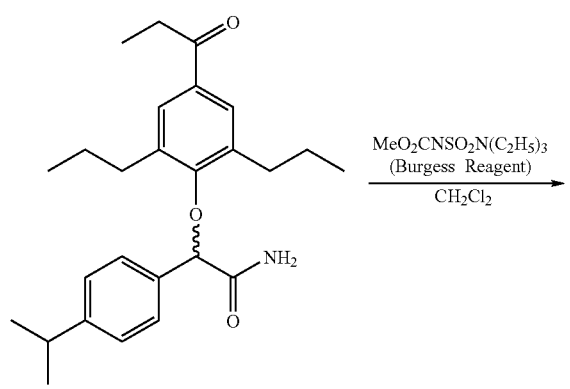

The title nitrile was prepared as was described for example 18, step 2 from the indicated amide (0.98 g, 1.0 eq) and (methoxycarbonylsulfamoyl)triethylammonium hydroxide, inner salt (0.143 g, 2.5 eq).

Characteristic NMR Resonances: ¹H NMR 400 MHz (CDCl₃): 7.68 (s, 2H), 7.40 (dd, J=8.2, 62.9 Hz, 4H), 5.48 (s, 1H), 2.96 (dd, J=7.2, 14.4 Hz, 3H), 2.63 (m, 4H), 1.61 (m, 4H), 1.26 (d, J=6.8 Hz, 6H), 1.20 (t, J=7.2 Hz, 3H), 0.90 (t, J=7.3 Hz, 6H)

MS ESI M+1 392.2

Step 3 Preparation of 1-[4-[[4-(1-methylethyl)phenyl](1H-tetrazol-5-yl)methoxy]-2,6-dipropylphenyl]-1-propanone.

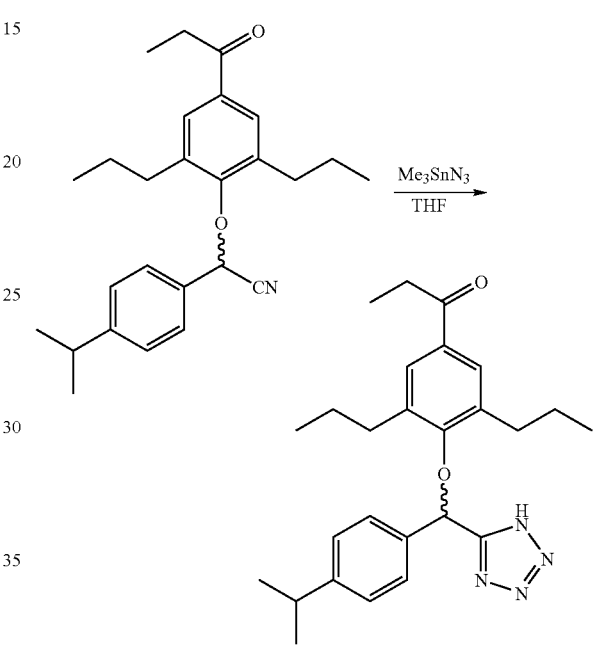

The title tetrazole was prepared as was described for example 18, step 3, from the indicated nitrile (0.12 g, 1.0 eq) and Me₃SnN₃ (0.094 g, 1.5 eq).

Characteristic NMR Resonances: ¹H NMR 400 MHz (CD₃OD): 7.67 (s, 2H), 7.32 (dd, 4H, J=8.2, 19.9 Hz), 6.20(s, 1H), 2.99 (dd, 2H, J=7.2, 14.4 Hz), 2.92 (dd, 1H, J=6.8, 13.9 Hz), 2.14–2.28 (m, 4H), 1.31–1.47 (m, 4H), 1.24 (dd, J=0.8, 6.8 Hz, 6H), 1.15 (t, 3H, J=7.0 Hz), 0.75 (m, 6H).

MS ESI M+Na 457.2

Example 26

Step 1 Preparation of α-[[5,7-dipropyl-3-(trifluoromethyl)-1,2-benzisoxazol-6-yl]oxy]]-N-[(2,2,2-trifluoroethyl)sulfonyl]benzeneacetamide

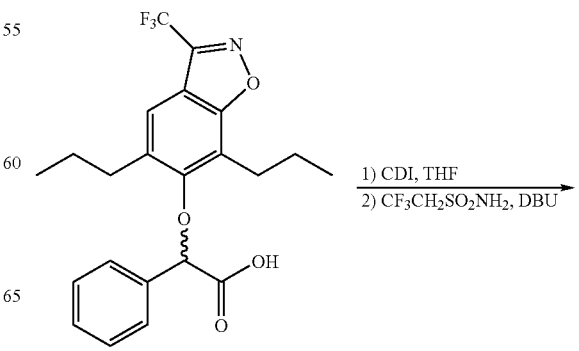

-continued

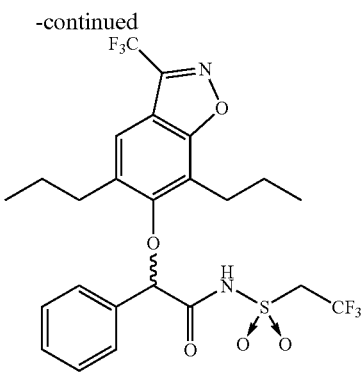

The CF₃CH₂SO₂NH₂ was prepared by cooling a solution of commercially available CF₃CH₂SO₂Cl (0.6 ml, 1 eq) in CH₂Cl₂ to 0° C. NH₄OH (0.75 ml, 14.8 N, 2 eq) was then added dropwise. The mixture was allowed to warm to room temperature overnight. The reaction was diluted with water and extracted three times with CH₂Cl₂. The combined organic layers were dried with Na₂SO₄ and concentrated. The sulfonamide was used without further purification.

The indicated acid (0.10 g, 1.0 eq) was dissolved in THF. 1,1'-Carbonyldiimidazole (0.46 g, 1.2 eq) was added and allow to warm to 60° C. for 0.5 h. The reaction was cooled to room temperature and then CF₃CH₂SO₂NH₂ (0.42 g, 1.2 eq) and 1,8-Diazabicyclo [5.4.0] undec-7-ene (0.40 g, 1.1 eq) were added. The mixture was stirred for another hour. The reaction was poured into saturated NH₄Cl solution and extracted three times with ethyl acetate. The organic phase was dried with sodium sulfate and concentrated. The crude mixture was purified by HPLC on a YMC-pack C18 column CH₃CN:H₂O (30:90 to 100:0, 16 min gradient) containing 0.1% TFA as eluent.

Characteristic NMR Resonances: $^1$H NMR 400 MHz (CD3OD): 7.43–7.51 (m, 6H), 5.29 (s, 1H), 4.52 (dd, 2H, J=9.1, 18.3 Hz), 2.63–2.71 (m, 2H), 2.51–2.56 (m, 2H), 1.45–1.67 (m, 4H), 0.82–0.87 (m, 6H).

MS ESI M+1 567.25

Example 27

Step 1 Preparation of α-[[5,7-dipropyl-3-(trifluoromethyl)-1,2-benzisoxazol-6-yl]oxy]]-N-[propylsulfonyl]benzeneacetamide

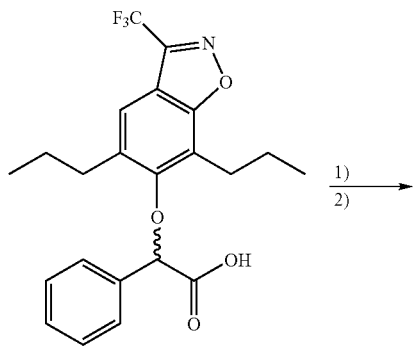

-continued

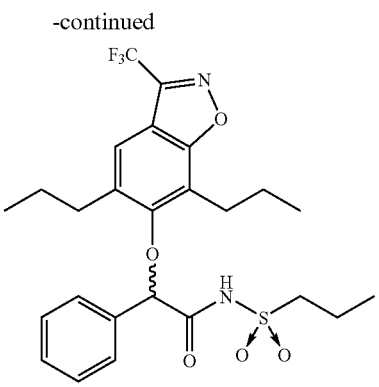

PrSO₂NH₂ was prepared as was described for example 26 from commercially available PrSO₂Cl.

The title sulfonamide was prepared from the indicated acid (0.04 g, 1.0 eq), CDI (0.019 g, 1.2 eq), and DBU (0.017 g, 1.1 eq).

Characteristic NMR Resonances: 1H NMR 400 MHz (CD3OD): 7.44–7.56 (m, 6H), 5.26 (s, 1H), 3.32–3.35 (m, 2H), 2.67–2.74 (m, 2H), 2.53–2.58 (m, 2H), 1.47–1.67 (m, 6H), 0.83–0.92 (m, 9H)

MS ESI M+1 527.20

Example 28

Step 1 Preparation of Ethyl 2-Bromo-2-(3-thiophene)acetate.

Ethyl 3-thiopheneacetate (1.0 g, 1.0 eq) was dissolved in THF (50 mL) and cooled to −78° C. Lithium bis (trimethylsilyl) amide (6.46 mL, 1.1 eq) was added to the reaction and stirred for 20 minutes. Chlorotrimethylsilane (1.4 mL, 1.875 eq) was added at −78° C. and stirred for 20 minutes. N-bromosuccinimide (1.06 g, 1.01 eq) was added to the reaction mixture. The reaction mixture was allowed to stir and warm to room temperature overnight. The reaction mixture was diluted with H₂O. The organic layer was extracted with ethyl acetate. The organic phase was dried over sodium sulfate and the solvent was evaporated to give yellow oil. The resulting oil was chromatographed on silica gel using hexanes and ethyl acetate (95:5) to give the titled compound.

Characteristic NMR Resonances; $^1$H NMR 500 MHz (CDCl₃); 7.50 (dd, 1H), 7.39 (dd, 1H), 7.32 (d, 1H) 5.75 (s, 1H), 4.28 (q, 2H), 1.36 (t, 3H)

Step 2 Preparation of Ethyl α-[[5,7-dipropyl-3-(trifluoromethyl)-1,2-benzisoxazol-6-yl]oxy]-3-thiopheneacetate.

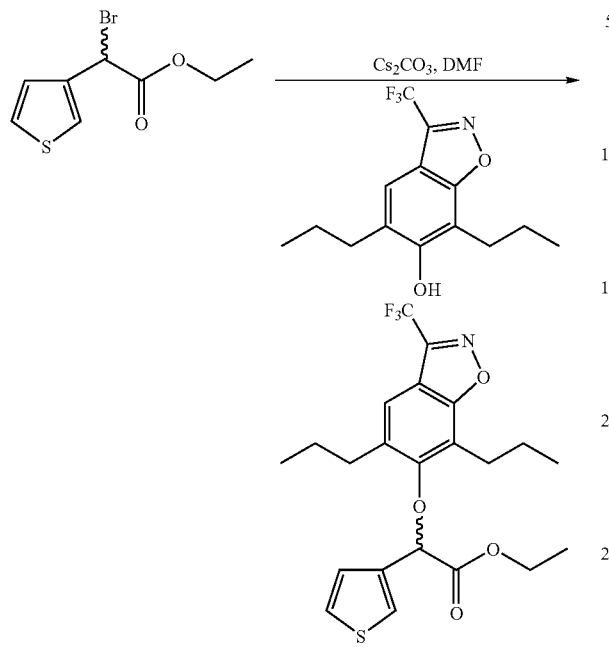

The title ester was prepared as was described for example 1, step 4 from the indicated bromide (53 mg, 0.2 mmol) and the indicated phenol (65 mg, 0.29 mmol). The product was purified by silica gel chromatography (hexanes:methyl t-butyl ether 99:1) to yield the desired ester.

Characteristic NMR Resonances; $^1$H NMR 500 MHz (CDCl$_3$); 7.40 (s, 1H), 7.38 (dd, 1H), 7.36 (dd, 1H), 7.26 (dd, 1H), 5.36 (s 1H), 4.28 (q, 2H), 2.72 (m, 4H), 2.56 (m, 4H), 1.66 (m, 4H), 1.28 (t, 3H), 0.92 (m, 6H).

Step 3 Preparation of α-[[5,7-dipropyl-3-(trifluoromethyl)-1,2-benzisoxazol-6-yl]oxy]-3-thiopheneacetic acid.

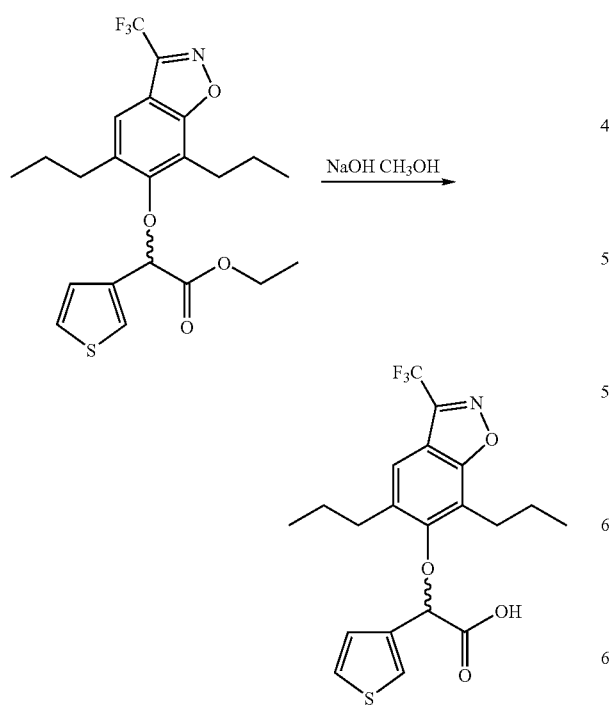

The title acid was prepared as was described for example 1, step 5, from the indicated ester (67 mg, 1.0 eq) and NaOH (0.38 mL, 5 M, 2.0 eq).

Characteristic NMR Resonances; $^1$H NMR 400 MHz (CDCl$_3$); 7.41 (m, 2H), 7.39 (dd, 1H), 7.27 (dd, 1H). 5.48 (s, 1H), 2.54 (q, 2H), 2.51 (m, 2H), 0.90 (m, 6H), Example 29

Step 1 Preparation of Ethyl 2-Bromo-2-(3-pyridyl)acetate.

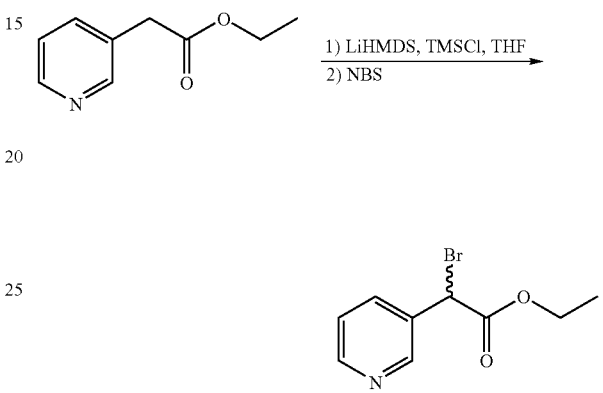

Ethyl 3-pyridylacetate (1.0 g, 1.0 eq) was dissolved in THF (50 mL) and cooled to −78° C. Lithium bis (trimethylsilyl) amide (6.66 mL, 1.1 eq) was added to the reaction and stirred for 20 minutes. Chlorotrimethylsilane (1.44 mL, 1.875 eq) was added at −78° C. and stirred for 20 minutes. N-bromosuccinimide (1.09 g, 1.01 eq) was added to the reaction mixture. The reaction mixture was allowed to stir and warm to room temperature overnight. The reaction mixture was diluted with H$_2$O. The organic layer was extracted with ethyl acetate. The organic phase was dried over sodium sulfate and the solvent was evaporated to give a yellow oil. The resulting oil was chromatographed on silica gel using hexanes and ethyl acetate (1:1) to give ethyl 2-bromo-2(3-pyridyl)acetate.

Characteristic NMR Resonances; $^1$H NMR 500 MHz (CDCl$_3$); 8.70 (d, 1H), 8.63 (dd, 1H), 7.92(dt, 1), 7.36 (dd, 1H) 5.37 (s, 1H), 4.26 (q, 2H), 1.28 (t, 3H)

Step 2 Preparation of Ethyl α-[[5,7-dipropyl-3-(trifluoromethyl)-1,2-benzisoxazol-6-yl]oxy]-3-pyridineacetate.

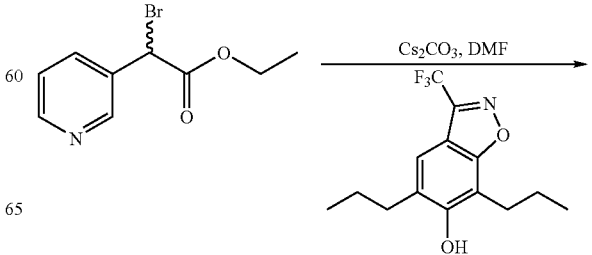

-continued

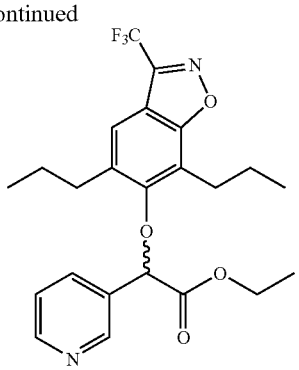

The title ester was prepared as was described for example 1, step 4 from the indicated bromide (83 mg) and the indicated phenol (98 mg). The product was purified by silica gel chromatography (hexanes:ethyl acetate 4:1) to yield the desired ester.

Characteristic NMR Resonances; $^1$H NMR 500 MHz (CDCl$_3$); 8.72 (d, 1H), 8.69 (dd, 1H), 7.97 (dt, 1H), 7.41 (m, 2H), 5.36 (s 1H), 4.25 (q, 2H), 2.79 (m, 2H), 2.59 (m, 2H), 1.65 (m, 4H), 1.25 (t, 3H), 0.89 (m, 6H).

Step 3 Preparation of α-[[5,7-dipropyl-3-(trifluoromethyl)-1,2-benzisoxazol-6-yl]oxy]-3-pyridineacetic acid.

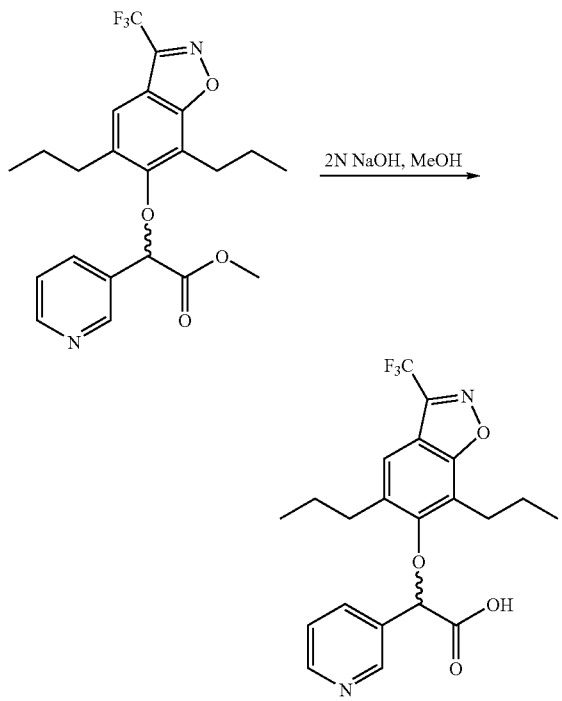

The title acid was prepared as was described for example 1, step 5, from the indicated ester (58 mg, 1.0 eq) and NaOH (0.33 mL, 2 M, 2.5 eq).

Characteristic NMR Resonances; $^1$H NMR 500 MHz (CDCl$_3$); 9.00(s, 1H), 8.76 (s, 1H), 8.40 (dd, 1H), 7.41 (s, 1H). 5.48 (s, 1H), 2.83 (m, 2H), 2.601 (m, 2H), 1.65 (m, 4H), 0.88 (m, 6H).

Example 30

Step 1 Preparation of methyl [4-(pyridin-2-ylmethoxy)phenyl]acetate.

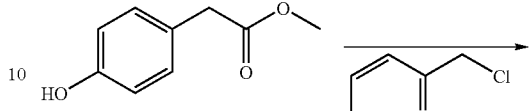

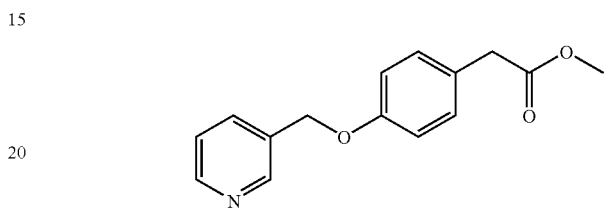

Commercially available methyl-4-hydrophenylacetate (5.00 g) was dissolved in dimethylformamide (50 mL). 2-Picolyl chloride hydrochloride (4.94 g) and cesium carbonate (24.50 g) was added. The reaction was stirred at room temperature for 18 hr. The reaction mixture was diluted with H$_2$O. The organic layer was extracted with ethyl acetate. The organic phase was dried over sodium sulfate and the solvent was evaporated to give a yellow oil. The resulting oil was chromatographed on silica gel using hexanes:ethyl acetate (60:40) to the title compound.

Characteristic NMR Resonances; $^1$H NMR 500 MHz (CDCl$_3$); 8.58 (d, 1H), 7.70 (dt 1H), 7.51 (d, 1H), 7.20 (m, 3H), 6.92 (d, 2H), 5.19 (s, 2H), 3.68 (s, 3H), 3.58 (s, 2H).

Step 2 Preparation of methyl α-bromo[4-(pyridin-2-ylmethoxy)phenyl]acetate.

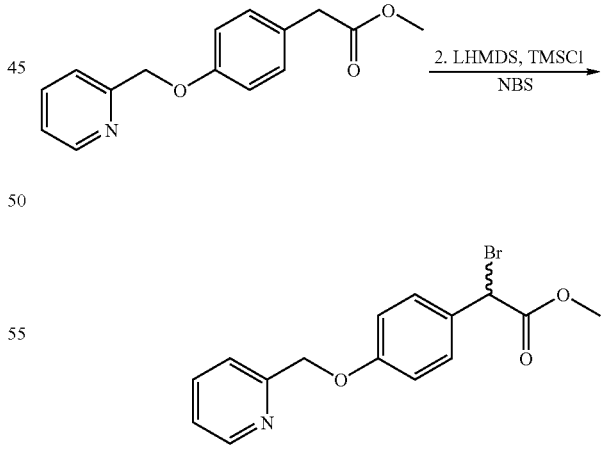

The crude oil prepared above was cooled to −78° C. in THF (100 mL). Lithium bis (trimethylsilyl) amide (27.91 mL, 1.1 eq) was added to the reaction and stirred for 20 minutes. Chlorotrimethylsilane (6.04 mL, 1.875 eq) was added at −78° C. and stirred for 20 minutes. N-bromosuccinimide (4.74 g, 1.05 eq) was added to the reaction mixture.

The reaction mixture was allowed to stir and warm to room temperature overnight. The reaction mixture was diluted with H₂O. The organic layer was extracted with ethyl acetate. The organic phase was dried over sodium sulfate and the solvent was evaporated to give a yellow oil. The resulting oil was chromatographed on silica gel using hexanes:ethyl acetate (1:1) to give the title bromide.

Characteristic NMR Resonances; ¹H NMR 500 MHz (CDCl₃); 8.61 (d, 1H), 7.72 (dt 1H), 7.50 (dt, 1H), 7.42(d, 2H), 7.24 (m, 1H), 6.99 (d, 2H), 5.34 (d, 1H), 5.22 (s, 2H) 3.78 (s, 3H).

Step 3 Preparation of Methyl α-[[5,7-dipropyl-3-(trifluoromethyl)-1,2-benzisoxazol-6-yl]oxy]-4-[pyridin-2-ylmethoxy]benzeneacetate.

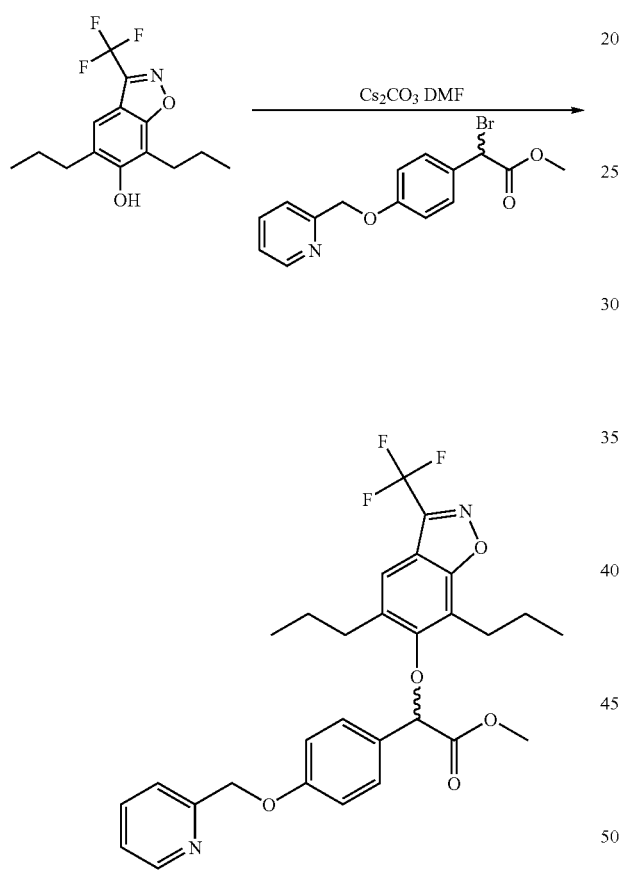

The title ester was prepared as for example 1, step 4 from the indicated bromide (5.31 g, 15.80 mmol) and the indicated phenol (4.54 g, 15.80 mmol). The product was purified by silica gel chromatography (toluene) to yield the desired ester.

Characteristic NMR Resonances; ¹H NMR 500 MHz (CDCl₃); 8.62 (d, 1H), 7.74 (dt 1H), 7.52 (dt, 1H), 7.42(m, 3H), 7.26 (m, 1H), 7.02 (d, 2H), 5.26 (s, 2H), 5.21 (s, 1H) 3.78 (s, 3H), 2.71 (m, 2H), 2.54 (m, 2H), 1.64 (m, 4H), 0.89 (m, 6H)

Step 4 Preparation of racemic α-[[5,7-dipropyl-3-(trifluoromethyl)-1,2-benzisoxazol-6-yl]oxy]-4-[pyridin-2-ylmethoxy]benzeneacetic acid.

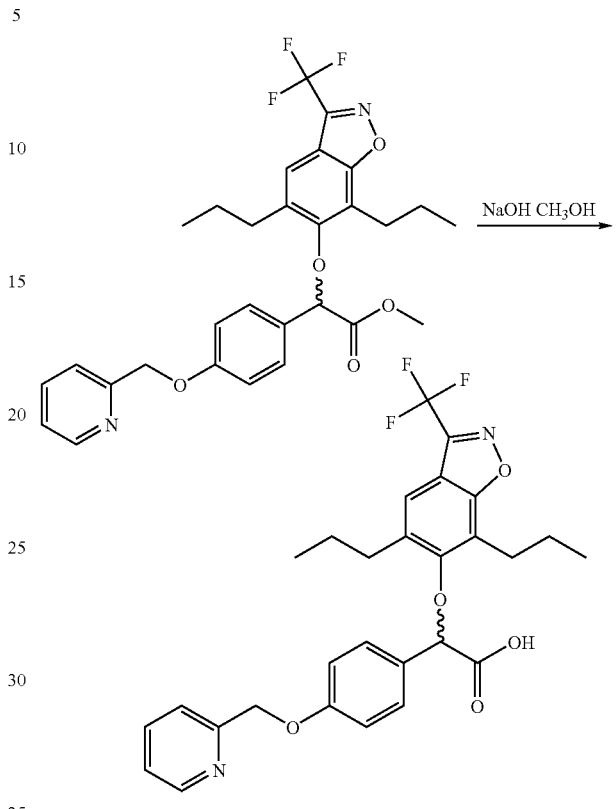

The ester (1.56 grams, 1.0 Eq) was dissolved in methanol (10 ml). Aqueous NaOH (2.5 M, 5.91 ml) was added. The mixture stirred at room temperature for 3 Hrs. The reaction mixture was acidified by 1 equivalent acetic acid. The mixture was washed with water. The mixture was extracted with ethyl acetate. The organic phase was dried over sodium sulfate and the solvent was evaporated to give white solid.

Characteristic NMR Resonances; ¹H NMR 500 MHz (CDCl₃); 8.61 (d, 1H), 7.8 (dt, 1H), 7.58 (d, 1H), 7.36 (m, 4H), 6.89 (d, 2H), 5.16 (m, 3H), 2.64 (m, 2H), 2.48 (m, 2H), 1.52 (m, 4H), 0.82 (m, 6H)

Step 5 Preparation of α-[[5,7-dipropyl-3-(trifluoromethyl)-1,2-benzisoxazol-6-yl]oxy]-4-[pyridin-2-ylmethoxy]benzeneacetic acid (R)Pyrrolidinelactamide ester.

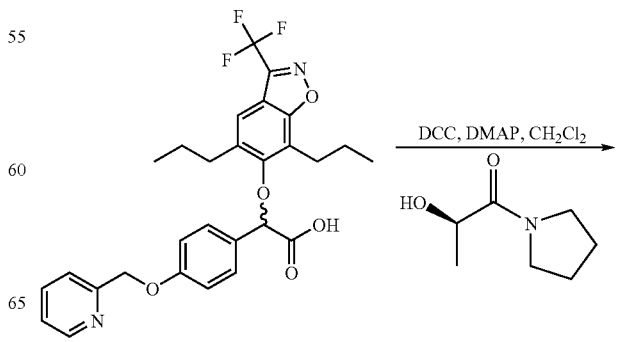

-continued

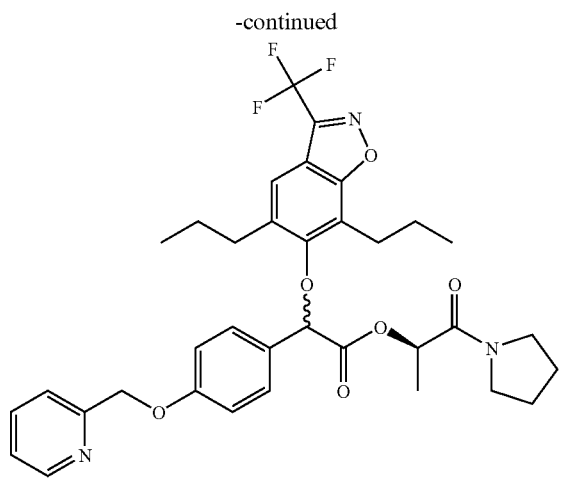

The acid (0.358 g) was dissolved in methylene chloride(3 mL). Pyrrolidine (R)lactamide (0.116 g) and 4-(dimethylamino)pyridine (8.3 mg) was added. The reaction was cooled to 0 C and dicyclohexylcarbodiimide (0.154 g) was added. The reaction was allowed to stir at room temperature for 18 hrs. The reaction mixture was filtered to remove the solids. The filtrate was concentrated. The diastereoisomers were separated by silica gel chromatography (toluene/acetonitrile 80:20) to yield the titled compound.

Characteristic NMR Resonances; $^1$H NMR 500 MHz (CDCl$_3$); 8.62(d, 1H), 7.74 (dt, 1H), 7.52 (d, 1H), 7.42 (d, 2H), 7.37 (s, 1H), 7.26 (m, 1H), 7.20 (d, 2H), 5.29 (s, 1H), 5.27 (q, 1H), 3.71(m, 2H), 3.43 (m, 1H), 3.35 (m, 1H), 2.68 (m, 2H), 2.54 (m, 2H) 1.94 (m, 2H), 1.85 (m, 2H), 1.60 (m, 4H), 1.39 (d, 3H), 0.85 (m, 6H)

Step, 6 Preparation of α-[[5,7-dipropyl-3-(trifluoromethyl)-1,2-benzisoxazol-6-yl]oxy]-4-[pyridin-2-ylmethoxy]benzeneacetic acid.

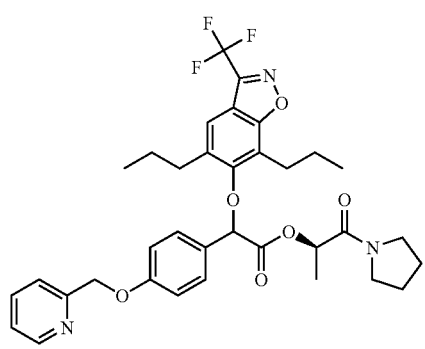

-continued

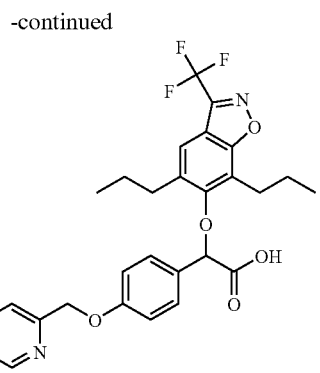

The ester (143 mg, 1.0 eq) was dissolved in tetrahydrofuran (1 ml). Aqueous lithum hydroxide (1.0 M, 0.438 ml, 2.0 eq) was diluted into aqueous hydrogen peroxide (30% nominal, 0.337 ml). The solution of LiOOH was added to the methanol solution of the ester at RT. After 1 Hr the mixture was quenched with 1 M acetic acid and extracted with ethyl acetate. The organic phase was dried over sodium sulfate and the solvent was evaporated to give a oil. The resulting oil was chromatographed on silica gel with hexanes:ethyl acetate plus 1% acetic acid as eluent (20:80) to give the titled compound.

The enantiomeric excess of the final product was determined by HPLC using a ChiralCel OD-R analytical column with acetonitrile water 0.1% TFA as eluent.

Example 31

Step 1 Preparation of Ethyl α-[4-(1-oxopropyl)-2,6-dipropylphenoxy]-3-pyridineacetate.

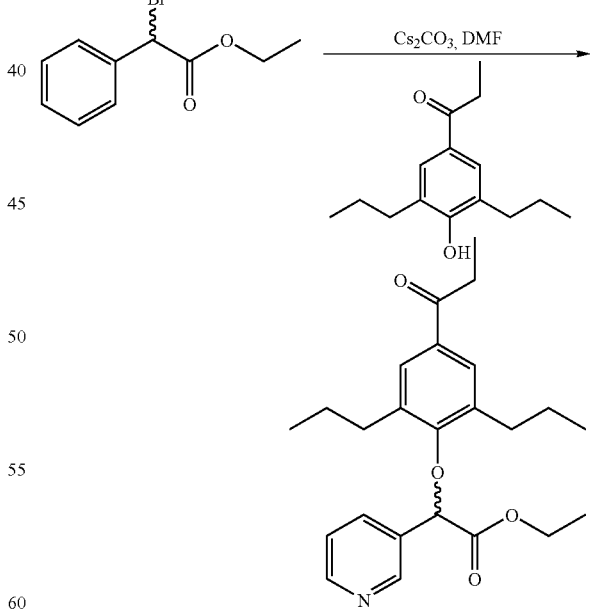

The title ester was prepared as was described for example 1, step 4 from the indicated bromide (104 mg) and the indicated phenol (106 mg). The product was purified by silica gel chromatography (toluene:hexanes 90:10) to yield the desired ester.

Characteristic NMR Resonances; $^1$H NMR 500 MHz (CDCl$_3$); 8.70 (s, 1H), 8.65 (d, 1H), 7.93 (dd, 1H), 7.60 (s, 2H), 7.39 (dt, 1H), 5.22 (s 1H), 4.23 (q, 2H), 2.97(m, 2H), 2.45 (m, 4H), 1.56 (m, 4H), 1.23 (m, 6H), 0.83 (m, 6H).

Step 2 Preparation of α-[4-(1-oxopropyl)-2,6-dipropylphenoxy]-3-pyridineacetic acid.

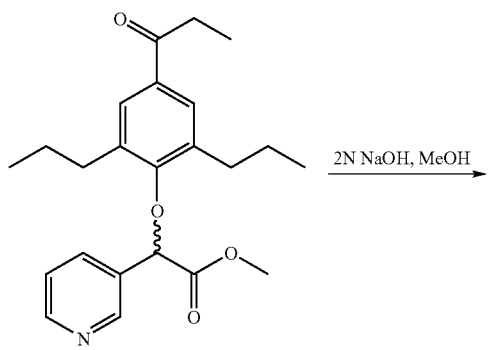

The title acid was prepared as was described for example 1, step 5 from the indicated ester (98 mg, 1.0 eq) and NaOH (0.491 mL, 5 M, 2.5 eq).

Characteristic NMR Resonances; $^1$H NMR 500 MHz (CDCl$_3$); 8.92(s, 1H), 8.80 (d, 1H), 8.40 (dd, 1H), 7.78 (dt, 1H),7.61 (s, 2H), 5.40 (s, 1H), 2.95 (q, 2H), 2.49 (m, 4H), 1.58 (m, 4H), 1.25 (t, 3H), 0.80 (m, 6H).

Example 32

Step 1 Preparation of Methyl 2-Bromo-2-(2-phenyl-1,3-thiazol-4-yl)acetate

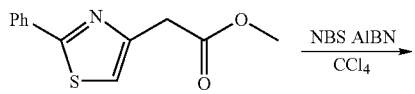

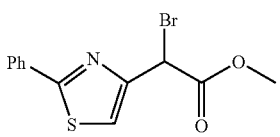

To a solution of the starting ester (420 mg, 1.0 eq) in CCl$_4$ (20 mL) were added NBS (650 mg, 2.0 eq) and catalytic amount of AIBN. The mixture was stirred at 70° C. under N$_2$ for 8 h. After cooling to ambient temperature, the precipitate was removed by filtration. The filtrate was concentrated in vac. Purification by flash chromatography (SiO$_2$, EtOAc/Hexanes 1:4) gave the desired product.

Characteristic NMR Resonances; $^1$H NMR 500 MHz (CDCl$_3$); 7.97 (m, 2H), 7.68 (s, 1H), 7.47 (m, 3H), 5.72 (s, 1H), 3.89 (s, 3H).

Step 2 Preparation of Methyl α-[5,7-dipropyl-3-(trifluoromethyl)-1,2-benzisoxazol-6-yl]oxy)-2-(2-phenyl-1,3-thiazol-4-yl)acetate.

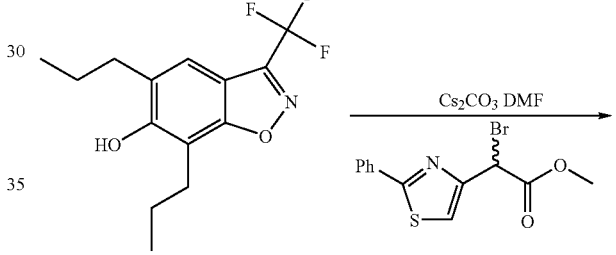

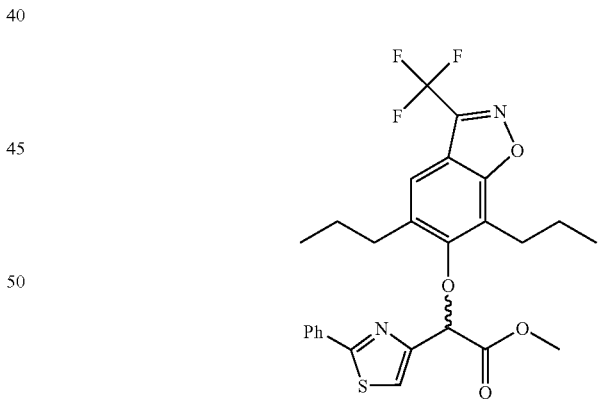

The title ester was prepared as was described for example 1, step 4 from the indicated bromide and phenol. The resulting solid was purified by chromatography on silica gel using ethyl acetate and hexane (1:9) as eluent to give the titled compound.

Characteristic NMR Resonances; $^1$H NMR 500 MHz (CDCl$_3$); 7.96 (m, 2H), 7.47 (m, 3H), 7.43 (s, 1H+1H), 5.63 (s, 1H), 3.87 (s, 3H), 2.84 (m, 2H), 2.63 (t, 2H), 1.8–1.6 (m, overlapping signals, 4H), 0.93 (t+t, 6H).

Step 3 Preparation of α-[5,7-dipropyl-3-(trifluoromethyl)-1,2-benzisoxazol-6-yl]oxy)-2-(2-phenyl-1,3-thiazol-4-yl)acetic acid.

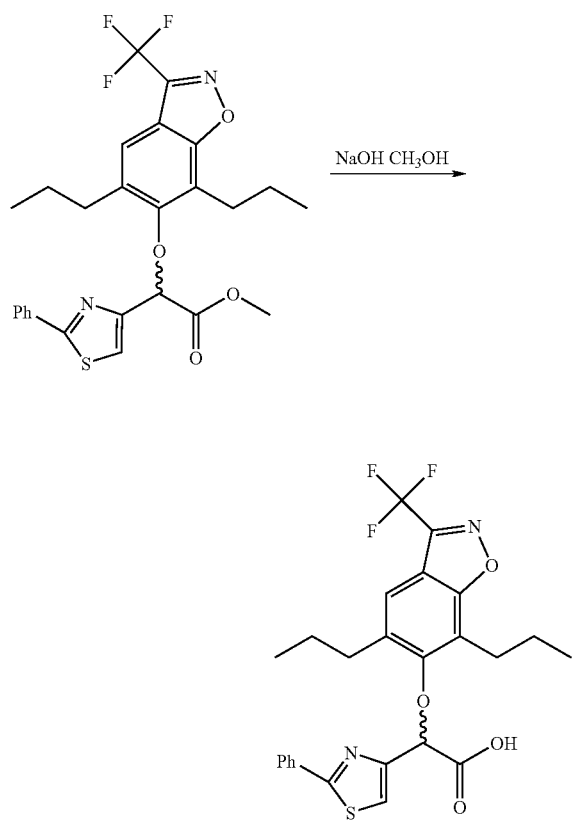

The title acid was prepared as was described for example 1, step 5 from the indicated ester (1.0 eq) and aqueous NaOH (1.1 eq). The resulting oil was crystallized from hexanes to give the titled compound.

Characteristic NMR Resonances; $^1$H NMR 500 MHz (CDCl$_3$); 7.95 (m, 2H), 7.48 (m, 3H), 7.42 (s, 1H), 7.36 (s, 1H), 5.60 (s, 1H), 2.79 (m, 2H), 2.61 (t, 2H), 1.8–1.6 (m, overlapping signals, 4H), 0.91 (t+t, 6H).

Example 33

Step 1 Preparation of 2,6-diallyl-4-benzyloxyphenol.

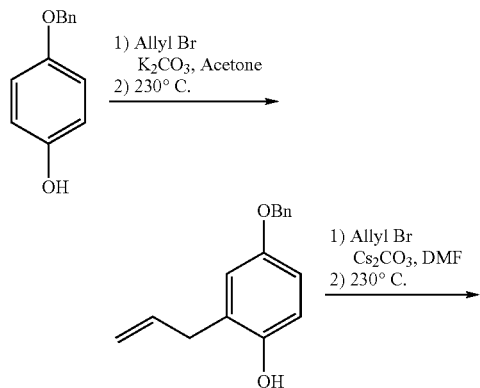

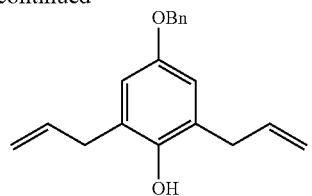

To a solution of starting 4-benzyloxyphenol (20 g) in acetone (800 mL) were added allylbromide (50 mL) and K$_2$CO$_3$ (60 g). The reaction mixture was refluxed overnight. After cooling to the room temperature, the insoluble materials were removed by filtration. The filtrate was concentrated in vac. The residue was partitioned between ethyl ether (500 mL) and 2N aqueous NaOH (200 mL). The organic layer was washed with water and brine, dried over anhydrous MgSO$_4$, filtered, and concentrated in vac. to give the desired product.

The neat allyl ether (21 g) obtained above was heated at 230° C. under N$_2$ atmosphere for 3 h to give after cooling to room temperature the desired 2-allyl4-benzyloxyphenol, which was used in the next step without further purification.

To a solution of the above obtained 2-allyl-4-benzyloxyphenol (21 g) in DMF (200 mL) were added Cs$_2$CO$_3$ (57 g) and allylbromide (38 mL). The reaction mixture was stirred at room temperature overnight before it was poured into ether (1.0 L), washed with water (2×) and brine, dried over anhydrous MgSO$_4$, filtered, and concentrated in vac. to give the desired allyl ether.

The neat allyl ether (22 g) obtained above was heated at 230° C. under N$_2$ atmosphere for 3 h to give the desired 2,6-diallyl-4-benzyloxyphenol, which was purified by flash chrotography (SiO$_2$, EtOAc/Hexanes 1:20).

NMR (CDCl$_3$) δ7.50–7.30 (m, overlapping signals, 5H), 6.69 (s, 2H), 6.00 (m, 2H), 5.18 (m, 2H), 5.15 (m, 2H), 5.00 (s, 2H), 5.48 (s, broad, 1H), 3.40 (dd, 4H).

Step 2. Preparation of Methyl α-(4-hydroxy-2,6-dipropylphenoxy)-4-chloro benzeneacetate.

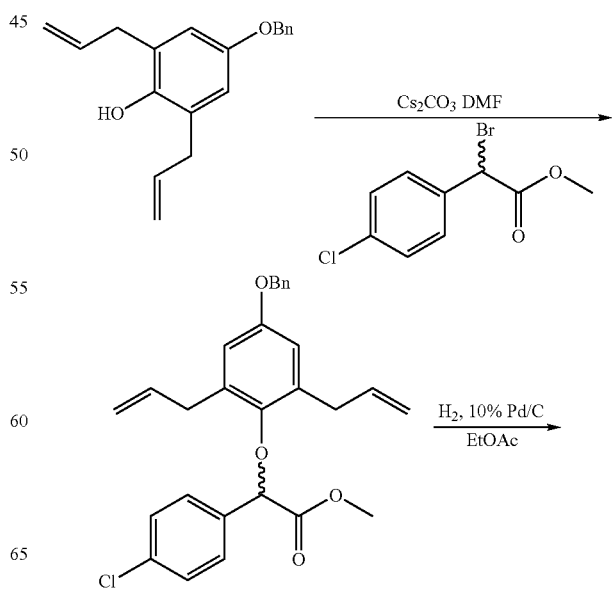

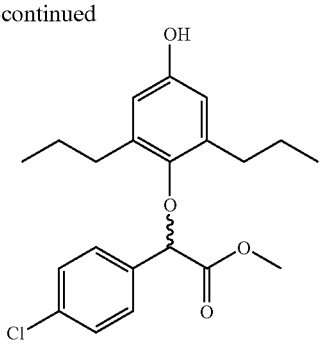

To a solution of 2,6-diallyl-4-benzyloxyphenol (200 mg, 1.0 eq) in DMF (8 mL) were added methyl α-bromo-4-chlorobenzeneacetate (190 mg, 1.0 eq) and Cs₂CO₃ (285 mg, 1.2 eq). The reaction mixture was stirred at room temperature for 15 h, poured into ether, washed with water and brine, dried over MgSO₄, filtered, and concentrated in vac. Purification by chromatography (SiO₂, EtOAc/Hexanes 1:20) afforded the desired methyl α-(2,6-diallyl-4-hydroxyphenoxy)-4-chlorobenzeneacetate.

The above obtained compound (150 mg) was dissolved in EtOAc (10 mL) and hydrogenated under H₂ atmosphere (balloon, 1 atm) in the presence of catalytic amount of 10% Pd/C at room temperature for 1 h. The catalyst was removed by filtration. The filtrate was concentrated in vac to give the titled compound.

Characteristic NMR Resonances; $^1$H NMR 500 MHz (CDCl₃); 7.45 (d, 2H), 7.39 (d, 2H), 6.49 (s, 2H), 5.05 (s, 1H), 4.78 (s, broad, 1H), 3.78 (s, 3H), 2.32 (m, 4H), 1.44 (m, 4H), 0.80 (t, 6H).

Step 3 Preparation of Methyl α-[2,6-dipropyl-4-[2-(5-methyl-2-phenyl-1,3-oxazol-4-yl)ethoxy]phenoxy]-4-chlorobenzeneacetate.

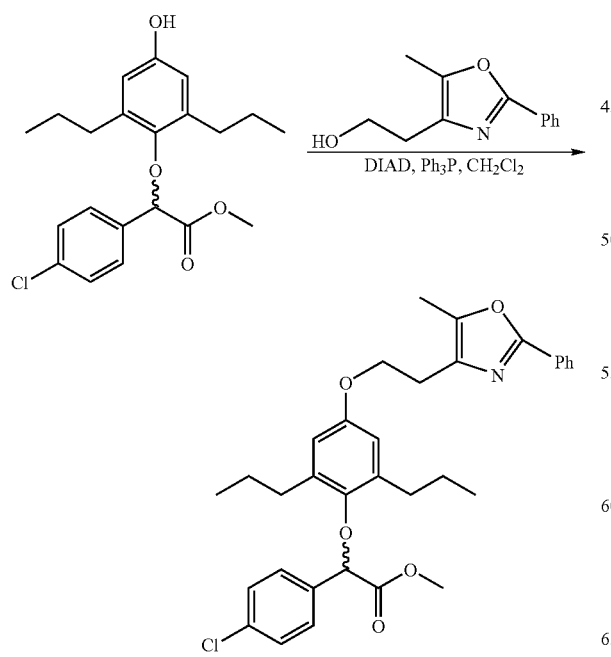

To a mixture of starting phenol (100 mg, 1.0 eq) and 2-(5-methyl-2-phenyl-1,3-oxazol-4-yl)ethanol (68 mg, 1.2 eq) in CH₂Cl₂ (5 mL) were added Ph₃P (145 mg, 2.0 eq) and DIAD (0.13 mL, 2.0 eq). The reaction mixture was stirred at room temperature for 24 h. Purification by flash chromatography (SiO₂, EtOAc/Hexanes 1:4) gave the desired coupling product.

Characteristic NMR Resonances; $^1$H NMR 500 MHz (CDCl₃) δ8.00 (d, 2H), 7.45 (m, overlapping signals, 5H), 7.36 (d, 2H), 6.63 (s, 2H), 5.03 (s, 1H), 4.19 (t, 2H), 3.75 (s, 3H), 2.96 (t, 2H), 2.38 (s, 3H), 2.34 (m, 4H), 1.47 (m, 4H), 0.81 (t, 6H).

Step 4 Preparation of α-[2,6-dipropyl-4-[2-(5-methyl-2-phenyl-1,3-oxazol-4-yl)ethoxy]phenoxy]-4-chlorobenzeneacetic acid.

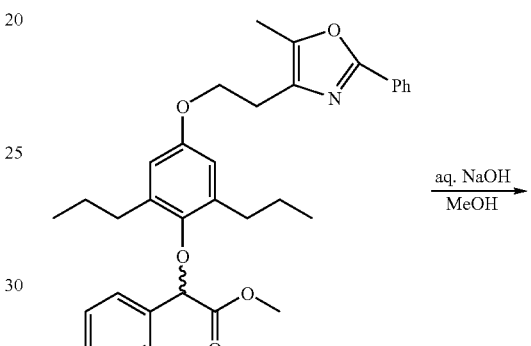

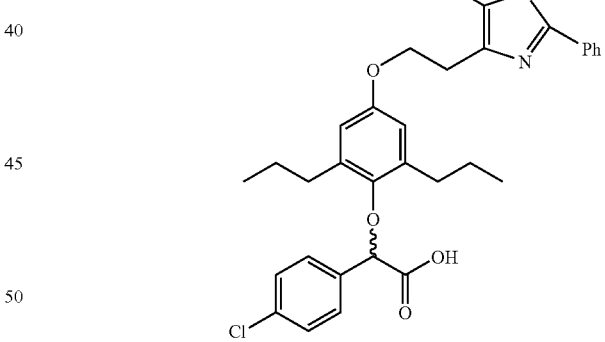

The title acid was prepared as was described for example 1, step 5 from the indicated ester (1.0 eq) and aquoues NaOH (1.1 eq). The resulting oil was crystallized from hexanes to give the titled compound.

Characteristic NMR Resonances; $^1$H NMR 500 MHz (CDCl₃); 8.00 (m, 2H), 7.45 (m, 3H), 7.40 (d, 2H), 7.37 (d, 2H), 6.53 (s, 2H), 5.07 (s, 1H), 4.19 (t, 2H), 2.98 (t, 2H), 2.39 (s, 3H), 2.30 (m, 4H), 1.55 (m, 2H), 1.45 (m, 2H), 0.82 (t, 6H).

What is claimed is:

1. A compound having the formula I:

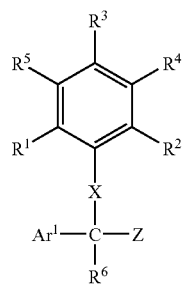

I including pharmaceutically acceptable salts thereof, wherein
$R^1$ is selected from the group consisting of (a) halogen, (b) $C_{1-6}$ alkyl, where alkyl is linear or branched and is optionally substituted with 1–3F, and (c) —$OC_1$–$C_6$ alkyl, where —$OC_1$–$C_6$ alkyl is linear or branched and is optionally substituted with 1–3 halogens, independently selected from Cl and F, with the proviso that $R^1$ and $R^2$ are not both $CH_3$;

$R^2$ is selected from the group consisting of $C_1$–$C_6$ alkyl and $C_3$–$C_{12}$ Alicyclic, wherein alkyl is linear or branched and is optionally substituted with 1–3F, and Alicyclic is optionally substituted with 1–5 halogens;

$R^3$ and $R^4$ are joined together to yield a 5-membered ring containing (a) 1–3 heteroatoms selected from O, N and S, (b) 2–5 carbon atoms, and (c) optionally one carbonyl group, wherein the 5-membered ring is fused to the benzene ring, and the benzene ring and fused 5-membered ring together form a Heteroaryl or Heterocycle which optionally contains one carbonyl group in the 5-membered fused ring and which is optionally substituted on the 5-membered fused ring with 1–2 substituents independently selected from $R^8$;

$R^5$ is H or Halogen;

$R^6$ is selected from the group consisting of H, halogen, $CH_3$ and $CF_3$;

Each $R^7$ is independently selected from the group consisting of halogen, $C_1$–$C_6$ alkyl, $C_1$–$C_6$ alkoxy, —$SC_{1-6}$ alkyl, —OAryl, $C_2$–$C_6$ alkenyl, $C_2$–$C_6$ alkynyl, —CN, —$C(O)OC_1$–$C_3$ alkyl, and —$C(O)C_1$–$C_3$alkyl, wherein each alkyl, alkenyl, alkoxy and alkynyl and each alkyl portion of a substituent is linear or branched and is optionally substituted with 1–5 halogen atoms and/or 1 substituent selected form Aryl and Heteroaryl, and each Aryl and Heteroaryl is optionally substituted with 1–3 groups independently selected from halogen, $CH_3$, $CF_3$, —$OCH_3$ and —$OCF_3$;

Each $R^8$ is independently selected from the group consisting of (a) —$OC_1$–$C_5$ alkyl, which may be linear or branched and is optionally substituted with 1–3 F; (b) $C_1$–$C_9$ alkyl, which may be linear or branched and is optionally substituted with one Aryl, 1–5 halogens independently selected from Cl and F, and/or one —COOH; (c) Aryl; and (d) Heteroaryl; wherein Aryl and Heteroaryl are optionally substituted with 1–3 substituents independently selected from the group consisting of Cl, F, $C_1$–$C_5$ alkyl, and —$OC_1$–$C_5$alkyl, wherein each alkyl and each —$OC_1$–$C_5$alkyl may be linear or branched, and is optionally substituted with 1–3 substituents independently selected from halogen —$OCH_3$, and —$OCF_3$;

Aryl is an aromatic carbocyclic mono- or bicyclic ring system containing 6–10 atoms in the ring or rings;

Heteroaryl is a mono- or bicyclic aromatic ring system containing 4–11 atoms in the ring or rings, wherein at least one atom in the ring or rings is a heteroatom selected from N, O and S;

Heterocycle is a fully or partially saturated monocyclic or bicyclic ring system having 4–11 atoms in the ring or rings and at least one heteroatom selected from O, N, and S in the ring or rings;

Alicyclic is a substituent group that has one $C_3$–$C_6$cycloalkyl and one or more alkyl groups which may be linear or branched attached to the cycloalkyl group, wherein the point of attachment may be through the cycloalkyl or through an alkyl group;

$Ar^1$ is selected from the group consisting of phenyl, thienyl, thiazolyl, oxazolyl and pyridyl, and is optionally substituted with Aryl, pyridyl or 1–3 groups independently selected from $R^7$;

X is O or S; and

Z is selected from the group consisting of —COOH, tetrazole, and —$C(O)NHS(O)_2R^8$.

2. The compound having formula I as recited in claim 1, wherein X is O.

3. The compound having formula I as recited in claim 1, wherein Z is —$CO_2H$.

4. A compound according to claim 1 having formula 1a:

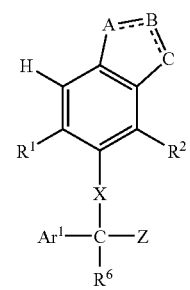

Ia including pharmaceutically acceptable salts thereof, wherein
A-B and B—C are each connected by a bond, and optionally A-B or B—C can be a double bond, thereby yielding a five-membered ring fused to the benzene ring to which A and C are bonded, wherein A, B, and C are each independently selected from N, $NR^9$, C, $CR^9$, $CR^9_2$, C=O, O, S, S(O), and $S(O)_2$, wherein at least one of A, B, and C comprises a heteroatom selected from N, S and O that is in the ring;

Each $R^9$ is independently selected from $R^8$ and H; and $R^1$, $R^2$, $R^6$, $R^7$, $R^8$, $Ar^1$, X and Z are as defined in claim 1.

5. A compound having formula I as recited in claim 1, wherein X is O and Z is —$CO_2H$.

6. A compound having formula I as recited in claim 1, wherein $Ar^1$ is phenyl, which is optionally substituted with 1–3 groups independently selected from $R^7$.

7. A compound as recited in claim 1, wherein
$R^1$ is selected from Cl, F, and $C_2$–$C_4$ alkyl, which may be linear or branched and is optionally substituted with 1–3F;

$R^2$ is $C_2$–$C_4$ alkyl, which may be linear or branched and is optionally substituted with 1–3F;

$R^3$ and $R^4$ are joined together to form a membered 5-membered ring containing 1–3 heteroatoms selected from S, N, and O in the ring that is fused to the benzene ring to which $R^3$ and $R^4$ are attached, so that the benzene ring and 5-membered ring together form a fused ring system selected from benzisoxazole, benzisothiazole, benzthiazole, benzoxazole, benzofuran, benzothiophene, benzimidazole, indole, benzoxazolone, benzisoxazolone; and benzimidazolone, wherein the ring is optionally substituted with 1–2 substituents independently selected from $R^8$;

$R^6$ is selected from H, halogen, $CH_3$, and $CF_3$;

$R^7$ is selected from the group consisting of $C_1$–$C_6$alkyl, —OAryl, $C_3$–$C_{12}$Alicyclic, —OC$_1$–C$_6$alkyl, —SC$_1$–C$_6$alkyl and —C(O)C$_1$–C$_3$alkyl, wherein alkyl in each occurrence is linear or branched and is optionally substituted with 1–3 halogens and/or one substituent selected from Aryl and Heteroaryl, and each Aryl and Heteroaryl is optionally substituted with 1–3 substituents independently selected from halogen, $CH_3$, $CF_3$, —$OCH_3$ and —$OCF_3$;

Each $R^8$ is independently selected from halogen, $C_1$–$C_3$alkyl, and phenyl, wherein $C_1$–$C_3$alkyl is linear or branched and is optionally substituted with 1–3 halogens, and phenyl is optionally substituted with 1–3 substituents independently selected from halogen, $CH_3$, $CF_3$, —$OCH_3$ and —$OCF_3$;

and $R^5$, $R^9$, $Ar^1$, X and Z are as defined in claim 1.

8. A compound as recited in claim 4, wherein the group -A-B—C—, in which the bonds between A and B and between B and C are optionally single or double bonds, is selected from the group consisting of:
—C($R^9$)=N—O—,
—C($R^9$)=N—S—,
—C($R^9$)$_2$—N($R^9$)—O—,
—C($R^9$)$_2$—N($R^9$)—S—,
—N($R^9$)—C(=O)—O—,
—N($R^9$)—C(=O)—S—,
—N($R^9$)—O—C(=O)—,
—N($R^9$)—S—C(=O)—,
—N=C($R^9$)—O—,
—N=C($R^9$)—S—,
—N($R^9$)—C($R^9$)$_2$—O—,
—N($R^9$)—C($R^9$)$_2$—S—,
—C(=O)—N($R^9$)—O—;
—C(=O)—N($R^9$)—S—;
—C(=O)—O—N($R^9$)—; and
—C(=O)—S—N($R^9$)—;

or the group —C—B-A- is selected from the group consisting of:
—C($R^9$)=N—O—,
—C($R^9$)=N—S—,
—C($R^9$)$_2$—N($R^9$)—O—,
—C($R^9$)$_2$—N($R^9$)—S—,
—N($R^9$)—C(=O)—O—,
—N($R^9$)—C(=O)—S—,
—N($R^9$)—O—C(=O)—,
—N($R^9$)—S—C(=O)—,
—N=C($R^9$)—O—,
—N=C($R^9$)—S—,
—N($R^9$)—C($R^9$)$_2$—O—,
—N($R^9$)—C($R^9$)$_2$—S—,
—C(=O)—N($R^9$)—O—;
—C(=O)—N($R^9$)—S—;
—C(=O)—O—N($R^9$)—; and
—C(=O)—S—N($R^9$)—.

9. A compound as recited in claim 8, wherein $R^1$ is selected from Cl, F, and $C_2$–$C_4$ alkyl, which may be linear or branched and is optionally substituted with 1–3F;

$R^2$ is $C_2$–$C_4$ alkyl, which may be linear or branched and is optionally substituted with 1–3F;

$R^6$ is selected from H, halogen, $CH_3$, and $CF_3$;

Each $R^7$ is independently selected from the group consisting of $C_1$–$C_6$alkyl, —OAryl, $C_3$–$C_{12}$Alicyclic, —OC$_1$–C$_6$alkyl, —SC$_1$–C$_6$alkyl and —C(O)C$_1$–C$_3$alkyl, wherein alkyl in each occurrence is linear or branched and is optionally substituted with 1–3 halogens, and Aryl is optionally substituted with 1–3 substituents independently selected from halogen, $CH_3$, $CF_3$, —$OCH_3$ and —$OCF_3$;

$R^8$ is independently selected from halogen, $C_1$–$C_3$alkyl, and phenyl, wherein $C_1$–$C_3$alkyl is linear or branched and is optionally substituted with 1–3 halogens, and phenyl is optionally substituted with 1–3 substituents independently selected from halogen, $CH_3$, $CF_3$, —$OCH_3$ and —$OCF_3$;

Each $R^9$ is independently selected from $R^8$ and H;

and $R^5$, $Ar^1$, X and Z are as defined in claim 1.

10. A compound as recited in claim 9, wherein the group -A-B—C— is selected from —C($R^9$)=N—O—, —C(=O)—N($R^9$)—O—, and —N($R^9$)—C(=O)—O—;

$R^1$ is selected from Cl, F and linear or branched $C_2$–$C_4$alkyl;

$R^2$ is linear or branched $C_2$–$C_4$alkyl;

$R^6$ is H;

Each $R^7$ is independently selected from F, Cl, $C_1$–$C_4$ alkyl, —OC$_1$–C$_4$ alkyl, —SC$_1$–C$_4$ alkyl, and —Ophenyl, wherein in each instance, alkyl is linear or branched and is optionally substituted with 1–5 F, and —Ophenyl is optionally substituted with 1–3 substituents independently selected from halogen, $CH_3$, $CF_3$, —$OCH_3$ and —$OCF_3$; and $R^8$ is selected from $C_{1-5}$ alkyl, which is linear or branched and is optionally substituted with 1–3F, and phenyl, which is optionally substituted with 1–3 substituents independently selected from halogen, $CH_3$, $CF_3$, —$OCH_3$ and —$OCF_3$.

11. A compound as recited in claim 10, wherein $R^1$ is selected from Cl, F and n-$C_3$–$C_4$alkyl;

$R^2$ is n-$C_3$–$C_4$alkyl; and $Ar^1$ is phenyl, which is optionally substituted with 1–3 groups independently selected from $R^7$.

12. A compound represented by any of the structures shown below, including pharmaceutically acceptable salts thereof:

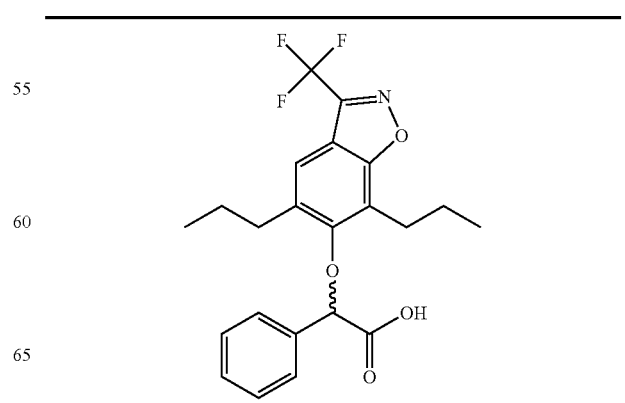

-continued
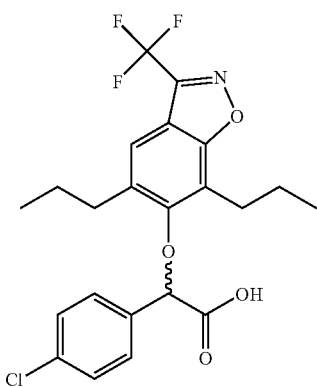
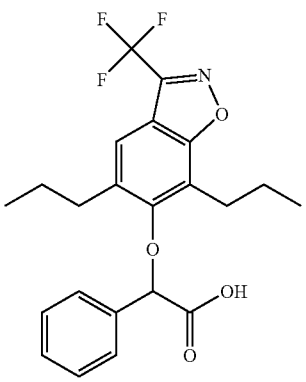
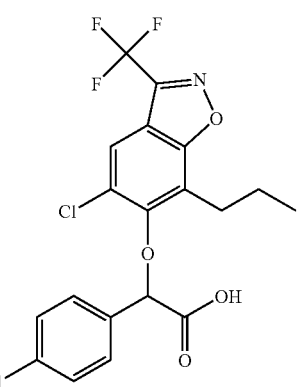
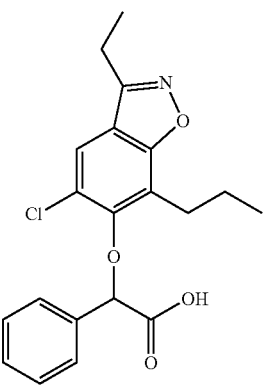
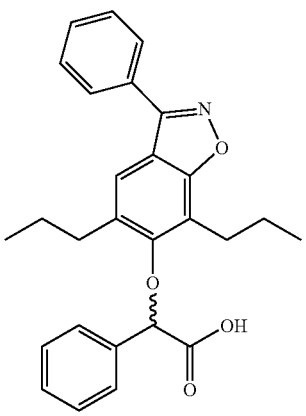

129 -continued
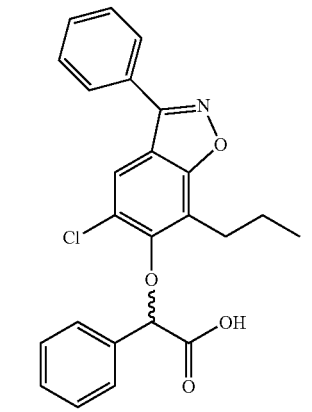
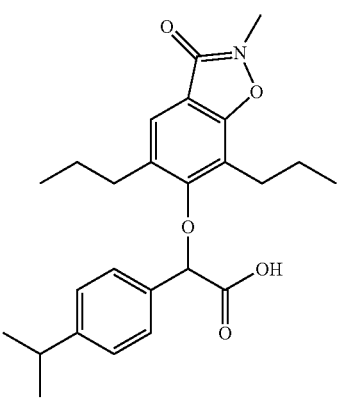
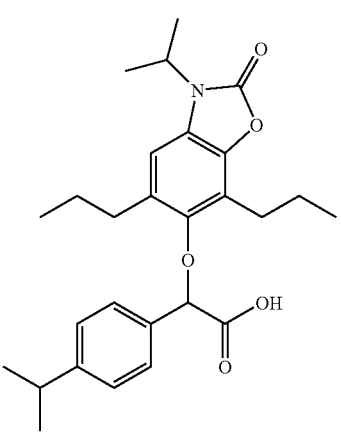
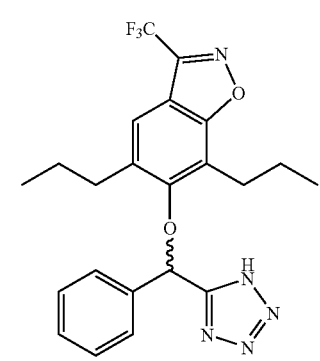
130 -continued
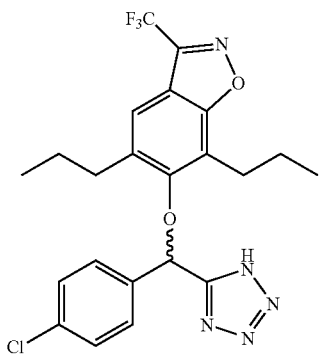
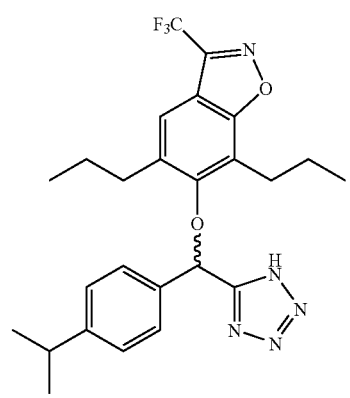
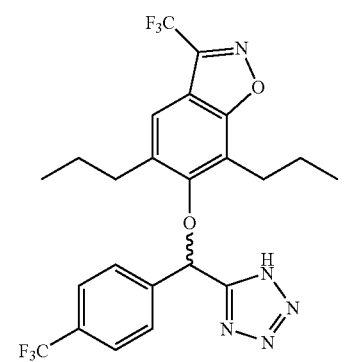
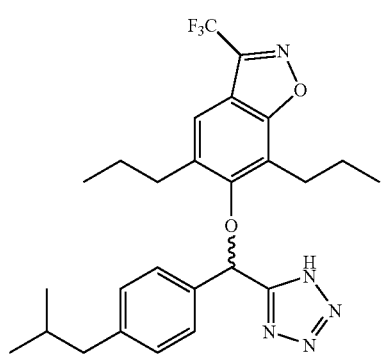

| 131 | 132 |
|---|---|
| -continued | -continued |
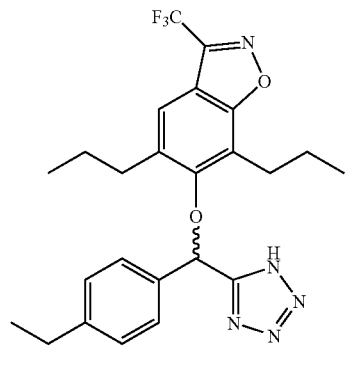
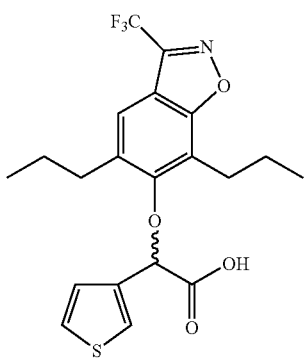
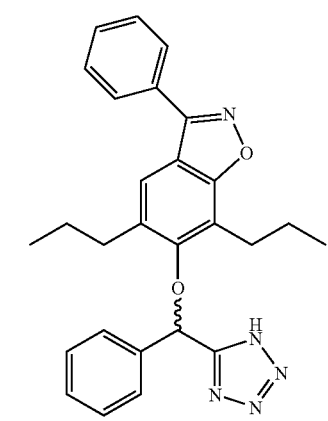
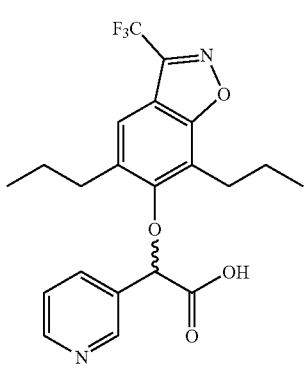
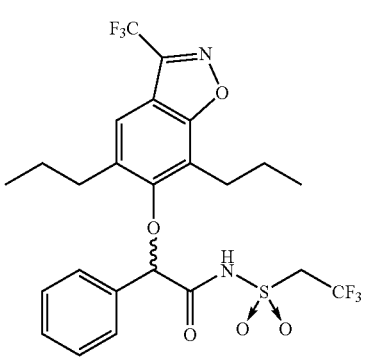
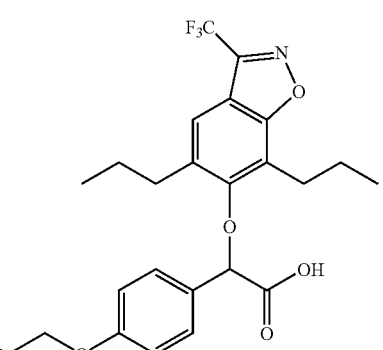
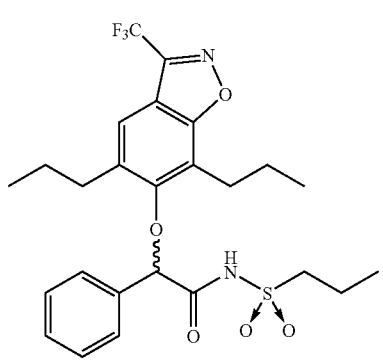
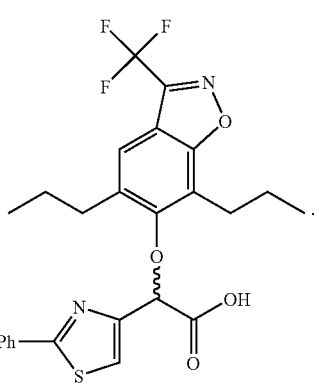

13. A compound as described below, including pharmaceutically acceptable salts thereof:
- α-[[5,7-dipropyl-3-(trifluoromethyl)-1,2-benzisoxazol-6-yl]oxyl]benzeneacetic acid;
- α-[[5,7-dipropyl-3-(trifluoromethyl)-1,2-benzisoxazol-6-yl]oxy]-4-chlorobenzeneacetic acid;
- α-[[5,7-dipropyl-3-(trifluoromethyl)-1,2-benzisoxazol-6-yl]oxy]-4-[(trifluoromethyl)thio]benzeneacetic acid;
- α-[[5,7-dipropyl-3-(trifluoromethyl)-1,2-benzisoxazol-6-yl]oxy]-4-(1-methylethyl)benzeneacetic acid;
- α-[[5,7-dipropyl-3-(trifluoromethyl)-1,2-benzisoxazol-6-yl]oxy]-4-(2-methylpropyl)benzeneacetic acid;
- α-[[5,7-dipropyl-3-(trifluoromethyl)-1,2-benzisoxazol-6-yl]oxy]benzeneacetic acid;
- α-[[5-chloro-7-propyl-3-(trifluoromethyl)-1,2-benzisoxazol-6-yl]oxy]-4-chlorobenzeneacetic acid;
- α-[[5-chloro-3-ethyl-7-propyl-1,2-benzisoxazol-6-yl]oxy]benzeneacetic acid;
- α-[[5,7-dipropyl-3-phenyl-1,2-benzisoxazol-6-yl]oxy]benzeneacetic acid;
- α-[[5-chloro-3-phenyl-7-propyl-1,2-benzisoxazol-6-yl]oxy]benzeneacetic acid;
- α-[(2,3-dihydro-2-methyl-3-oxo-5,7-dipropyl-1,2-benzisoxazol-6-yl)oxy]-4-(1-methylethyl)benzeneacetic acid;
- α-[(2,3-dihydro-3-(1-methylethyl)-2-oxo-5,7-dipropyl-1,3-benzoxazol-6-yl)oxy]-4-(1-methylethyl)benzeneacetic acid;
- 6-[phenyl(1H-tetrazol-5-yl)methoxy]-5,7-dipropyl-3-(trifluoromethyl)-1,2-benzisoxazole;
- 6-[(4-chlorophenyl)(1H-tetrazol-5-yl)methoxy]-5,7-dipropyl-3-(trifluoromethyl)-1,2-benzisoxazole;
- 6-[[4-(1-methylethyl)phenyl](1H-tetrazol-5-yl)methoxy]-5,7-dipropyl-3-(trifluoromethyl)-1,2-benzisoxazole;
- 6-[(1H-tetrazol-5-yl)[4-(trifluoromethyl)phenyl]methoxy]-5,7-dipropyl-3-(trifluoromethyl)-1,2-benzisoxazole;
- 6-[[4-(2-methylpropyl)phenyl](1H-tetrazol-5-yl)methoxy]-5,7-dipropyl-3-(trifluoromethyl)-1,2-benzisoxazole;
- 6-[(4-ethylphenyl)(1H-tetrazol-5-yl)methoxy]-5,7-dipropyl-3-(trifluoromethyl)-1,2-benzisoxazole;
- 6-[(phenyl)(1H-tetrazol-5-yl)methoxy]-5,7-dipropyl-3-phenyl-1,2-benzisoxazole;
- α-[[5,7-dipropyl-3-(trifluoromethyl)-1,2-benzisoxazol-6-yl]oxy]]-N-[(2,2,2-trifluoroethyl)sulfonyl]benzeneacetamide;
- α-[[5,7-dipropyl-3-(trifluoromethyl)-1,2-benzisoxazol-6-yl]oxy]]-N-[propylsulfonyl]benzeneacetamide;
- α-[[5,7-dipropyl-3-(trifluoromethyl)-1,2-benzisoxazol-6-yl]oxy]-3-thiopheneacetic acid;
- α-[[5,7-dipropyl-3-(trifluoromethyl)-1,2-benzisoxazol-6-yl]oxy]-3-pyridineacetic acid;
- α-[[5,7-dipropyl-3-(trifluoromethyl)-1,2-benzisoxazol-6-yl]oxy]-4-[pyridin-2-ylmethoxy]benzeneacetic acid; and
- α-[5,7-dipropyl-3-(trifluoromethyl)-1,2-benzisoxazol-6-yl]oxy)-2-(2-phenyl-1,3-thiazol-4-yl)acetic acid.

14. A pharmaceutical composition comprising a compound of claim 1 and a pharmaceutically acceptable carrier.

15. A compound as recited in claim 1, wherein the stereochemistry at the C that is attached to Z, $Ar^1$, $R^6$ and X is R.

16. A compound as recited in claim 1, wherein the stereochemistry at the C that is attached to Z, $Ar^1$, $R^6$ and X is S.

17. A method for treating or controlling non-insulin dependent (Type 2) diabetes mellitus in a mammalian patient in need of such treatment which comprises administering to said patient a therapeutically effective amount of a compound of claim 1.

18. A method for treating or controlling hyperglycemia in a mammalian patient in need of such treatment which comprises administering to said patient a therapeutically effective amount of a compound of claim 1.

19. A method for treating or controlling lipid disorders, hyperlipidemia, or low HDL in a mammalian patient in need of such treatment which comprises administering to said patient a therapeutically effective amount of a compound of claim 1.

20. A method for treating or controlling obesity in a mammalian patient in need of such treatment which comprises administering to said patient a therapeutically effective amount of a compound of claim 1.

21. A method for treating or controlling hypercholesterolemia in a mammalian patient in need of such treatment which comprises administering to said patient a therapeutically effective amount of a compound of claim 1.

22. A method for treating or controlling hypertriglyceridemia in a mammalian patient in need of such treatment which comprises administering to said patient a therapeutically effective amount of a compound of claim 1.

23. A method for treating or controlling dyslipidemia and/or low HDL cholesterol in a mammalian patient in need of such treatment which comprises administering to said patient a therapeutically effective amount of a compound of claim 1.

24. A method for treating or controlling atherosclerosis in a mammalian patient in need of such treatment which comprises administering to said patient a therapeutically effective amount of a compound of claim 1.

25. A method for treating or controlling cachexia in a mammalian patient in need of such treatment which comprises administering to said patient a therapeutically effective amount of a compound of claim 1.

26. A method for the treatment or control of one or more conditions selected from hypercholesterolemia, atherosclerosis, low HDL levels, high LDL levels, hyperlipidemia, hypertriglyceridemia, and dyslipidemia, which method comprises administering to a mammalian patient in need of such treatment a therapeutically effective amount of a compound of claim 1 and a therapeutically effective amount of an HMG-CoA reductase inhibitor.

27. The method as recited in claim 26, wherein the HMG-CoA reductase inhibitor is a statin.

28. The method as recited in claim 27, wherein the statin is selected from the group consisting of lovastatin, simvastatin, pravastatin, fluvastatin, atorvastatin, itavastatin, ZD-4522 and rivastatin.

* * * * *